(12) United States Patent
Johnson et al.

(10) Patent No.: US 8,242,174 B2
(45) Date of Patent: Aug. 14, 2012

(54) HYDROXAMIC ACID DERIVATIVES OF ANILINE USEFUL AS THERAPEUTIC AGENTS FOR TREATING ANTHRAX POISONING

(75) Inventors: Alan T. Johnson, Kaneohe, HI (US); Guan-Sheng Jiao, Honolulu, HI (US)

(73) Assignee: PanThera Biopharma LLC, Aiea, HI (US)

( * ) Notice: Subject to any disclaimer, the term of this patent is extended or adjusted under 35 U.S.C. 154(b) by 1233 days.

(21) Appl. No.: 12/011,790

(22) Filed: Jan. 30, 2008

(65) Prior Publication Data

US 2012/0157462 A1     Jun. 21, 2012

Related U.S. Application Data

(60) Provisional application No. 60/898,988, filed on Feb. 1, 2007.

(51) Int. Cl.
*A01N 37/28* (2006.01)
*A61K 31/19* (2006.01)
*C07C 259/04* (2006.01)

(52) U.S. Cl. ........................................ 514/575; 562/621

(58) Field of Classification Search ........................ None
See application file for complete search history.

(56) References Cited

U.S. PATENT DOCUMENTS

| 4,122,186 A | 10/1978 | Lafon |
| 2005/0148629 A1 | 7/2005 | Xiong |

FOREIGN PATENT DOCUMENTS

| EP | 1 707 560 A1 | 10/2006 |
| WO | WO 2005/027856 A2 | 3/2005 |

OTHER PUBLICATIONS

U.S. Appl. No. 12/011,888, filed Jan. 30, 2008, Johnson.
U.S. Appl. No. 12/011,847, filed Jan. 30, 2008, Johnson.
Xiong et al. The discovery of a potent and selective lethal factor inhibitor for adjunct therapy of anthrax infection. Bioorg. Med. Chem. Lett. 2006; 16, 964-8. Compound 40.
Alberts et al. Receptor Felxibility in de Novo Ligand Design and Docking. J. Med. Chem. 2005, 48, 6585-6596. See p. 6594, Compound 2.
Boukhris et al. Simple synthesis of hydroxamic acids and their conversion into a-hydroxy and a-amino acids.Tetrahedron Lett. 2000, 41, 2559-2562. See p. 2561,Compounds 3K,3r.

*Primary Examiner* — Bong-Sook Baek
(74) *Attorney, Agent, or Firm* — Knobbe Martens Olson & Bear LLP

(57) ABSTRACT

Compounds having the formula

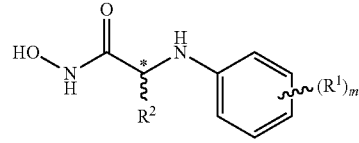

wherein the symbols have the meaning described in the specification are hydroxamic acid derivatives of aniline and capable of inhibiting the lethal effects of infection by anthrax bacteria and are useful in the treatment of poisoning by anthrax.

18 Claims, No Drawings

HYDROXAMIC ACID DERIVATIVES OF ANILINE USEFUL AS THERAPEUTIC AGENTS FOR TREATING ANTHRAX POISONING

CLAIM OF PRIORITY

The present application claims the priority of U.S. provisional application Ser. No. 60/898,988 filed on Feb. 1, 2007.

STATEMENT REGARDING FEDERALLY SPONSORED RESEARCH OR DEVELOPMENT

This invention was made with government support under Grant no. R44AI052587 awarded by the National Institutes of Health. The US government has certain rights in the invention.

BACKGROUND OF THE INVENTION

1. Field of the Invention

The present invention is directed to compounds useful for treatment of poisoning by *bacillus anthracis* (anthrax infection or poisoning). More particularly, the invention is directed to compounds capable of inhibiting the lethal effects of infection by anthrax bacteria and are useful in the treatment of poisoning by anthrax. The compounds of the invention are hydroxamic acid derivatives of aniline.

2. Background Art

Anthrax is a disease caused by infection of mammals, including humans, by *bacillus anthracis*. Spores of these bacteria can enter the mammalian, including human body, through skin abrasions, the digestive system or inhalation. Whereas anthrax poisoning in humans through skin abrasion or the digestive system can often be treated with antibiotics, anthrax poisoning in humans by ingestion of aerosol usually results in death of the infected individual.

Relatively recently, devices have been made which incorporate *bacillus anthracis* or its spores and are capable of releasing the bacteria or its spores in aerosol form. This "weaponized" form of anthrax can serve as a "weapon of mass destruction" in biological warfare and is feared in the Western World for its potential use by terrorists against civilian populations.

For all these reasons a serious effort has been made in the fields of medical and related biological research to elucidate the mode and agent of poisoning by *bacillus anthracis* and efforts have been made to synthesize compounds which act as inhibitors of the lethal toxins and therefore can treat the infection.

The following scientific publications describe or relate to the manner of infection by the bacteria and to elucidation of the toxic factors and their mode of action in the mammalian, including human body: Dixon et al. (1999) N. England J. Med. 341. 815-26; Mock et al. Annu. Rev. Microbiol. 55. 647-71; Vitalae et al. (1998) Biochem. Biopphys. Res. Commun. 248, 706-11; Vitalae et al. (2000) Biochem J. 352 Pt 3, 739-45; Duesbery et al. (1998) Science 280. 734-7; Duesbery et al. International Publication No. WO 99/50439; Hammond et al. (1998) Infect. Immun. 66, 2374-8. A summary of these findings is that the toxin, called "lethal factor", released by *bacillus anthraci* is an enzyme that splits an essential peptide needed by mammalian organisms for signal transmission. Thus, inhibitors of this bacterial enzyme are candidates for drugs for treatment of anthrax poisoning.

Published US Patent Application No. 2005/0148629 (Jul. 7, 2005) describes hydroxamic acid compounds which have the general formula shown below where the $R^1$ is aryl, or heteroaryl, or heterocyclic and where R represents a large number of potential substituents, including alkyl, and which can be used in the treatment of anthrax poisoning.

Published International Application WO 2005/027856 (Mar. 31, 2005) describe numerous compounds said to be inhibitors of anthrax lethal factor.

Published International Application WO 97/24117 discloses compounds of the general formula including some examples where the variable p=1, q=0 and m=1. Said compounds are said to be inhibitors of cyclic AMP phosphodiesterase.

The publication by Boukhris et al. Tetrahedron Letters 41 (2000) 2259-2562 disclose compounds of the following formulas $X = 4\text{-}CH_3C_6H_4$,
$X = 4\text{-}ClC_6H_4$,
$X = CH_3CH_2$ Published European Patent Application EP 1 707 560 A1 includes formulas 1 through 10 (pages 1-15) which purport to cover a very large number of compounds of diverging structures, some of which are pertinent to the compounds of the present invention.

The present invention represents a further advance in the field by providing hydroxamic acid derivatives of aniline which are useful to treat anthrax poisoning.

SUMMARY OF THE INVENTION

The present invention relates to compounds of Formula 1

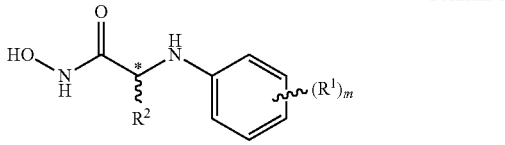

Formula 1 where $R^1$ is F, Cl, Br, I, alkyl of 1-3 carbons, alkoxy of 1-3 carbons, thioalkoxy of 1-3 carbons, phenyl, O-phenyl, CN, $CF_3$, $OCF_3$; OH, $NH_2$, $NHC_1$-$C_6$alkyl, $N(C_1$-$C_6alkyl)_2$, $CO_2H$ or $CO_2(C_1$-$C_6$ alkyl);

m is an integer having the value of 1 to 3;

$R^2$ is alkyl of 1-6 carbons; phenyl where phenyl is substituted with 0-3 $R^1$ groups, cyclohexyl, $C_1$-$C_8$alkylphenyl where phenyl is substituted with 0-3 $R^1$ groups, $C_1$-$C_8$alkylcyclohexyl, $(CH_2)_nOR^3$, $(CH_2)_nNHR^4$, $NR^4C_1$-$C_6$alkyl, $(CH_2)_nCF_3$, $CH_2OCH_2$phenyl where phenyl is substituted with 0-3 $R^1$ groups, $(CH_2)_nNH(CH_2)_nR^4$, $(CH_2)_nNR^6R^4$, $(CH_2)_nNR^6(CH_2)_nR^4$, $(CH_2)_nO(CH_2)_nR^4$, $(CH_2)_nOR^4$, or $R^2$ is $(CH_2)_n$N—($CH_2$-cyclohexyl)$_2$, or $R^2$ is $(CH_2)_n$N—($CH_2$-phenyl)$_2$ where phenyl is substituted with 0-3 $R^1$ groups, or $R^2$ is $(CH_2)_n$N—($CH_2$-heteroaryl)$_2$ where heteroaryl is substituted with 0-3 $R^1$ groups;

n is an integer having the value of 1 to 8;

$R^3$ is H, alkyl of 1 to 6 carbons, alkylphenyl where the alkylgroup has 1 to 6 carbons and the phenyl is substituted with 0-3 $R^1$ groups;

$R^4$ is H, alkyl of 1 to 9 carbons, cyclohexyl, $(CH_2)_p$cyclohexyl, C(O)alkyl of 1 to 4 carbons, C(O)alkylphenyl where the alkylgroup has 1 to 4 carbons and the phenyl is substituted with 0-3 $R^1$ groups or with a 5 to 6 membered heteroayl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $C(O)(CH_2)_pCOOH$, $(CH_2)_p$ phenyl where the phenyl is substituted with 0-3 $R^1$ groups or with 0-3 $R^1$ groups and a $NO_2$ group, or with 0-3 $R^1$ groups and an $OCH_2$phenyl group, or $R^4$ is $C(O)OC_1$-$C_6$alkyl, or $R^4$ is C(O)Ophenyl where the phenyl is substituted with 0-3 $R^1$ groups, or $R^4$ is $CH(CH_3)$phenyl where the phenyl is substituted with 0-3 $R^1$ groups, or $R^4$ is $C(O)(CH_2)_p$phenyl where the phenyl is substituted with 0-3 $R^1$ groups, or $R^4$ is C(O)CH$(Ph)_2$, C(O)—$CH_2$—(3PhO-)Ph, or $R^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $CH_2$heteroaryl where the heteroaryl group is 5 or 6 membered and has 1 to 2 heteroatoms selected from O, S, said heteroaryl group itself substituted with 0-3 $R^1$ groups, or $R^4$ is $CH_2$heteroaryl where the heteroaryl group is 5 or 6 membered and is condensed with a benzene ring has 1 to 2 heteroatoms selected from O, S and is substituted with 0-3 $R^1$ groups, or $R^4$ is $SO_2$-alkyl of 1 to 6 carbons, $SO_2$-Ph where the phenyl is substituted with 0-3 $R^1$ groups or with $NO_2$ or with $COOR^5$ group, or $R^4$ is C(O)NH-alkylphenyl, or C(O)NH-phenyl where the alkyl group has 1 to 4 carbons and where the phenyl is substituted with 0-3 $R^1$ groups;

p is an integer having the value of 0 to 4;

$R^5$ is alkyl of 1 to 6 carbons or phenyl substituted with 0-3 $R^1$ groups or with an OPh group;

$R^6$ is alkyl of 1 to 6 carbons;

the star indicates an asymmetric carbon, the wavy line represents a bond which can be of either R or S configuration, or a pharmaceutically acceptable salt of said compound.

The present invention also relates to pharmaceutical compositions suitable for administration to mammals, including humans, which include one or more compounds of the invention and are used for treatment or prevention of anthrax poisoning.

Biological Activity, Modes of Administration

Determining Biological Activity

As briefly noted above in the introductory section of this application for patent, the most serious, often lethal results of anthrax poisoning are caused by a toxin that is released by *bacillus anthracis* within the host. The toxin includes three proteins, one of which is a zinc-dependent metalloprotease enzyme (lethal factor) that cleaves near the N termini of several MAP kinase kinase enzymes (MKKS) of the host. It is this disruption of key signaling pathways mediated by the host MKK enzymes that result in the severe and often lethal results of infection by the bacteria.

An assay for identifying and measuring the effectiveness of potential drugs to treat anthrax poisoning is based on measuring the inhibitory effect of the candidate compound on the lethal factor enzyme. The procedure used in the present invention to measure the potential efficiency of the compounds of the present invention is based, in a somewhat modified form, on the assay described by Cummings et al., A peptide-based fluorescence resonance energy transfer assay for *Bacillus anthracis* lethal factor protease, PNAS, May 14, 2002, Vol 99, No. 10 6603-6606, expressly incorporated herein by reference. The gist of this assay that a fluorogenic peptide substrate is incubated with the lethal factor enzyme in the presence of the inhibitor and the inhibition of the lethal factor is measured by measuring the fluorescence intensity of the cleaved substrate. A description of the actual assay conditions used for evaluating the compounds of the present invention is provided below.

Assay Procedure

Inhibitors were solubilized in 100% DMSO at 10 mM, then diluted to the final desired concentration and 10% final DMSO in the assay. Lethal factor protease (20 nM) and inhibitor were briefly incubated at room temperature in the assay buffer (20 mM Hepes, 0.05% Tween 20, 0.02% $NaN_3$, pH 7.4), and the reaction started by the addition of 12.5 μM final of the fluorogenic peptide substrate, MAPKKide™ (List Biological Laboratories, Inc, Campbell, Calif.). The final volume was 50 μL, in half area black microtiter plates (Costar). Fluorescence intensity (Ex: 320 nm, Em: 420 nm) was monitored for 15 minutes at room temperature (Gemini XS, Molecular Devices), and the $K_i^{app}$ values were calculated using the program BatchKi (BioKin Ltd., Pullman, Wash.). Generally speaking a compound is considered active in this assay if the calculated $K_i^{app}$ value is less than 300 (<300) μM.

Modes of Administration

The compounds of the invention are useful for treating anthrax poisoning. The compounds of this invention may be administered systemically through oral, intravenous or other modes of systemic administration, depending on such considerations as the severity of the anthrax infection treated, quantity of drug to be administered, and numerous other considerations. For oral administration the drug may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate the compounds of the invention in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the anthrax infection being treated and the patient's susceptibility to treatment. Accordingly, no single concentration will be uniformly useful, but will require modification depending on the particularities of each situation. However, it is anticipated that an amount between 0.1 and 10 mg per kg of body weight per day will effect a therapeutic result.

Results of the Assay Measuring Lethal Factor Inhibitory Activity

Specific examples of compounds within the scope of the present invention are shown by their respective structural formulas in Tables 1 through 11, and their activity in the above-described assay is also indicated.

TABLE 1

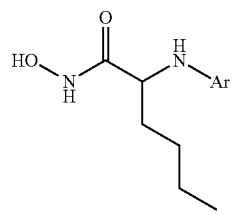

| Compound # | Ar | LF(FRET) $\overline{K_i^{app}(\mu M)}$ |
|---|---|---|
| 167210 | Ph— | 203 |
| 167291 | 2-F—Ph— | >300 |
| 167292 | 2-Me—Ph— | 273 |
| 167293 | 2-MeOPh— | >300 |
| 167277 | 3-F—Ph— | 133.8 |
| 167170 | 3-Me—Ph— | 34.1 |
| 167257 | 3-Cl—Ph— | 61.5 |
| 167201 | 3-Et—Ph— | 89.8 |
| 167276 | 3-MeO—Ph— | 140.5 |
| 167183 | 3-i-Pr—Ph— | >300 |
| 167202 | 3-Ph—Ph— | 236 |
| 167211 | 4-F—Ph— | 81 |
| 167255 | 4-Me—Ph— | 296 |
| 167256 | 4-Cl—Ph— | 187 |
| 167275 | 4-MeO—Ph— | 88.1 |
| 167162 | 3-Me-4-F—Ph— | 2.0 |
| 167324 | 3-Me-4-MeO—Ph— | 19.3 |
| 167322 | 3-Cl-4-F—Ph— | 17.1 |
| 167226 | 3,5-diMe—Ph— | 7.4 |
| 167645 | 3-Cl-5-Me—Ph | 2.2 |
| 167455 | 2,4-diMe-3-F—Ph | 88.1 |
| 167454 | 3,5-diMe-4-F—Ph— | 0.8 |
| 167325 | 3,5-diMe-4-MeOPh— | 30.4 |

TABLE 2

3,5-dimethyl-4-fluoroanilines derived from R-amino acids

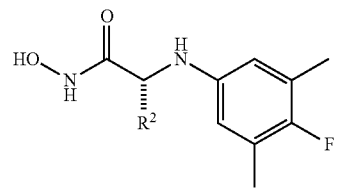

| Compound # | R² | LF(FRET) $\overline{K_i^{app}(\mu M)}$ |
|---|---|---|
| 167452 | —H | 4.0 |
| 167497 | —CH₃ | 0.47 |
| 167450 | —Et | 0.67 |
| 167391 | —Pr | 0.50 |
| 167264 | -i-Pr | 3.1 |
| 167294 | -n-Bu | 0.52 |
| 167402 | -i-Bu | 0.67 |
| 167425 | —Ph | 0.48 |
| 167424 | -cC6 | 0.79 |
| 167378 | —CH₂Ph | 7.0 |
| 167405 | —CH₂cC6 | 1.48 |
| 167406 | —CH₂CH₂Ph | 0.51 |
| 167485 | —CH₂OH | 0.59 |
| 167484 | —CH₂Ot-Bu | 0.45 |
| 167379 | —CH₂OCH₂Ph | 1.44 | cC6 = cyclohexyl

TABLE 3

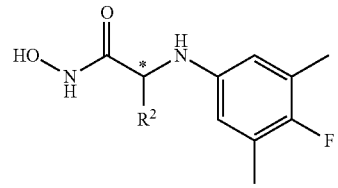

| Compound # | Config(*) | R² | LF(FRET) $\overline{K_i^{app}(\mu M)}$ |
|---|---|---|---|
| 167498 | S | Me | 51 |
| 167296 | S | i-Pr | 201 |
| 167295 | S | n-Bu | 106 |
| 167486 | R,S | Me | 0.69 |
| 167482 | R,S | —CH₂CH₂CF₃ | 1.1 |
| 167483 | R,S | —CH₂CH₂CH₂CF₃ | 1.3 |

TABLE 4

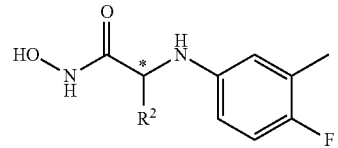

| Compound # | Configuration(*) | R² | LF(FRET) $\overline{K_i^{app}(\mu M)}$ |
|---|---|---|---|
| 166986 | — | H | 7.6 |
| 167235 | R,S | Me | 1.4 |
| 167228 | R,S | Ph | 2.8 |
| 167233 | R,S | —CH₂C₆H₄-4-OCF₃ | 102 |
| 167392 | R | Me | 0.96 |
| 167267 | R | i-Pr | 15.7 |

TABLE 4-continued

Compound structure: hydroxamic acid with NH-Ar (3-methyl-4-fluorophenyl), R² substituent at * carbon.

| Compound # | Configuration(*) | R² | LF(FRET) $\overline{K_i^{app}(\mu M)}$ |
|---|---|---|---|
| 167273 | R | n-Bu | 0.71 |
| 167364 | S | Me | 87 |
| 167268 | S | i-Pr | >300 |
| 167274 | S | n-Bu | 116 |

TABLE 5

3,5-dimethyl-4-fluoroanilines derived from R-lysine

| Compound # | R | LF(FRET) $\overline{K_i^{app}(\mu M)}$ |
|---|---|---|
| 167517 | —NH₂ | 0.25 |
| 167552 | —NHAc | 2.53 |
| 167587 | —NHC(O)—Ph | 0.97 |
| 167551 | —NHC(O)—3Me-4F—Ph | 0.39 |
| 167588 | NHC(O)—CH₂Ph | 1.20 |
| 167610 | —NHC(O)CH(Ph)₂ | 1.34 |
| 167611 | —HC(O)CH₂—(3-PhO)Ph | 0.74 |
| 167592 | —NHC(O)CH₂-4-(2,5-diMe-pyrroll-yl)-Ph | 1.44 |
| 167620 | —NHC(O)CH₂CH₂CO₂H | 3.5 |
| 167654 | —NHCH₂—3Me-4F—Ph | 0.10 |
| 167605 | 2,5-diMe-pyrrol-1-yl | 2.0 |
| 167531 | —NHSO₂Me | 1.0 |
| 167615 | —NHSO₂Ph | 0.84 |
| 167622 | —NHSO₂-3-NO₂—Ph | 0.15 |
| 167621 | —NHSO₂-3-CO₂H—Ph | 1.57 |
| 167589 | —NHSO₂-4-F—Ph | 1.25 |
| 167656 | —NHSO₂-4-NH₂—Ph | 0.61 |
| 167657 | —NHSO₂-4-MeNH—Ph | 0.41 |
| 167590 | —NHSO₂-3-Me-4-F—Ph | 0.25 |
| 167530 | —NHSO₂-3,5diMe-4-F—Ph | 0.37 |
| 167613 | —NHSO₂-4-CO₂H—Ph | 3.66 |
| 167561 | —NHC(O)OtBu | 0.71 |
| 167503 | —NHC(O)OCH₂Ph | 0.29 |
| 167614 | —NHC(O)NHCH₂—3Me-4F—Ph | 0.28 |

TABLE 6

| Compound # | Ar | LF(FRET) $\overline{K_i^{app}(\mu M)}$ |
|---|---|---|
| 167719 | 3-CN—Ph | 49.0 |
| 167720 | 3-CN-4-F—Ph— | 11.8 |
| 167793 | 3-MeO-4-F—Ph— | 157.0 |
| 167807 | 3,5-diF—Ph— | 228.0 |
| 167722 | 3-F-5-Me—Ph— | 19.0 |
| 167844 | 3-Br-5-Me—Ph— | 3.5 |
| 167718 | 3,5-diCl—Ph | 12.2 |
| 167843 | 3,5-diBr—Ph— | 52.3 |
| 167772 | 3,5-diMeO—Ph— | 257.5 |

TABLE 7

| Compound # | R | LF(FRET) $\overline{K_i^{app}(\mu M)}$ |
|---|---|---|
| 167736 | —CH₂—Ph | 0.11 |
| 167698 | —CH₂-3Me—Ph | 0.16 |
| 167737 | —CH₂-3NO₂—Ph | 0.07 |
| 168030 | —CH₂-4F—Ph | 0.004 |
| 167759 | —CH₂-3,5-diMe-4F—Ph | 0.07 |
| 167667 | —SO₂-3-MeNH—Ph | 0.59 |
| 167700 | —SO₂-3-diMeN—Ph | 0.88 |
| 167699 | —SO₂-4-diMeN—Ph | 0.43 |

TABLE 8

| Compound # | R | LF(FRET) $\overline{K_i^{app}(\mu M)}$ |
|---|---|---|
| 167949 | H | 0.20 |
| 167926 | —C(O)OtBu | 2.9 |
| 168167 | 2-propyl-pentyl | 0.25 |
| 168146 | —CH₂-cyclohexyl | 0.25 |
| 167980 | —CH₂—Ph | 0.15 |
| 167945 | —CH₂-4F—Ph | 0.03 |
| 168181 | —CH₂-4Cl—Ph | 0.19 |

TABLE 8-continued

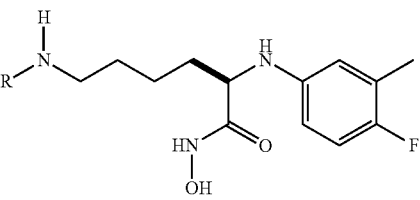

| Compound # | R | LF(FRET) $\overline{K_i^{app}(\mu M)}$ |
|---|---|---|
| 168165 | —CH$_2$-3-biphenyl | 0.12 |
| 167990 | —CH$_2$-3,4-diF—Ph | 0.10 |
| 167946 | —CH$_2$—3Me-4F—Ph | 0.06 |
| 167968 | —CH$_2$-3,5-diMe-4F—Ph | 0.10 |
| 167969 | —CH$_2$-1,5-diMe-4-(OCH$_2$Ph)—Ph | 0.27 |
| 168010 | —CH(Me)-4F—Ph | 0.07 |
| 167979 | —CH$_2$CH$_2$—Ph | 0.21 |
| 167978 | —CH$_2$-5-(2-F-pyridyl) | 0.26 |
| 168008 | —CH$_2$-2-(5-Cl-thienyl) | 0.06 |
| 168168 | —CH$_2$-2-pyrazinyl | 0.63 |
| 168166 | —CH$_2$-2-benzo[b]furyl | 0.18 |
| 168182 | —CH$_2$-5-benzo[b]thienyl | 0.15 |
| 168145 | —CH$_2$-5-benzo[1,3]dioxolyl | 0.17 |
| 167993 | —C(O)CH$_2$CH$_2$—Ph | 0.88 |
| 167994 | —C(O)—(CH$_2$)$_3$—Ph | 0.65 |

TABLE 9

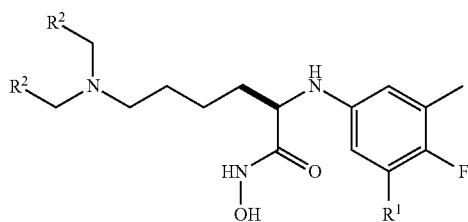

| Compound # | R$^1$ | R$^2$ | LF(FRET) $\overline{K_i^{app}(\mu M)}$ |
|---|---|---|---|
| 167982 | H | Ph— | 1.8 |
| 167963 | H | 4-F—Ph— | 1.1 |
| 168080 | H | 5-(2-F-pyridyl) | 10.6 |
| 167966 | H | 3-Me-4-F—Ph— | 6.7 |
| 167971 | H | 3,5-diMe-4-F—Ph— | 5.2 |
| 167991 | H | Cyclohexyl- | 16.6 |
| 167738 | Me | Ph— | 0.43 |
| 167932 | Me | 3-Me—Ph— | 1.1 |
| 168047 | Me | 4-F—Ph | 0.79 |
| 167933 | Me | 3,5-diMe-4-F—Ph— | 1.9 |

TABLE 10

| Compound | Y | LF(FRET) $\overline{K_i^{app}(\mu M)}$ |
|---|---|---|
| 168116 | O | 0.71 |
| 168118 | CH$_2$ | 7.2 |

TABLE 11

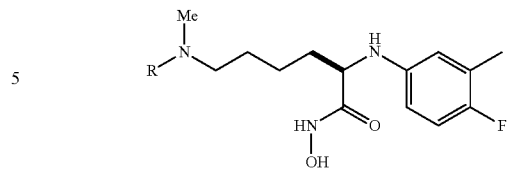

| PT | R | LF(FRET) $\overline{K_i^{app} \mu M)}$ |
|---|---|---|
| 168147 | —CH$_2$-4-F—Ph | 0.19 |

General Embodiments and Synthetic Methodology

Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid or an amino functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers, pure enantiomers (optical isomers) and 50:50 (racemic) or other ratio mixtures of enantiomers as well. In some cases one compound of a diastereomeric species, or one specific enantiomer of a chiral compound is more active than the other diastereomer(s) or optical isomer, and when such a case is established it is indicated in the respective designation of the compound.

General Synthetic Methodology

The novel compounds used in accordance with the invention are encompassed by the general Formula 1 provided above and or by the claims originally submitted in the present application.

A general route for the synthesis of the compounds of Formula 1 are shown in the General Schemes 1-3, below.

Referring now to General Scheme 1 an alpha-bromo carboxylic acid ester and a substituted aniline serve as starting materials. The variables $R^1$, m and $R^2$ are as defined in Formula 1. (Generally speaking throughout the description of the reaction schemes the variables shown in the schemes are defined as in Formula 1.) Such starting materials are either available commercially or can be obtained in accordance with known chemical scientific and or patent literature or by such modifications of known synthetic procedures which will be readily apparent to those skilled in the art. The alpha-bromo carboxylic acid ester and the substituted aniline are reacted in a suitable solvent, such as dimethylformamide (DMF) in the presence of an acid acceptor, such as potassium carbonate to give the compound shown in the scheme as Intermediate Formula 1. The latter compound is converted into the hydroxamic acid compounds of the invention by treatment with potassium cyanide (KCN) and hydroxylamine ($NH_2OH$—$H_2O$) in the presence of a suitable solvent or solvent mixture, such as tetrahydrofuran (THF) and methanol (MeOH).

An alternative synthetic route to compounds of the invention is shown in General Scheme 2. In accordance with this scheme an alpha amino acid, such as for example any of the naturally occurring amino acids or their dextrorotatory enantiomer is reacted with a substituted bromo benzene. Both of these starting materials are either available commercially or can be readily obtained by a person of ordinary skill in the art by reference to known chemical literature. The alpha amino acid and the substituted bromobenzene are reacted in the presence of cuprous iodide (CuI in the presence of an acid acceptor, such as potassium carbonate, in a suitable solvent, such as dimethyl formamide to give the compound shown as Intermediate Formula 2. Intermediate Formula 2 is treated with O-tert butyl-hydroxylamine in the presence of 1-hydroxybenzotriazole (HOBt), N-methylmorpholine (NMM), N-(dimethylaminopropyl)-N'-ethylcarbodiimide (EDC) in a solvent, such as dichloromethane (DCM) to give the O-tert-butyl derivative of the desired hydroxamic acids of Formula 1 (Intermediate Formula 3). The latter compound is treated with trifluoroacetic acid (TFA) in dichloromethane to give compounds of Formula 1.

General Scheme 3 discloses still another synthetic route to the compounds of Formula 1. In accordance with this scheme a simple ester, such as a methyl ester of an alpha amino acid (see Scheme 2) and a substituted phenyl boronic acid are the starting materials. The latter is either available commercially, or depending on the nature of the $R^1$ can be obtained in accordance with the chemical literature. These starting materials are reacted in the presence copper acetate ($Cu(OAc)_2$), triethylamine ($Et_3N$) and molecular sieve (4 angstrom) in a solvent, such as dichloromethane to provide the ester compound, Intermediate Formula 1. The Intermediate Formula 1 is converted into compounds of the invention of Formula 1 by the same reagents as in General Scheme 1.

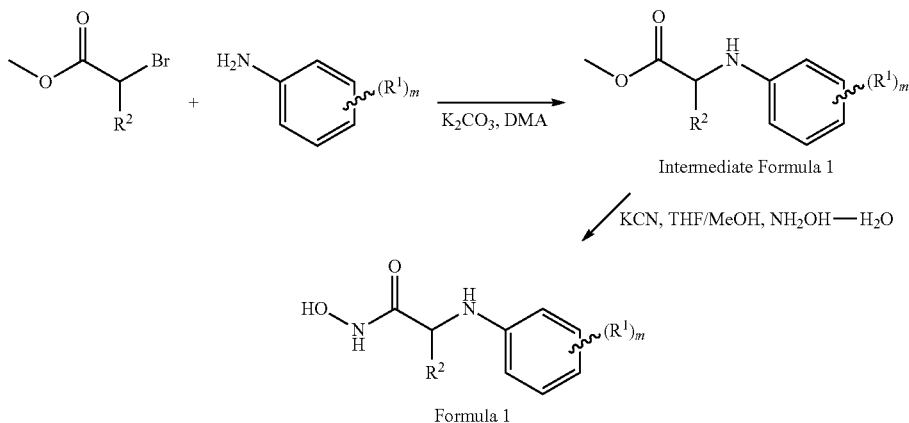

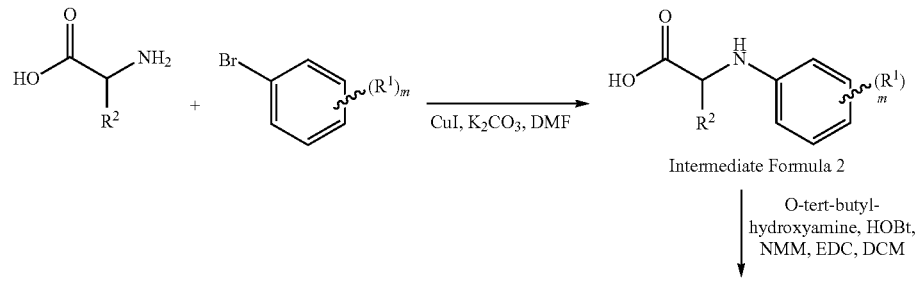

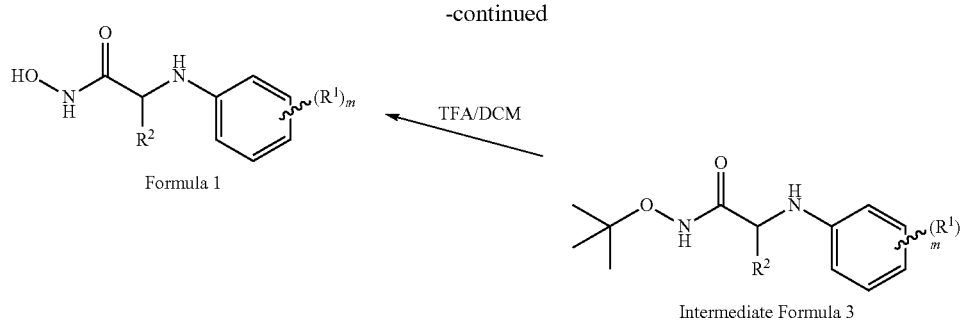

Formula 1

Intermediate Formula 3

General Synthetic Scheme 3

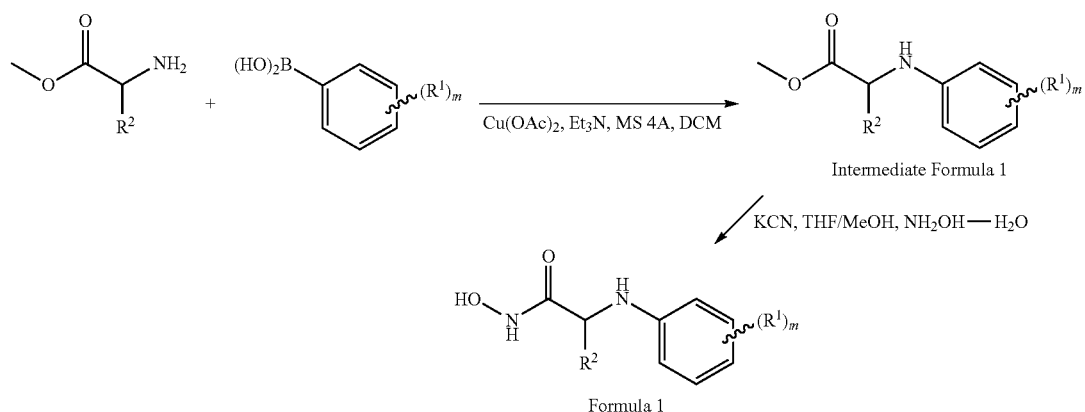

Intermediate Formula 1

Formula 1

General Reaction Scheme 4 discloses a synthetic route to that particular class of the compounds of the invention which are shown in Table 5 above. In this synthetic route a simple ester (such as a methyl ester) of a t-butyloxycarbonyl (Boc) protected alpha, omega amino acid is reacted with the substituted phenylboronic acid (see Scheme 3) under the same conditions as is disclosed for the analogous reaction in Scheme 3 above to give the compound shown as Intermediate Formula 4. The Boc-protected alpha, omega amino acid ester is either available commercially or can be prepared in accordance with the chemical literature. The Boc protecting group is removed from the terminal amino group of Intermediate Formula 4 by treatment with trifluoroacetic acid (TFA) to provide Intermediate Formula 5 that has a terminal free amino group. Intermediate Formula 5 is then reacted with a sulfonyl chloride in the presence of triethylamine in an aprotic solvent such as dichloromethane to give the Intermediate Formula 6. This reaction scheme shows a substituted phenylsulfonyl chloride, however it should be understood that this reaction could also be carried out with other sulfonyl chlorides, such as for example an alkyl sulfonyl chloride or a substituted pyrrol-yl or other heteroaryl sulfonyl chloride. The ester compound of Intermediate Formula 6 is then reacted with potassium cyanide (KCN) and hydroxylamine (NH$_2$OH—H$_2$O) under the conditions shown for the analogous reaction in General Scheme 1 to yield compounds of Formula 2, which are a subgenus of the compounds of Formula 1.

The Intermediate Formula 5 can also be converted into the corresponding amide and urea derivatives, as is shown in the continuation part of Reaction Scheme 4. In this conversion Intermediate Formula 5 is reacted with an acyl chloride, such as phenylacetic acid chloride, to provide Intermediate Formula 7. Intermediate Formula 7 is then reacted with potassium cyanide (KCN) and hydroxylamine (NH$_2$OH—H$_2$O) under the conditions shown for the analogous reaction in General Scheme 1 to yield compounds of Formula 3. Referring still to the first continuation of General Synthetic Scheme 4, Intermediate Formula 5 is reacted with and isocyanate in suitable solvent such as acetonitrile to give Intermediate Formula 8. Intermediate Formula 8 is then reacted with potassium cyanide (KCN) and hydroxylamine (NH$_2$OH—H$_2$O) under the conditions shown for the analogous reaction in General Scheme 1 to yield compounds of Formula 4.

Referring now to the second continuation of Reaction Scheme 4, Intermediate Formula 5 is reacted with an aldehyde, such as phenylacetaldehyde to give a Schiff base (not specifically shown in the scheme) that is reduced to give Intermediate Formula 9. The ester function of Intermediate Formula 9 is converted into the hydroxamic acid function of Formula 5 by treatment with potassium cyanide (KCN) and hydroxylamine (NH$_2$OH—H$_2$O). Intermediate Formula 9 can also be obtained from Intermediate Formula 7 by reduction with a suitable reducing agent, such as diborane.

The compounds of Formula 3, Formula 4, and of Formula 5 are within the scope of the invention and represent subgenus of Formula 1.

General Synthetic Scheme 4
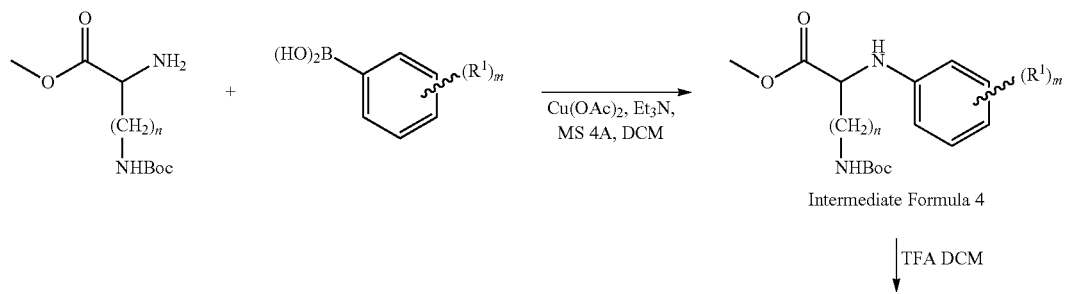
Intermediate Formula 4
↓ TFA DCM
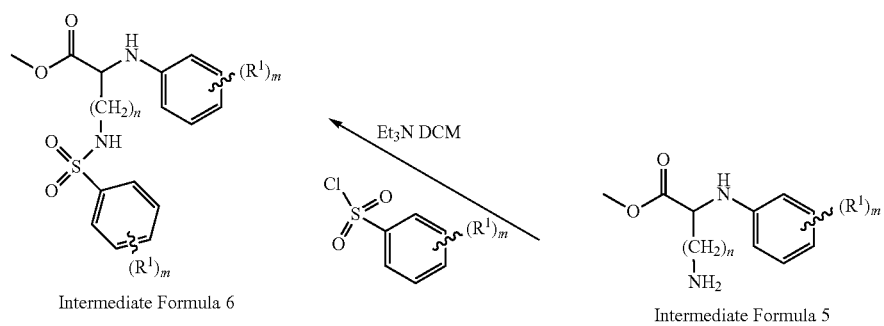
Intermediate Formula 6 ← Et₃N DCM — Intermediate Formula 5
↓ KCN, THF/MeOH, NH₂OH—H₂O
Formula 2
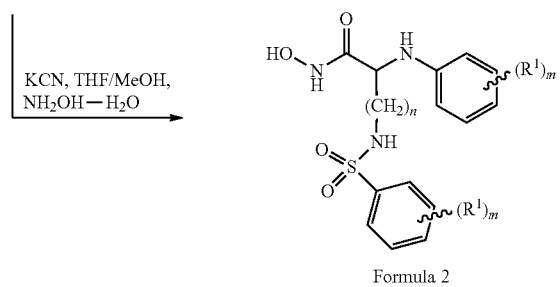
Intermediate Formula 5
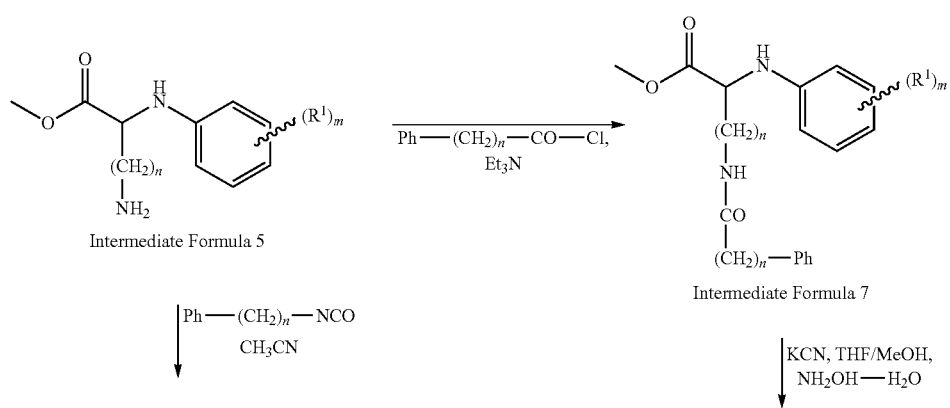
Intermediate Formula 7
↓ Ph—(CH₂)ₙ—NCO    CH₃CN
↓ KCN, THF/MeOH, NH₂OH—H₂O -continued
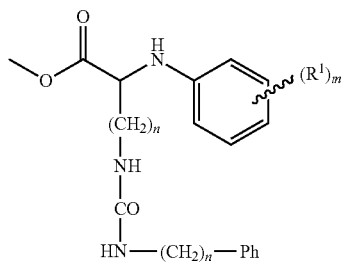
Intermediate Formula 8
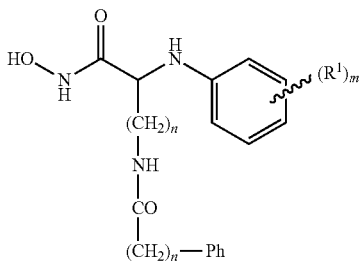
Formula 3
KCN, THF/MeOH,
NH$_2$OH—H$_2$O
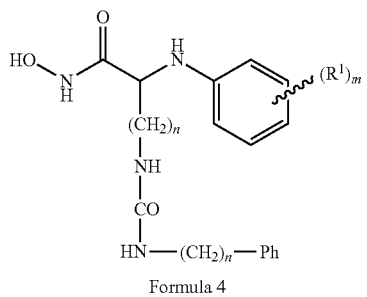
Formula 4
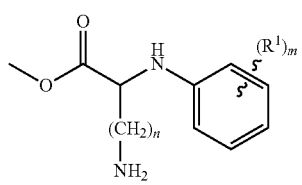
Intermediate Formula 5
Ph—(CH$_2$)$_n$—CO—Cl,
Et$_3$N
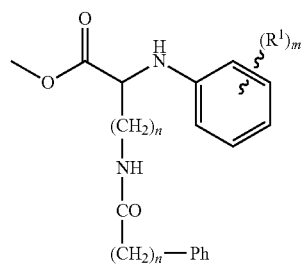
Intermediate Formula 7
Ph(CH$_2$)$_n$—CHO
NaBH(OAc)$_3$
THF/HOAc
B$_2$H$_6$
THF
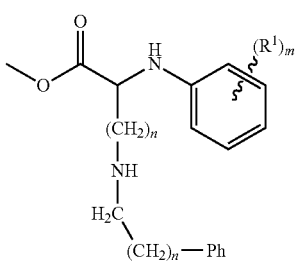
Intermediate Formula 9
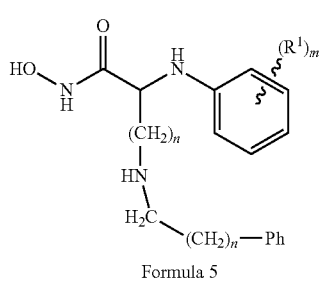
Formula 5
KCN, THF/MeOH,
NH$_2$OH—H$_2$O General Synthetic Scheme 5 discloses a synthetic route to that particular class of compounds of the invention which are shown in Table 10 and where the variable Y in the Table is O. One starting material in this scheme is a lactone of an omega hydroxyl alkanoic acid. The variable n for this starting material has the same definition as in connection with Formula 1 with the restriction that the starting material must be able to form a cyclic lactone. The other starting material is a substituted bromobenzene where the variables $R^1$ and m have the same definition as in connection with Formula 1. These starting materials are reacted in the presence of strong base, such as KOH in a suitable solvent, such as toluene to provide the Intermediate of Formula 8. The Intermediate of Formula 8 is then reacted with (R)-4-benzyloxazolidin-2-one in the presence of triethylamine, pivaloyl chloride and LiCl in an aprotic solvent, such as THF, to give the Intermediate of Formula 9. Reaction of the Intermediate of Formula 9 with 2,4,6-triisopropylbenzenesulfonyl azide (trisyl azide) in the presence of potassium bis(trimethylsilyl)amide (KHMDS), with THF serving as a solvent yields the Intermediate of Formula 10 after treatment with acetic acid. The Intermediate of Formula 10 is reacted with a strong base, such as LiOH and hydrogen peroxide to give the free carboxylic acid of Intermediate of Formula 11. The Intermediate of Formula 11 is esterified by treatment with trimethylsilyldiazomethane ($TMSCH_2N_2$) in a suitable solvent, such as a mixture of methanol with dichloromethane (DCM) to give the ester compound of Intermediate of Formula 12. The azide function of the Intermediate of Formula 12 is reduced by catalytic hydrogenation to yield the alpha amino carboxylic acid ester of Intermediate of Formula 13. The Intermediate of Formula 13 is reacted with a substituted phenyl boronic acid (where the variables $R^1$ and m have the same definition as in connection with Formula 1) in the presence of copper(II)acetate, triethylamine, 4 angstrom molecular sieve (MS), in dichloromethane under an oxygen atmosphere to give the Intermediate of Formula 14. The Intermediate of Formula 14 is converted into the hydroxamic acid compounds of the invention (Formula 6) by treatment with potassium cyanide (KCN) and hydroxylamine ($NH_2OH$—$H_2O$) in the presence of a suitable solvent or solvent mixture, such as tetrahydrofuran (THF) and methanol (MeOH). The compounds of Formula 6 represent a subgenus of the compounds of Formula 1.

General Synthetic Scheme 5

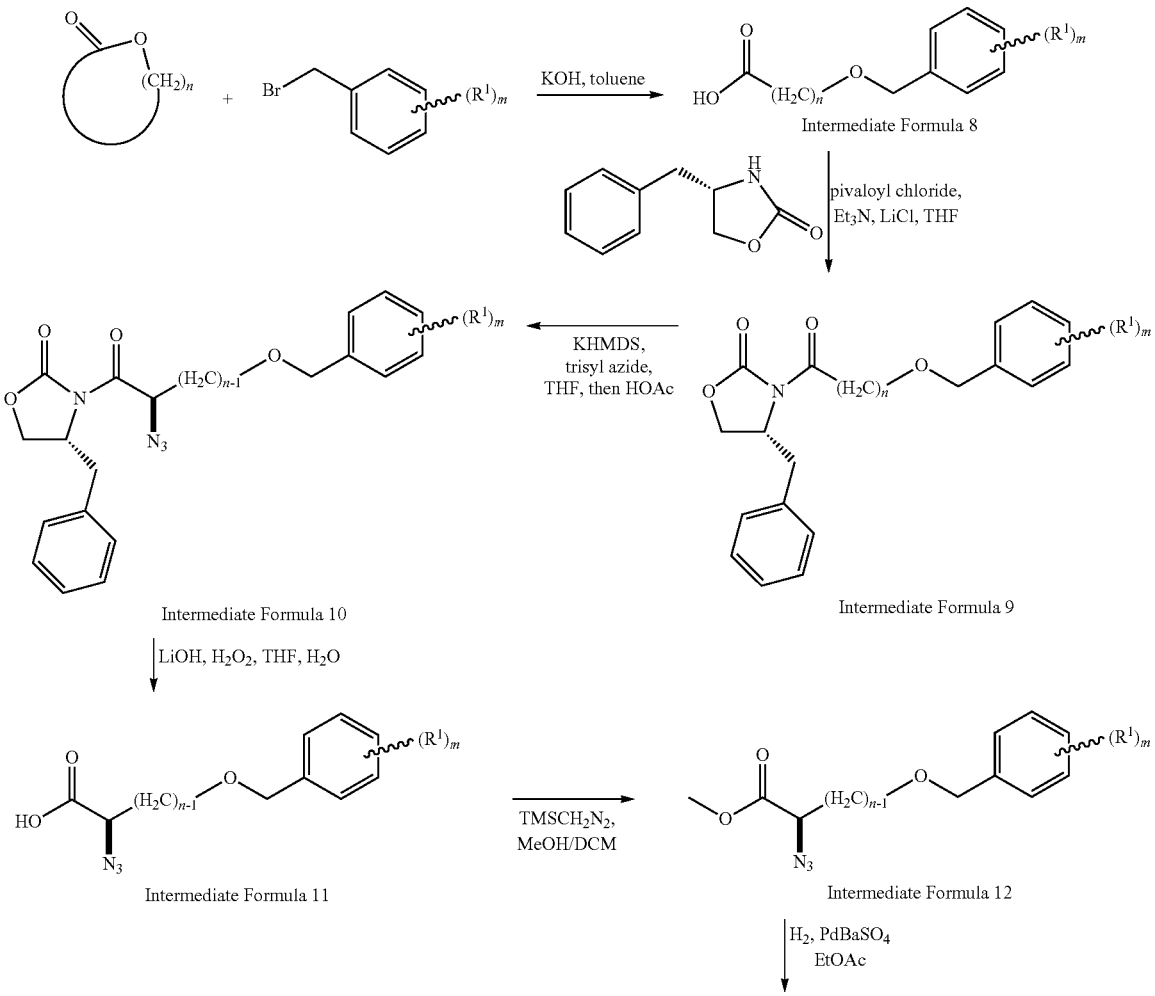

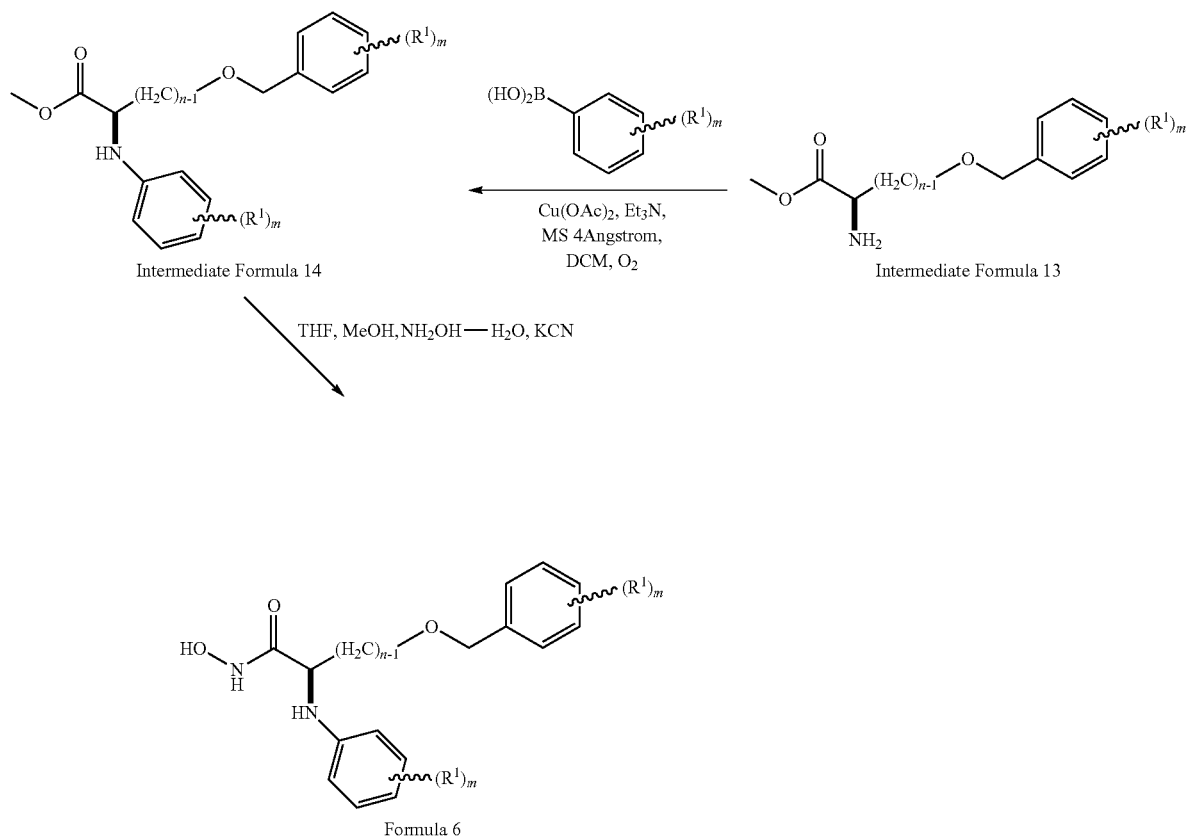

General Synthetic Scheme 6 discloses a synthetic route to that particular class of compounds of the invention which are shown in Table 10 and where the variable Y in the Table is $CH_2$. In this reaction scheme the starting material is an omega bromo alkanoic acid where the variable n has the same definition as in connection with Formula 1. The omega bromo alkanoic acid is reacted with triphenylphosphine ($PPh_3$) in a suitable solvent, such as toluene, to provide the Intermediate Formula 15. The Intermediate Formula 15 is then reacted in a Wittig reaction with a substituted benzaldehyde to provide the Intermediate Formula 16. The variables $R^1$ and m in the formula of the substituted benzaldehyde are defined as in connection with Formula 1. The olefinic double bond of the Intermediate Formula 16 is reduced by catalytic hydrogenation to the carboxylic acid compound Intermediate Formula 17. The Intermediate Formula 17 is reacted with (R)-4-isopropyloxazolidin-2-one in the presence of triethylamine, pivaloyl chloride and LiCl in an aprotic solvent, such as THF, to give the Intermediate Formula 18. The Intermediate Formula 18 is then subjected to a series of reactions which are substantially identical to the reaction to which the Intermediate Formula 10 is subjected in accordance with General Scheme 5 to yield the compounds of Formula 7. The compounds of Formula 7 represent a subgenus of the compounds of Formula 1.

General Synthetic Scheme 6

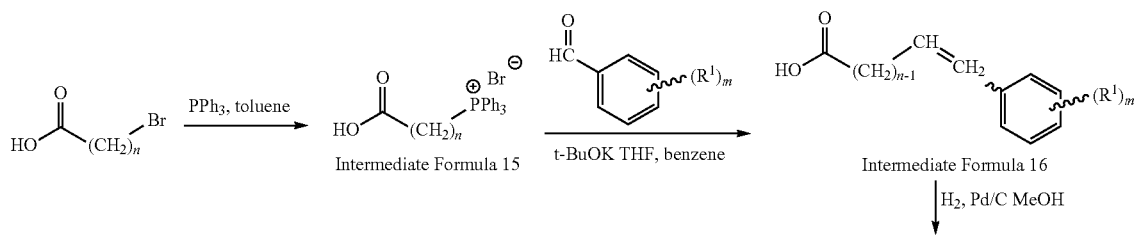

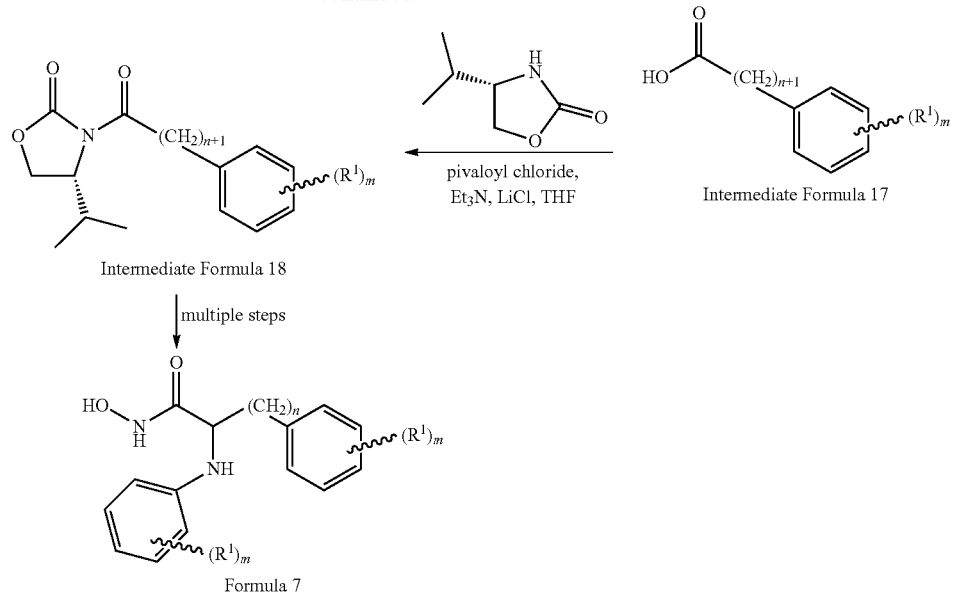

Formula 7

PREFERRED EXAMPLES

Referring now to the variable $R^1$ in Formula 1, in the compounds of the invention $R^1$ represents a substituent on the phenyl group shown in the formula. In the preferred compounds of the invention $R^1$ is F, Cl, Br, CN, methyl, or methoxy. The variable m is preferably the integer selected from 1, 2 and 3. Even more preferably the variable m is 2 or 3. Particularly preferred are compounds of the invention where m is 2, and the $R^1$ are methyl and fluoro, with the methyl group being in the 3 (meta) position and the fluoro being in the 4 (para) position relative to the NH group. Also particularly preferred are compounds where m is 3, and there is a methyl group in the 3,5 (meta, meta) positions and a fluoro in the 4 (para) position of the phenyl ring.

Referring now to the variable $R^2$ in Formula 1 in the preferred compounds of the invention $R^2$ is alkyl of 1 to 4 carbons, cyclohexyl, phenyl, alkylphenyl where the alkyl group has 1 to 3 carbons, $CH_2OCH_2$-phenyl, $(CH_2)_nCF_3$ where n is 2 or 3, $CH_2OR^3$ where $R^3$ is H, or t-butyl. In certain preferred compounds $R^2$ is H. In the preferred compounds of this group the phenyl group, where applicable, is either unsubstituted or has only a single substituent selected from the preferred $R^1$ groups.

Compounds of the invention are also preferred where the variable $R^2$ is $(CH_2)_nNHR^4$ where n is the integer 3, 4 or 5 and $R^4$ is H, $C(O)CH_3$, $C(O)O(CH_2)_nCH_3$, alkylpyridyl, alkylthienyl, alkylpyrazinyl, alkylbenzo[b]furanyl, alkylbenzo[b]thienyl, alkylphenyl, C(O) substituted phenyl, where the pyridyl, thienyl pyrazinyl, benzo[b]furanyl, benzo[b]thienyl, and phenyl groups are substituted with the preferred examples of the $R^1$ group or with a phenoxy group, $C(O)CH_2$-phenyl, $CH(phenyl)_2$, $C(O)(CH_2)_2COOH$, dimethyl substituted pyrrolyl, $SO_2$alkyl of 1 to 3 carbons, $SO_2$-phenyl where the phenyl is substituted with the preferred examples of $R^1$ or with a nitro ($NO_2$) group. Still preferred are compounds where $R^4$ is C(O)NH-alkylphenyl where the alkyl group has 1 to 4 carbons and the phenyl group is substituted with the preferred examples of the $R^1$ group. Further preferred are compounds where the $R^2$ group is $(CH_2)_n$-disubstitited amino as defined in Table 9, $(CH_2)_n$Oalkylphenyl or $(CH_2)_n$phenyl where the phenyl group is substituted with the preferred $R^1$ substituents.

The most preferred compounds of the invention are shown in Tables 1 through 11 above, and are also shown and disclosed below with their characteristic data such as NMR, mass spectrometry, and optical rotation, as applicable.

EXPERIMENTAL

Schemes and experimental descriptions for the synthesis of the specific exemplary compounds of the invention are provided below. The LC/MS data given was obtained using the following conditions: LC/MSD/ELSD analysis performed in ESI positive mode with an Agilent 1100 LC/MSD VL system equipped with Agilent 1100 HP PDA and Sedex 75 ELSD detectors. Column: Zorbax Eclipse SD-C18, 5 μm, 4.6×75 mm; Temperature set at 25° C.; Mobile Phase: % A=0.025% trifluoroacetic acid-water, % B=0.025% trifluoroacetic acid-acetonitrile; or % A=0.10 formic acid-water, % B=0.10 formic acid-acetonitrile Linear Gradient: 20%-98% B in 15 min.; Flow rate: 1.0 mL/min.; ELSD gain set @ 3; UV set at 254 nm and 214 nm.

Specific Scheme 1

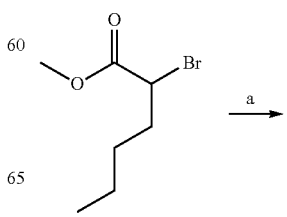

25
-continued

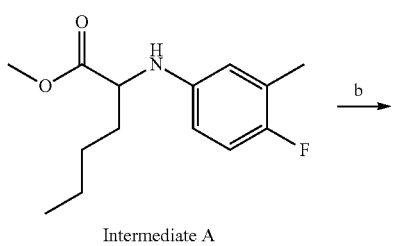

Intermediate A

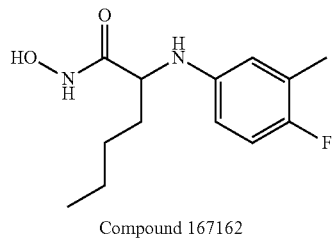

Compound 167162

Reagents and conditions: (a) 1 eq of 4-fluoro-3-methylaniline, 5 eq of K₂CO₃, DMF, rt; (b) KCN (5 mol %), THF/MeOH/50% NH₂OH—H₂O (2:2:1), rt.

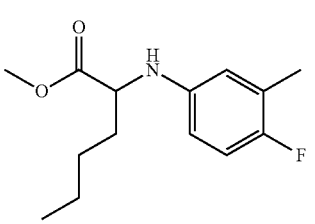

2-(4-Fluoro-3-methyl-phenylamino)-hexanoic acid methyl ester (Intermediate A)

To a solution of 2-bromo-hexanoic acid methyl ester (0.500 g, 2.404 mmol) and 4-fluoro-3-methylaniline (0.301 g, 2.404 mmol) in 15 mL of DMF, was added K₂CO₃ (1.661 g, 12.020 mmol). After stirring at room temperature under N₂ for 88 h, the reaction mixture was diluted with 60 mL of water and extracted with dichloromethane (60 mL×3). The organic extracts were combined dried over anhydrous Na₂SO₄ and the solvent removed under reduced pressure. Flash chromatography (silica gel) eluting with 0-20% ethyl acetate/hexanes afforded the title compound as brown oil (0.273 g, 45% yield). LC-MS: $t_R$=9.9 min; m/z 254 (M+H)⁺.

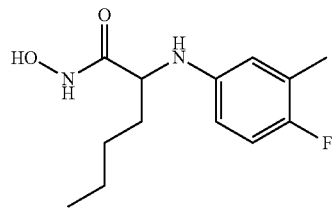

26
2-(4-Fluoro-3-methyl-phenylamino)-hexanoic acid hydroxyamide (Compound 167162)

To a solution of 2-(4-fluoro-3-methyl-phenylamino)-hexanoic acid methyl ester (0.273 g, 1.078 mmol) in 5 mL of THF/MeOH/50% NH₂OH—H₂O (2:2:1), was added KCN (0.004 g, 0.054 mmol). After stirring at room temperature for 15 h, the reaction mixture was diluted with 60 mL of water and extracted with ethyl acetate (60 mL×3). The combined organic extracts were dried over anhydrous Na₂SO₄ and concentrated under reduced pressure. The product was isolated by Flash chromatography (silica gel) eluting with 0-10% methanol/dichloromethane to give the title compound as an off-white solid (0.129 g, 47% yield). LC-MS: $t_R$=6.0 min, m/z 255 (M+H)⁺; ¹H NMR (500 MHz, CD₃OD) δ 0.93 (t, J=7.05 Hz, 3H), 1.35-1.44 (m, 4H), 1.78-1.87 (m, 2H), 2.21 (d, J=1.50 Hz, 3H), 3.74 (dd, J=7.55, 6.54 Hz, 1H), 6.74-6.77 (m, 1H), 6.81 (dd, J=6.21, 2.52 Hz, 1H), 6.93 (t, J=9.06 Hz, 1H); ¹³C NMR (125.75 MHz, CD₃OD) δ 14.17, 14.62, 23.44, 28.86, 33.04, 60.94, 116.60 (d, J=23.77 Hz), 117.24 (d, J=7.29 Hz), 121.22, 126.99 (d, J=18.23 Hz), 139.76, 158.63 (d, J=238.55 Hz), 170.24; ¹⁹F NMR (470.58 MHz, CD₃OD) δ −132.90.

Specific Scheme 2

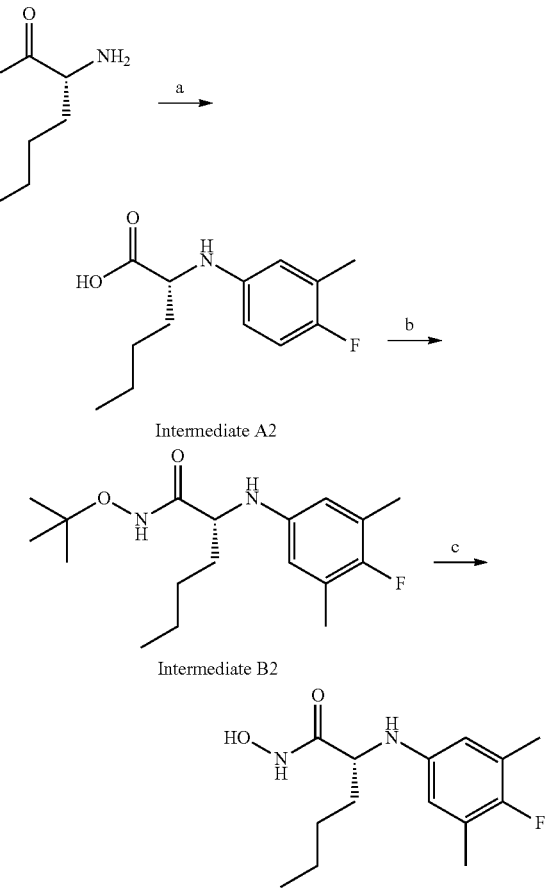

Compound 167294

Reagents and conditions: (a) 1 eq of 5-bromo-2-fluoro-1,3-dimethyl-benzene, 10 mol % of CuI, 1.5 eq. of K₂CO₃, DMA, 90° C.; (b) 3 eq of O-tert-butyl-hydroxyamine, 1 eq of HOBT, 5 eq of NMM, 1.5 eq of EDC, DCM, rt; (c) TFA/DCM (1:1), rt.

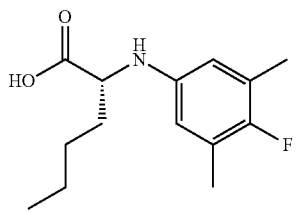

(R)-2-(4-Fluoro-3,5-dimethyl-phenylamino)-hexanoic acid (Intermediate A2)

(R)-2-Amino-hexanoic acid (0.840 g, 6.4 mmol), 5-bromo-2-fluoro-1,3-dimethyl-benzene (1.292 g, 6.4 mmol), CuI (0.122 g, 0.64 mmol), and $K_2CO_3$ (1.326 g, 9.6 mmol) were weighed into a Schlenk flask. To this was added 8 mL of dimethylacetamide and the resulting mixture vacuum-pumped and nitrogen-filled alternatively three times. After heating to 90° C. with stirring for 39 h, the reaction mixture was cooled to room temperature, diluted with 20 mL of ethyl acetate and 10 mL of water, and then acidified with concentrated HCl to pH=3. The layers were separated and the aqueous layer extracted with ethyl acetate (20 mL×5). The organic layers were combined and dried over anhydrous $Na_2SO_4$. Removal of the solvent under reduced pressure gave the title product which was used directly in the next step with further purification. LC-MS: $t_R$=8.5 min, m/z 254 $(M+H)^+$.

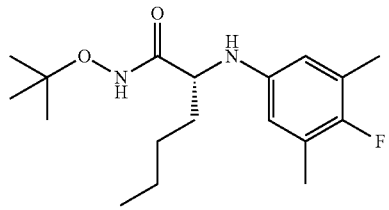

(R)-2-(4-Fluoro-3,5-dimethyl-phenylamino)-hexanoic acid tert-butoxy-amide (Intermediate B2)

To a solution of crude (R)-2-(4-fluoro-3,5-dimethyl-phenylamino)-hexanoic acid (ca. 6.0 mmol), O-tert-butyl-hydroxyamine (2.261 g, 18.0 mmol), HOBT (0.811 g, 6.0 mmol), and N-methyl morphine (3.036 g, 30.0 mmol) in 20 mL of dichloromethane, was added EDCI (1.725 g, 9.0 mmol). After stirring at room temperature under $N_2$ for 44 h, the reaction mixture was diluted with 60 mL of water and extracted with dichloromethane (60 mL×3). The organic extracts were combined and dried over anhydrous $Na_2SO_4$ and the solvents removed under reduced pressure. The product was isolated by Flash chromatography (silica gel) eluting with 0-30% ethyl acetate/hexanes to give the title compound as a pale yellow semi-solid (0.747 g, 38% yield). LC-MS: $t_R$=8.8 min; m/z 325 $(M+H)^+$.

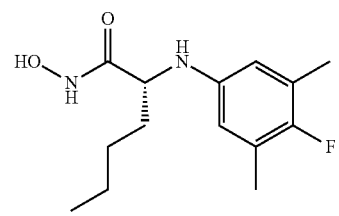

R)-2-(4-Fluoro-3,5-dimethyl-phenylamino)-hexanoic acid hydroxyamide (Compound 167294)

To a solution of (R)-2-(4-fluoro-3,5-dimethyl-phenylamino)-hexanoic acid tert-butoxy-amide (0.737 g, 2.273 mmol) in 1 mL of dichloromethane, was added trifluoroacetic acid (9 mL). After stirring at room temperature for 87 h, the reaction mixture was concentrated under reduced pressure. The product was isolated by Flash chromatography (silica gel) eluting with 0-10% methanol/dichoromethane to give the title compound as a white solid (0.182 g, 30% yield). Pure analytical sample was obtained by RP-HPLC purification. LC-MS: $t_R$=6.8 min; m/z 269 $(M+H)^+;)^+$; $^1H$ NMR (500 MHz, $CD_3OD$) δ 0.92 (t, J=7.05 Hz, 3H), 1.33-1.45 (m, 4H), 1.71-1.79 (m, 2H), 2.13 (d, J=2.02 Hz, 6H), 3.65 (t, J=7.05 Hz, 1H), 6.36 (d, J=5.88 Hz, 2H); $^{13}C$ NMR (125.75 MHz, $CD_3OD$) δ 14.24, 14.80, 23.50, 29.18, 33.99, 58.94, 115.65 (d, J=3.14 Hz), 125.69 (d, J=18.74 Hz), 143.30, 155.19 (d, J=233.14 Hz), 172.75; $^{19}F$ NMR (470.58 MHz, $CD_3OD$) δ −135.79.

Specific Scheme 3

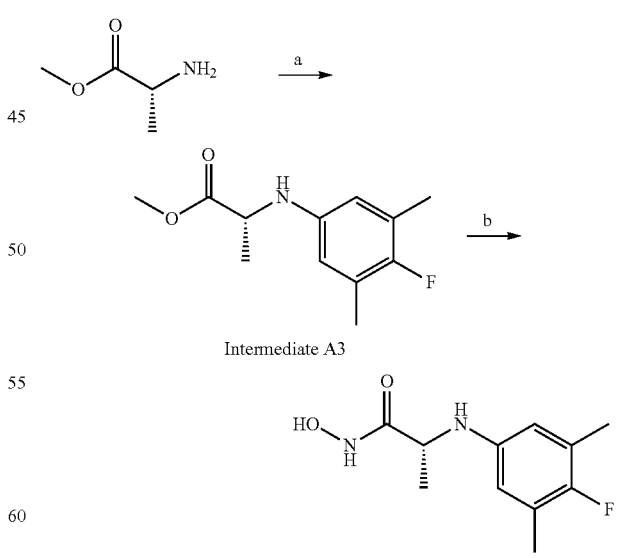

Reagents and conditions: (a) 2 eq of 3,5-dimethyl-4-fluorophenylboronic acid, 1.1 eq of $Cu(OAc)_2$, 2 eq of $Et_3N$, MS 4Å, DCM, open air, rt; (b) KCN (5 mol %), THF/MeOH/50% $NH_2OH$—$H_2O$ (2:2:1), rt.

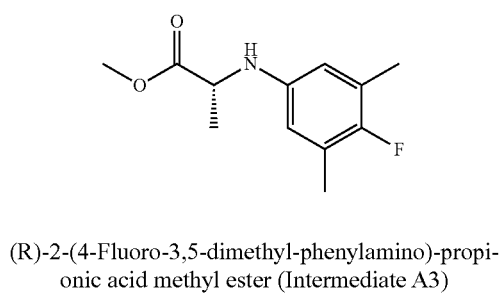

(R)-2-(4-Fluoro-3,5-dimethyl-phenylamino)-propionic acid methyl ester (Intermediate A3)

To a suspension of (R)-2-amino-propionic acid methyl ester (0.200 g, 1.940 mmol), 3,5-dimethyl-4-fluorophenylboronic acid (0.652 g, 3.880 mmol), Cu(OAc)$_2$ (0.388 g, 2.134 mmol), and molecular sieves 4 Å (1.456 g) in 15 mL of dichloromethane, was added triethylamine (0.54 mL, 3.880 mmol). After stirring at room temperature under O$_2$ for 39 h, the reaction mixture was filtered through a pad of Celite and washed with dichloromethane. The filtrate was concentrated under reduced pressure. The product was isolated by Flash chromatography (silica gel) eluting with 0-30% ethyl acetate/hexanes to give the title compound as brown oil (0.164 g, 38% yield). LC-MS: t$_R$=8.1 min; m/z 226 (M+H)$^+$.

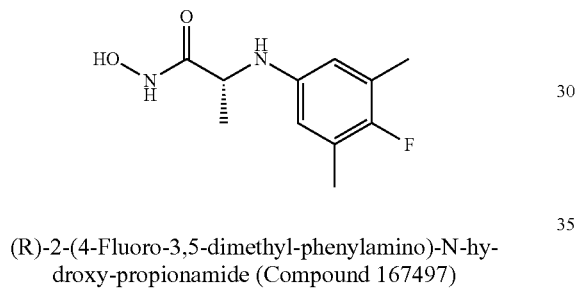

(R)-2-(4-Fluoro-3,5-dimethyl-phenylamino)-N-hydroxy-propionamide (Compound 167497)

To a solution of (R)-2-(4-fluoro-3,5-dimethyl-phenylamino)-propionic acid methyl ester (0.163 g, 0.724 mmol) in 5 mL of THF/MeOH/50% NH$_2$OH—H$_2$O (2:2:1), was added KCN (0.002 g, 0.036 mmol). After stirring at room temperature for 68 h, the reaction mixture was diluted with 60 mL of water and extracted with ethyl acetate (60 mL×3). The organic extracts were combined and dried over anhydrous Na$_2$SO$_4$. After removing the solvent under reduced pressure, the product was isolated by Flash chromatography (silica gel) eluting with 0-10% methanol/dichloromethane to give the title compound as a white solid (0.137 g, 84% yield). An analytical sample was obtained by RP-HPLC purification. LC-MS: t$_R$=4.4 min, m/z 227 (M+H)$^+$; $^1$H NMR (300 MHz, CD$_3$OD) δ 1.47, (d, J=6.74 Hz, 3H), 2.18 (s, 6H), 3.87 (q, J=6.74 Hz), 6.60 (d, J=5.86 Hz, 2H).

Specific Scheme 4

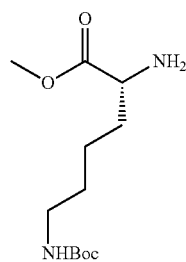

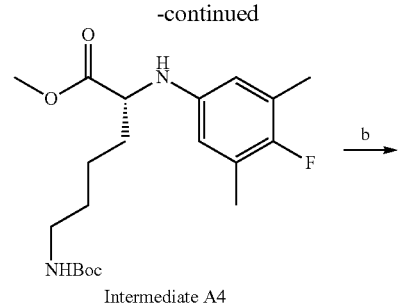

Intermediate A4

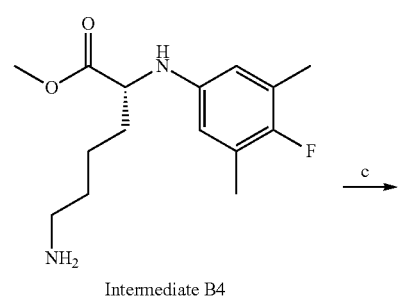

Intermediate B4

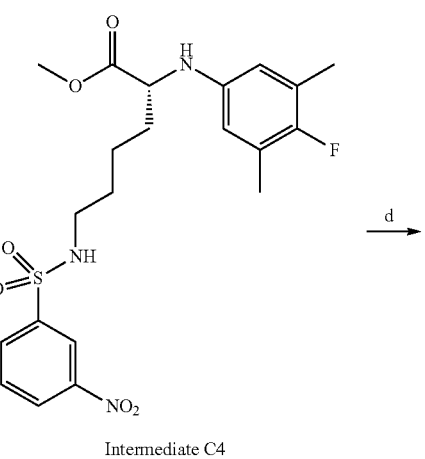

Intermediate C4

Compound 167622

Reagents and conditions: (a) 2 eq of 3,5-dimethyl-4-fluorophenylboronic acid, 1.1 eq. of Cu(OAc)$_2$, 2 eq of Et$_3$N, MS 4Å, DCM, open air, rt; (b) TFA/DCM (1:1), rt; (c) 1 eq of 3-nitro-benzenesulfonyl chloride, 5 eq of Et$_3$N, DCM, rt; (d) KCN (5 mol %), THF/MeOH/50% NH$_2$OH—H$_2$O (2:2:1), rt.

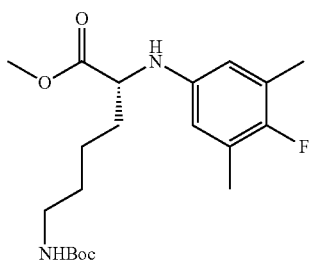

(R)-6-tert-Butoxycarbonylamino-2-(4-fluoro-3,5-dimethyl-phenylamino)-hexanoic acid methyl ester (Intermediate A4)

To a suspension of (R)-2-Amino-6-tert-butoxycarbonylamino-hexanoic acid methyl ester (3.000 g, 10.108 mmol), 3,5-dimethyl-4-fluorophenylboronic acid (3.398 g, 20.216 mmol), $Cu(OAc)_2$ (2.019 g, 11.119 mmol), and molecular sieves 4 Å (7.591 g) in 45 mL of dichloromethane, triethylamine (2.8 mL, 20.216 mmol) was added. After stirring at room temperature under $O_2$ for 87 h, the reaction mixture was filtered through a pad of Celite and washed with dichloromethane. The filtrate was concentrated under reduced pressure. The product was isolated by Flash chromatography (silica gel) eluting with 0-30% ethyl acetate/hexanes to give the title compound as colorless oil (3.084 g, 80% yield). LC-MS: $t_R$=9.8 min; m/z 383 (M+H)$^+$.

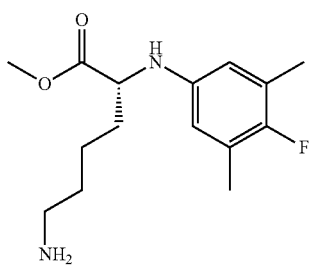

(R)-6-Amino-2-(4-fluoro-3,5-dimethyl-phenylamino)-hexanoic acid methyl ester (Intermediate B4)

To a solution of (R)-6-tert-butoxycarbonylamino-2-(4-fluoro-3,5-dimethyl-phenylamino)-hexanoic acid methyl ester (2.000 g, 5.232 mmol) in 10 mL of dichloromethane, was added trifluoroacetic acid (10 mL). After stirring at room temperature for 19 h, the reaction mixture was concentrated under reduced pressure, and the residue dried in vacuum for overnight at room temperature. The crude product (1.200 g, 81% yield) was used directly in the next step without further purification. LC-MS: $t_R$=4.8 min; m/z 283 (M+H)$^+$.

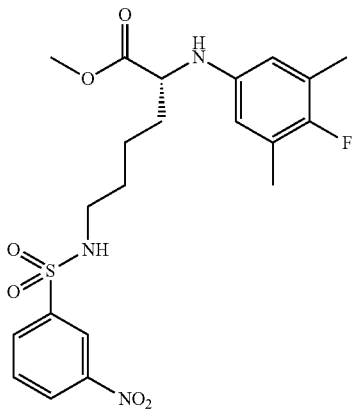

(R)-2-(4-Fluoro-3,5-dimethyl-phenylamino)-6-(3-nitro-benzenesulfonylamino)-hexanoic acid methyl ester (Intermediate C4)

To a solution of (R)-6-amino-2-(4-fluoro-3,5-dimethyl-phenylamino)-hexanoic acid methyl ester (0.200 g, 0.709 mmol) and 3-nitro-benzenesulfonyl chloride (0.157 g, 0.709 mmol) in 10 mL of dichloromethane, was added triethylamine (0.5 mL, 3.544 mmol). After stirring at room temperature under $N_2$ for 16 h, the reaction mixture was concentrated under reduced pressure. The product was isolated by Flash chromatography (silica gel) eluting with 20-50% ethyl acetate/hexanes to give the title compound as light yellow semi-solid (0.128 g, 39% yield). LC-MS: $t_R$=9.5 min; m/z 468 (M+H)$^+$.

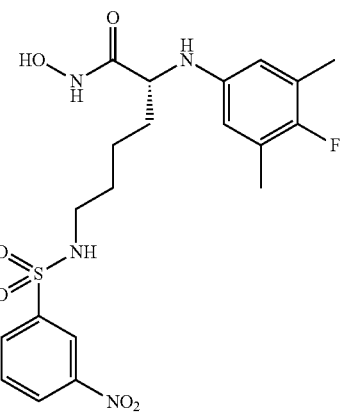

(R)-2-(4-Fluoro-3,5-dimethyl-phenylamino)-6-(3-nitro-benzenesulfonylamino)-hexanoic acid hydroxyamide (Compound 167266)

To a solution of (R)-2-(4-fluoro-3,5-dimethyl-phenylamino)-6-(3-nitro-benzenesulfonylamino)-hexanoic acid methyl ester (0.050 g, 0.107 mmol) in 2.5 mL of THF/MeOH/50% $NH_2OH$—$H_2O$ (2:2:1), was added KCN (0.001 g, 0.011 mmol). After stirring at room temperature for 16 h, the reaction mixture was concentrated under reduced pressure and the product isolated by Flash chromatography (silica gel) eluting with 0-10% methanol/dichloromethane to give the title compound as a light yellow solid (0.025 g, 50% yield). Pure analytical sample was obtained by RP-HPLC purification. LC-MS: $t_R$=7.2 min, m/z 469 (M+H)$^+$; $^1$H NMR (300 MHz, CD$_3$OD) δ 1.42-1.49 (m, 4H), 1.72-1.76 (m, 2H), 2.16 (s, 6H), 2.86-2.94 (m, 2H), 3.63 (t, J=6.74 Hz, 1H), 6.43 (d, J=5.86 Hz, 2H), 7.82 (t, J=8.05 Hz, 1H), 8.20 (d, J=7.62 Hz, 1H), 8.43 (d, J=7.91 Hz, 1H), 8.63 (s, 1H).

Specific Scheme 5

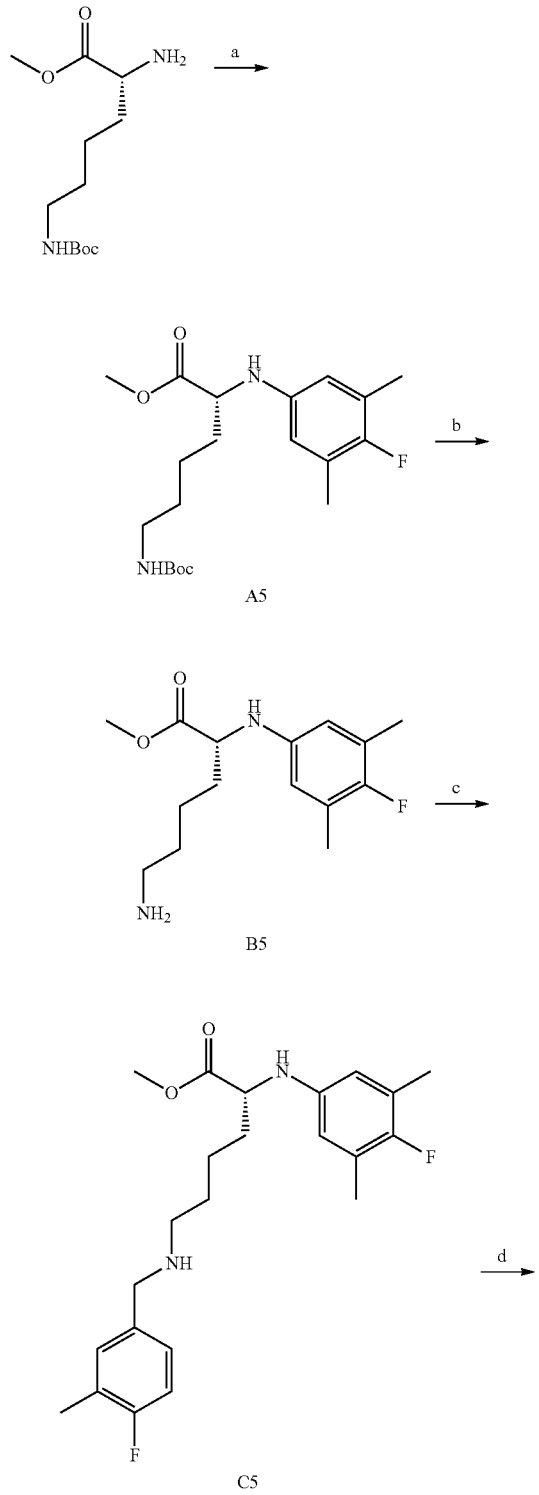

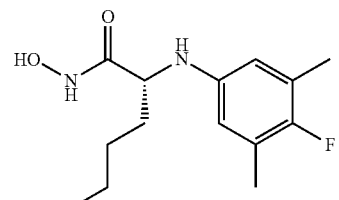

Compound 167654

Reagents and conditions: (a) 2 eq of 3,5-dimethyl-4-fluorophenylboronic acid, 1.1 eq of Cu(OAc)$_2$, 2 eq of Et$_3$N, MS 4Å, DCM, O$_2$, rt; (b) TFA/DCM (1:1), rt; (c) 1 eq of 4-fluoro-3-methylbenzaldehyde, 2 eq of Et$_3$N, 1.4 eq of NaBH(OAc)$_3$, DCE, rt; (d) KCN (5 mol %), THF/MeOH/50% NH$_2$OH—H$_2$O (2:2:1), rt.

(R)-6-tert-Butoxycarbonylamino-2-(4-fluoro-3,5-dimethyl-phenylamino)-hexanoic acid methyl ester (A5)

To a suspension of (R)-2-Amino-6-tert-butoxycarbonylamino-hexanoic acid methyl ester (3.000 g, 10.108 mmol), 3,5-dimethyl-4-fluorophenylboronic acid (3.398 g, 20.216 mmol), Cu(OAc)$_2$ (2.019 g, 11.119 mmol), and molecular sieves 4 Å (7.591 g) in 45 mL of dichloromethane, was added triethylamine (2.8 mL, 20.216 mmol). After stirring at room temperature under O$_2$ (1 atm) for 87 h, the reaction mixture was filtered through a pad of Celite and washed with dichloromethane. The filtrate was concentrated under reduced pressure. The product was isolated by Flash column chromatography (silica gel column) eluting with 0-30% ethyl acetate/hexanes to give the title compound as colorless oil (3.084 g, 80% yield). LC-MS: $t_R$=9.8 min; m/z 383 (M+H)$^+$.

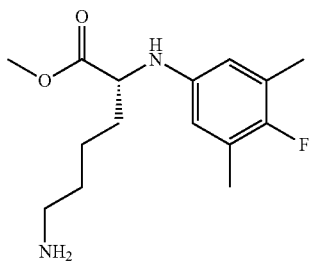

(R)-6-Amino-2-(4-fluoro-3,5-dimethyl-phenylamino)-hexanoic acid methyl ester (B5)

To a solution of (R)-6-tert-butoxycarbonylamino-2-(4-fluoro-3,5-dimethyl-phenylamino)-hexanoic acid methyl ester (2.000 g, 5.232 mmol) in 10 mL of dichloromethane, was added trifluoroacetic acid (10 mL). After stirring at room temperature for 19 h, the reaction mixture was concentrated under reduced pressure, and dried in vacuum for overnight. The crude product (1.200 g, 81% yield) was used directly in the next step without further purification. LC-MS: $t_R$=4.8 min; m/z 283 (M+H)$^+$.

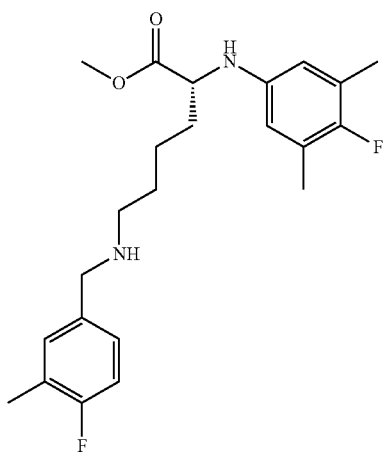

(R)-methyl 2-(4-fluoro-3,5-dimethylphenylamino)-6-(4-fluoro-3-methylbenzylamino)hexanoate (C5)

To a solution of (R)-6-amino-2-(4-fluoro-3,5-dimethyl-phenylamino)-hexanoic acid methyl ester (0.400 g, 1.009 mmol), 4-fluoro-3-methylbenzaldehyde (0.139 g, 1.009 mmol), and triethylamine (0.204 g, 2.018 mmol) in 10 mL of dichloroethane, was added NaBH(OAc)$_3$ (0.299 g, 1.413 mmol). After stirring at room temperature for 63 h, the reaction was quenched with 30 mL of saturated NaHCO$_3$ solution and the reaction mixture was extracted with ethyl acetate (30 mL×3). The combined organic extracts dried (Na$_2$SO$_4$), filtered, and concentrated under reduced pressure. The product was isolated by Flash column chromatography (silica gel column) eluting with 0-10% methanol/dichloromethane to give the title compound as brown oil (0.357 g, 87% yield). GC-MS: $t_R$=7.5 min; m/z 404 (M$^+$).

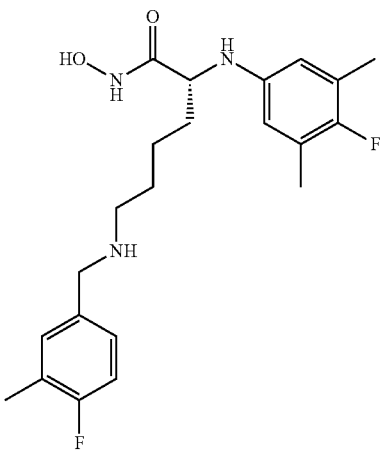

(R)-2-(4-fluoro-3,5-dimethylphenylamino)-6-(4-fluoro-3-methylbenzylamino)-N-hydroxyhexanamide (Compound 167654)

To a solution of (R)-methyl 2-(4-fluoro-3,5-dimethylphenylamino)-6-(4-fluoro-3-methylbenzylamino)hexanoate (0.350 g, 0.865 mmol) in 5 mL of THF/MeOH/50% NH$_2$OH—H$_2$O (2:2:1), was added KCN (0.006 g, 0.087 mmol). After stirring at room temperature for 62 h, the reaction mixture was acidified with concentrated HCl to pH=2 and filtered. The product was isolated by RP-HPLC eluting with 20-100% acetonitrile (0.025% TFA)/water (0.025% TFA) to give the title compound as a white solid (0.104 g, 30% yield). LC-MS: $t_R$=5.6 min, m/z 406 (M+H)$^+$. $^1$H NMR (500 MHz, CD$_3$OD) δ 1.48-1.58 (m, 2H), 1.69-1.76 (m, 2H), 1.77-1.86 (m, 2H), 2.13 (d, J=1.85 Hz, 6H), 2.29 (d, J=1.68 Hz, 3H), 3.02 (td, J=7.05, 2.86 Hz, 2H), 3.66 (t, J=6.89 Hz, 1H), 4.12 (s, 2H), 6.32 (d, J=5.87 Hz, 2H), 7.11 (t, J=8.89 Hz, 1H), 7.28-7.31 (m, 1H), 7.35 (d, J=7.05 Hz, 1H); $^{13}$C NMR (125.75 MHz, CD$_3$OD) δ 14.42, 14.81, 24.09, 26.78, 33.64, 51.60, 58.37, 115.09, 116.58 (d, J=18.36 Hz), 116.83, 125.70 (d, J=18.74 Hz), 128.38, 130.41, 130.48, 134.41, 143.93, 154.01, 172.80, 201.40; $^{19}$F NMR (470.58 MHz, CD$_3$OD) δ −136.54, −116.83.

Specific Scheme 6

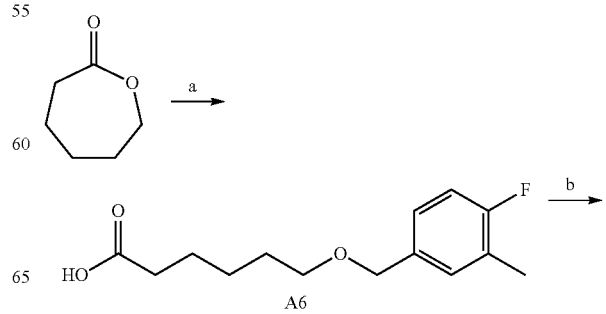

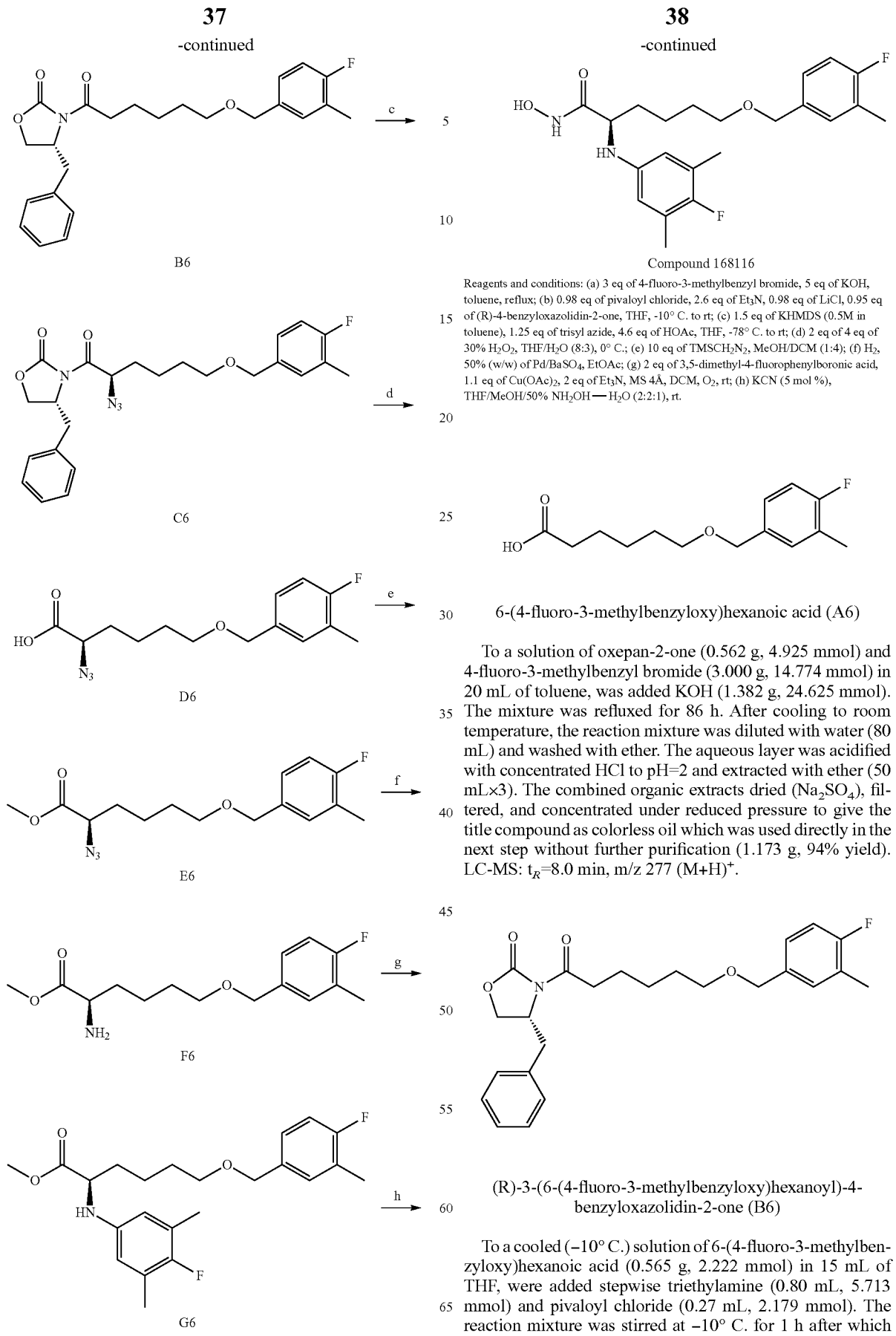

Reagents and conditions: (a) 3 eq of 4-fluoro-3-methylbenzyl bromide, 5 eq of KOH, toluene, reflux; (b) 0.98 eq of pivaloyl chloride, 2.6 eq of Et₃N, 0.98 eq of LiCl, 0.95 eq of (R)-4-benzyloxazolidin-2-one, THF, -10° C. to rt; (c) 1.5 eq of KHMDS (0.5M in toluene), 1.25 eq of trisyl azide, 4.6 eq of HOAc, THF, -78° C. to rt; (d) 2 eq of 4 eq of 30% H₂O₂, THF/H₂O (8:3), 0° C.; (e) 10 eq of TMSCH₂N₂, MeOH/DCM (1:4); (f) H₂, 50% (w/w) of Pd/BaSO₄, EtOAc; (g) 2 eq of 3,5-dimethyl-4-fluorophenylboronic acid, 1.1 eq of Cu(OAc)₂, 2 eq of Et₃N, MS 4Å, DCM, O₂, rt; (h) KCN (5 mol %), THF/MeOH/50% NH₂OH—H₂O (2:2:1), rt.

6-(4-fluoro-3-methylbenzyloxy)hexanoic acid (A6)

To a solution of oxepan-2-one (0.562 g, 4.925 mmol) and 4-fluoro-3-methylbenzyl bromide (3.000 g, 14.774 mmol) in 20 mL of toluene, was added KOH (1.382 g, 24.625 mmol). The mixture was refluxed for 86 h. After cooling to room temperature, the reaction mixture was diluted with water (80 mL) and washed with ether. The aqueous layer was acidified with concentrated HCl to pH=2 and extracted with ether (50 mL×3). The combined organic extracts dried (Na₂SO₄), filtered, and concentrated under reduced pressure to give the title compound as colorless oil which was used directly in the next step without further purification (1.173 g, 94% yield). LC-MS: $t_R$=8.0 min, m/z 277 (M+H)⁺.

(R)-3-(6-(4-fluoro-3-methylbenzyloxy)hexanoyl)-4-benzyloxazolidin-2-one (B6)

To a cooled (−10° C.) solution of 6-(4-fluoro-3-methylbenzyloxy)hexanoic acid (0.565 g, 2.222 mmol) in 15 mL of THF, were added stepwise triethylamine (0.80 mL, 5.713 mmol) and pivaloyl chloride (0.27 mL, 2.179 mmol). The reaction mixture was stirred at −10° C. for 1 h after which LiCl (0.092 g, 2.179 mmol) and (R)-4-benzyloxazolidin-2- one (0.375 g, 2.116 mmol) were added stepwise. After warming slowly to room temperature with stirring overnight, the reaction mixture was diluted with ethyl acetate (80 mL) and washed with saturated NaHCO$_3$ solution and brine. The organic layer was dried (Na$_2$SO$_4$), filtered, and concentrated under reduced pressure. The product was isolated by Flash column chromatography (silica gel column) eluting with 0-100% dichloromethane/hexanes to give the title compound as colorless oil (0.482 g, 52% yield). LC-MS: $t_R$=11.2 min; m/z 414 (M+H)$^+$.

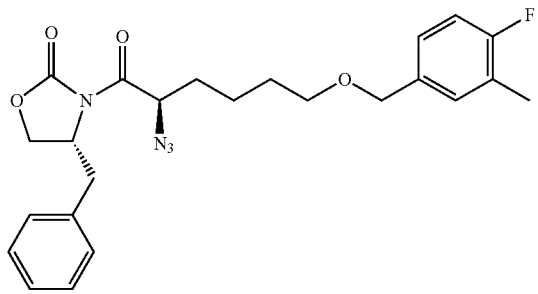

(R)-3-((R)-6-(4-fluoro-3-methylbenzyloxy)-2-azidohexanoyl)-4-benzyloxazolidin-2-one (C6)

To a cooled (−78° C.) solution of KHMDS (3.49 mL, 1.745 mol, 0.5 M in toluene) in 5 mL of THF was added a cooled (−78° C.) solution of (R)-3-(6-(4-fluoro-3-methylbenzyloxy)hexanoyl)-4-benzyloxazolidin-2-one (0.481 g, 1.163 mmol) in 4 mL of THF. The reaction was stirred at −78° C. under N$_2$ for 1 h. Then a cooled (−78° C.) solution of trisyl azide (0.448 g, 1.454 mmol) in 4 mL of THF was added. After 1-2 min, a solution of HOAc (0.321 g, 5.350 mmol) in 4 mL of THF was added. After warmed slowly to room temperature and stirred for overnight, the reaction mixture was diluted with brine (50 mL) and extracted with dichloromethane (40 mL×3). The combined organic extracts dried (Na$_2$SO$_4$), filtered, and concentrated under reduced pressure. The product was isolated by Flash column chromatography (silica gel column) eluting with 0-100% dichloromethane/hexanes to give the title compound as colorless oil (0.252 g, 48% yield). FT-IR (neat): 2104, 1778, 1704 cm$^{-1}$.

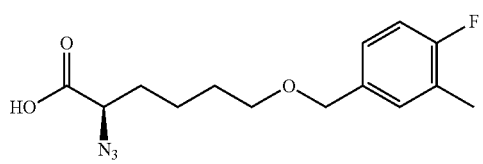

(R)-6-(4-fluoro-3-methylbenzyloxy)-2-azidohexanoic acid (D6)

To a cooled (0° C.) solution of (R)-3-((R)-6-(4-fluoro-3-methylbenzyloxy)-2-azidohexanoyl)-4-benzyloxazolidin-2-one (0.251 g, 0.552 mmol) in 11 mL of THF/H$_2$O (8:3), were added stepwise 30% H$_2$O$_2$ (0.22 mL, 2.208 mmol) and LiOH (0.046 g, 1.105 mmol). The reaction mixture was stirred at 0° C. for 1 h then room temperature for overnight. Then a solution of Na$_2$SO$_3$ (0.304 g, 2.412 mmol) in 3 mL of water was added. After stirred at room temperature for 10 min, the reaction mixture was acidified with 4N HCl to pH=2 and extracted with dichloromethane (30 mL×3). The combined organic extracts dried (Na$_2$SO$_4$), filtered, and concentrated under reduced pressure. The residue was used directly in the next step without further purification (0.163 g, >99% yield).

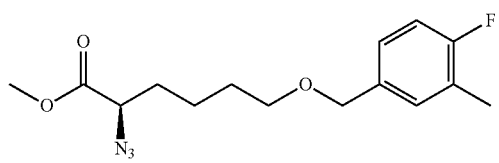

(R)-methyl 6-(4-fluoro-3-methylbenzyloxy)-2-azidohexanoate (E6)

To a solution of crude (R)-6-(4-fluoro-3-methylbenzyloxy)-2-azidohexanoic acid (0.163 g, 0.552 mmol) in 10 mL of dichloromethane/methanol (4:1), trimethylsilyldiazomethane was added dropwise until the solution became yellow. After stirred at room temperature under N$_2$ for 30 min, the reaction mixture was concentrated under reduced pressure. The product was isolated by Flash column chromatography (silica gel column) eluting with 0-100% dichloromethane/hexanes to give the title compound as colorless oil (0.141 g, 83% yield)

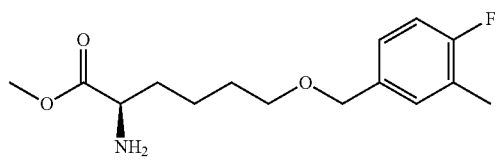

(R)-methyl 6-(4-fluoro-3-methylbenzyloxy)-2-aminohexanoate (F6)

To a solution of (R)-methyl 6-(4-fluoro-3-methylbenzyloxy)-2-azidohexanoate (0.141 g, 0.453 mmol) in 10 mL of ethyl acetate, Pd on BaSO$_4$ (0.070 g) was added. The mixture was flushed with H$_2$ for 15 min and stirred at room temperature under H$_2$ for 1 h. The reaction mixture was then filtered through a pad of Celite and washed with ethyl acetate. The filtrate was concentrated under reduced pressure. The residue was used in the next step without further purification (0.128 g, >99% yield). GC-MS: $t_R$=4.0 min; m/z 283 (M$^+$).

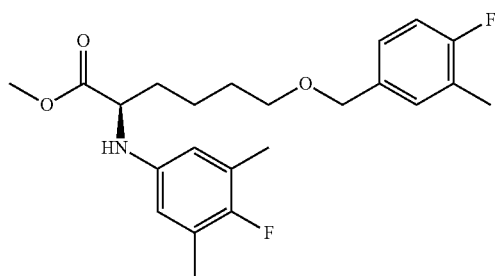

41

(R)-methyl 2-(4-fluoro-3,5-dimethylphenylamino)-6-(4-fluoro-3-methylbenzyloxy)hexanoate (G6)

To a suspension of crude (R)-methyl 6-(4-fluoro-3-methylbenzyloxy)-2-aminohexanoate (0.128 g, 0.453 mmol), 3,5-dimethyl-4-fluorophenylboronic acid (0.152 g, 0.906 mmol), $Cu(OAc)_2$ (0.090 g, 0.498 mmol), and molecular sieves 4 Å (0.400 g) in 5 mL of dichloromethane, was added triethylamine (0.13 mL, 0.906 mmol). After stirring at room temperature under $O_2$ (1 atm) for 44 h, the reaction mixture was filtered through a pad of Celite and washed with dichloromethane. The filtrate was concentrated under reduced pressure. The product was isolated by Flash column chromatography (silica gel column) eluting with 0-30% ethyl acetate/hexanes to give the title compound as light yellow oil (0.126 g, 68% yield). GC-MS: $t_R$=7.0 min; m/z 405 (M⁺).

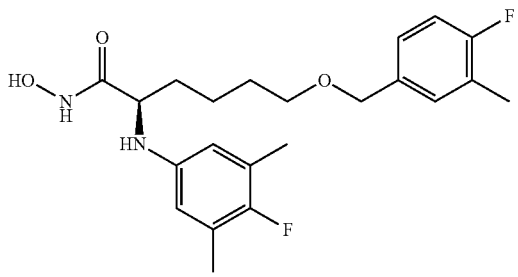

42

(R)-2-(4-fluoro-3,5-dimethylphenylamino)-6-(4-fluoro-3-methylbenzyloxy)-N-hydroxyhexanamide (Compound 168116)

To a solution of (R)-methyl 2-(4-fluoro-3,5-dimethylphenylamino)-6-(4-fluoro-3-methylbenzyloxy)hexanoate (0.125 g, 0.308 mmol) in 2.5 mL of THF/MeOH/50% $NH_2OH-H_2O$ (2:2:1), KCN (0.001 g, 0.015 mmol) was added. After stirring at room temperature for 15 h, the reaction mixture was acidified with concentrated HCl to pH=2 and filtered. The filtrate was purified by RP-HPLC eluting with 20-100% acetonitrile (0.025% TFA)/water (0.025% TFA) to give the title compound as an off-white solid (0.054 g, 43% yield). LC-MS: $t_R$=8.9 min, m/z 407 (M+H)⁺. ¹H NMR (300 MHz, $CD_3OD$) δ 1.43-1.58 (m, 2H), 1.59-1.70 (m, 2H), 1.71-1.88 (m, 2H), 2.15 (s, 6H), 2.24 (s, 3H), 3.48 (t, J=6.15 Hz, 2H), 3.67 (t, J=6.74 Hz, 1H), 4.41 (s, 2H), 6.39 (d, J=5.86 Hz, 2H), 6.96 (t, J=8.93 Hz, 1H), 7.10-7.14 (m, 1H), 7.18 (d, J=8.20 Hz, 1H).

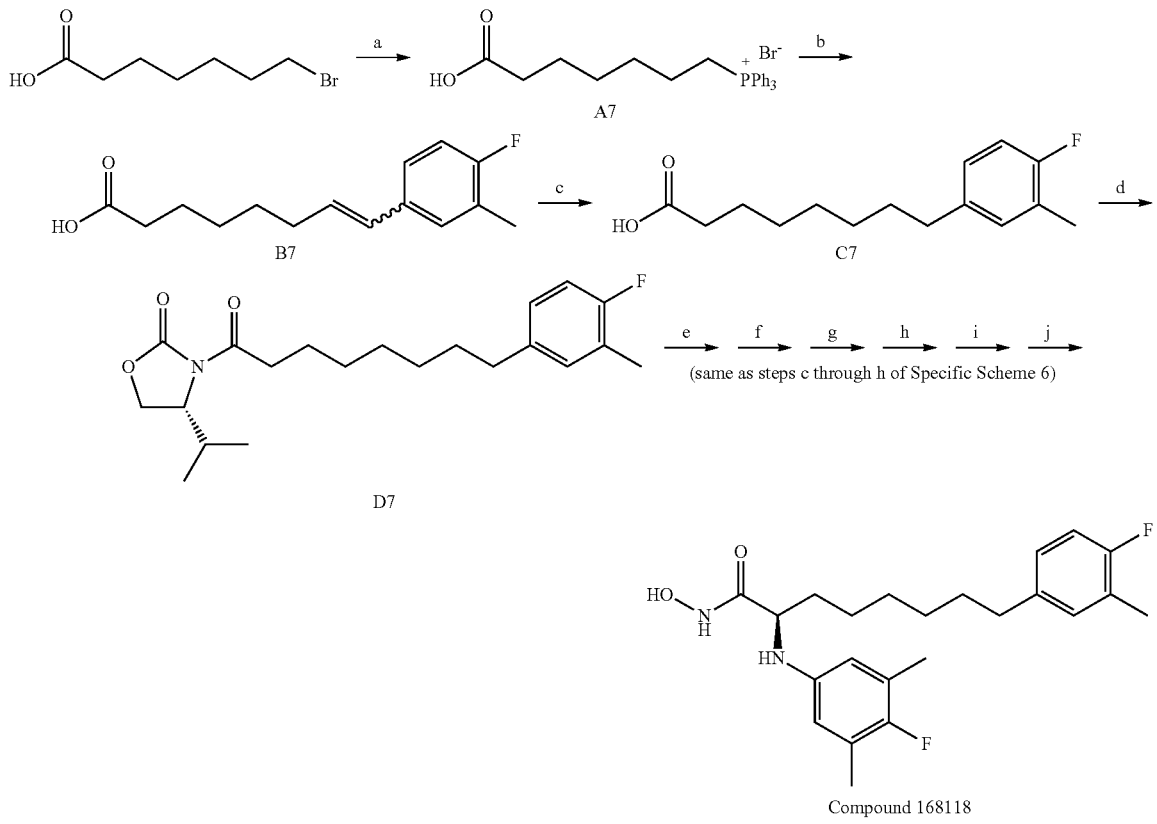

Reagents and conditions: (a) 1.1 eq of $PPh_3$, toluene, reflux; (b) 0.6 eq of 4-fluoro-3-methylbenzaldehyde, 3- eq of t-BuOK (1M in THF), benzene, reflux; (c) $H_2$, 20% (w/w) of Pd/C, MeOH; (d) 0.98 eq of pivaloyl chloride, 2.6 eq of $Et_3N$, 0.98 eq of LiCl, 0.95 eq of (R)-4-iso-propyloxazolidin-2-one, THF, -10° C. to rt; (e) 1.5 eq of KHMDS (0.5M in toluene), 1.25 eq of trisyl azide, 4.6 eq of HOAc, THF, -78° C. to rt; (f) 2 eq of LiOH, 4 eq of 30% $H_2O_2$, THF/$H_2O$ (8:3), 0° C.; (g) 10 eq of $TMSCHN_2$, MeOH/DCM (1:4); (h) $H_2$, Pd/$BaSO_4$, EtOAc; (i) 2 eq of 3,5-dimethyl-4-fluorophenylboronic acid, 1.1 eq of $Cu(OAc)_2$, 2 eq of $Et_3N$, MS 4Å, DCM, $O_2$, rt; (j) KCN (5 mol %), THF/MeOH/50% $NH_2OH-H_2O$ (2:2:1), rt.

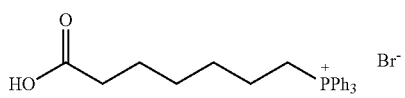

7-Carboxyheptanyltriphenylphosphonium bromide (A7)

A solution of 7-bromoheptanoic acid (5.000 g, 23.913 mmol) and PPh₃ (6.899 g, 26.304 mmol) in 50 mL of toluene was refluxed for 63 h. After cooling to room temperature, the solvent was removed under reduced pressure and the residue was tritiated with ether three times and dried in vacuum to give the title compound as a white foam solid (9.240 g, 82% yield).

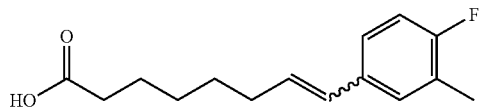

8-(4-fluoro-3-methylphenyl)oct-7-enoic acid (B7)

To a suspension of 7-Carboxyheptanyltriphenylphosphonium bromide (9.240 g, 19.602 mmol) in 100 mL of benzene, was added t-BuOK (58.8 mL, 58.8 mmol, 1M in THF). The resulting mixture was refluxed for 1 h and then 4-fluoro-3-methylbenzaldehyde (1.43 mL, 11.761 mmol) was added via a syringe. The mixture was refluxed under N₂ for an additional 63 h. After cooling to room temperature, the reaction mixture was washed with water (80 mL) and the aqueous layer was acidified with concentrated HCl to pH=2 and extracted with ethyl acetate (30 mL×3). The combined organic extracts dried (Na₂SO₄), filtered, and concentrated under reduced pressure. The product was isolated by Flash column chromatography (silica gel column) eluting with 0-30% ethyl acetate/hexanes to give the title compound as colorless oil (3.150 g, >99% yield). LC-MS: $t_R$=9.6 min, m/z 251 (M+H)⁺.

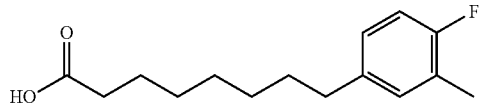

8-(4-fluoro-3-methylphenyl)octanoic acid (C7)

To a solution of 8-(4-fluoro-3-methylphenyl)oct-7-enoic acid (0.976 g, 3.899 mmol) in 30 mL of MeOH, was added 10% Pd on C (0.195 g). After stirred at room temperature under H₂ (1 atm) for 63 h, the reaction mixture was filtered through a pad of Celite and washed with ethyl acetate. The filtrate was concentrated under reduced pressure. The residue was used directly in the next step without further purification (0.938 g, 95% yield). LC-MS: $t_R$=10.1 min, m/z 253 (M+H)⁺.

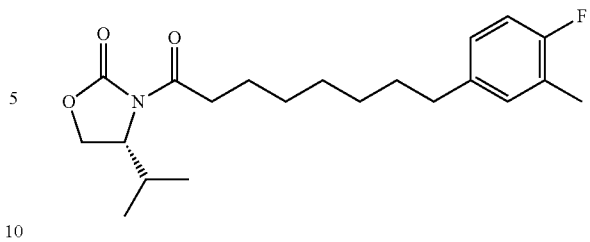

(R)-3-(8-(4-fluoro-3-methylphenyl)octanoyl)-4-isopropyloxazolidin-2-one (D7)

To a cooled (−10° C.) solution of 8-(4-fluoro-3-methylphenyl)octanoic acid (0.486 g, 1.926 mmol) in 15 mL of THF, were added stepwise triethylamine (0.69 mL, 4.952 mmol) and pivaloyl chloride (0.23 mL, 1.889 mmol). The reaction mixture was stirred at −10° C. for 1 h and then LiCl (0.080 g, 1.889 mmol) and (R)-4-iso-propyloxazolidin-2-one (0.237 g, 1.834 mmol) were added stepwise. After being warmed slowly to room temperature and stirred for overnight, the reaction mixture was diluted with ethyl acetate (80 mL) and washed with saturated NaHCO₃ solution and brine. The organic layer was dried (Na₂SO₄), filtered, and concentrated under reduced pressure. The product was isolated by Flash column chromatography (silica gel column) eluting with 0-100% dichloromethane/hexanes to give the title compound as colorless oil (0.547 g, 82% yield). GC-MS: $t_R$=6.9 min; m/z 363 (M⁺).

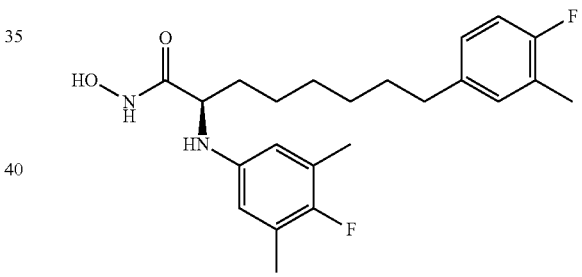

(R)-2-(4-Fluoro-3,5-dimethyl-phenylamino)-8-(4-fluoro-3-methyl-phenyl)-octanoic acid hydroxyamide (Compound 168118)

To a solution of (R)-2-(4-Fluoro-3,5-dimethyl-phenylamino)-8-(4-fluoro-3-methyl-phenyl)-octanoic acid methyl ester (0.184 g, 0.455 mmol) in 5 mL of THF/MeOH/50% NH₂OH—H₂O (2:2:1), KCN (0.002 g, 0.022 mmol) was added. After stirring at room temperature for 38 h, the reaction mixture was acidified with concentrated HCl to pH=2 and filtered. The filtrate was purified by RP-HPLC eluting with 20-100% acetonitrile (0.025% TFA)/water (0.025% TFA) to give the title compound as a white solid (0.053 g, 29% yield). LC-MS: $t_R$=10.4 min, m/z 405 (M+H)⁺; ¹HNMR (300 MHz, CD₃OD) δ 1.27-1.48 (m, 6H), 1.50-1.65 (m, 2H), 1.66-1.82 (m, 2H), 2.14 (s, 6H), 2.21 (s, 3H), 2.53 (t, J=7.47 Hz, 2H), 3.63 (t, J=6.88 Hz, 1H), 6.32 (d, J=5.86 Hz, 2H), 6.86 (t, J=8.93 Hz, 1H), 6.90-6.94 (m, 1H), 6.99 (d, J=7.62 Hz, 1H).

as an off-white solid (0.016 g, 66% yield). LC-MS: $t_R$=5.5 min, m/z 405 (M+H)⁺.

ABBREVIATIONS

DMF=dimethylformamide
DMA=dimethylacetamide
HOBt=1-hydroxybenzotriazole
NMM=N-methylmorpholine
EDC=N-(-dimethylaminopropyl)-N'-ethylcarbodiimide
DCM=dichloromethane
TFA=trifluoroacetic acid
MS molecular sieves
KHMDS=Potassium bis(trimethylsilyl)amide
RP-HPLC=Reverse Phase HPLC
trisyl azide=2,4,6-triisopropylbenzenesulfonyl azide Table 1 Compounds

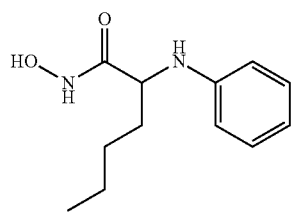

2-Phenylamino-hexanoic acid hydroxyamide (Compound 167210) Prepared According to General Scheme 1

LC-MS: $t_R$=5:3 min, m/z 223 (M+H)$^+$.

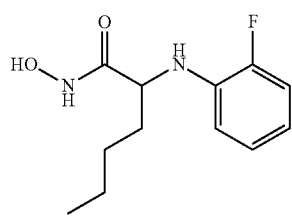

2-(2-Fluoro-phenylamino)-hexanoic acid hydroxyamide (Compound 167291) Prepared According to General Scheme 10

LC-MS: $t_R$=6.0 min, m/z 241 (M+H)$^+$.

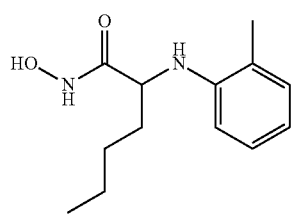

2-o-Tolylamino-hexanoic acid hydroxyamide (Compound 167292) Prepared According to General Scheme 1

LC-MS: $t_R$=6.3 min, m/z 237 (M+H)$^+$.

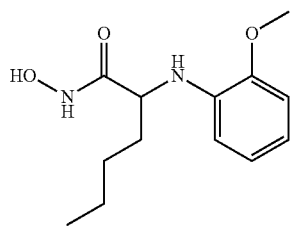

2-(2-Methoxy-phenylamino)-hexanoic acid hydroxyamide (Compound 167293) Prepared According to General Scheme 1

LC-MS: $t_R$=5.8 min, m/z 253 (M+H)$^+$.

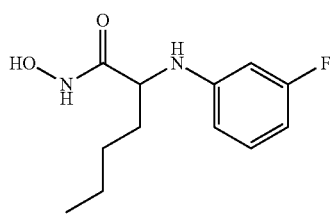

2-(3-Fluoro-phenylamino)-hexanoic acid hydroxyamide (Compound 167277) Prepared According to General Scheme 1

LC-MS: $t_R$=6.0 min, m/z 241 (M+H)$^+$.

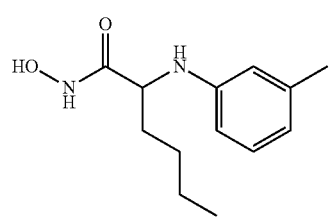

2-m-Tolylamino-hexanoic acid hydroxyamide (Compound 167170) Prepared According to General Scheme 1

LC-MS: $t_R$=6.0 min, m/z 232 (M+H)$^+$.

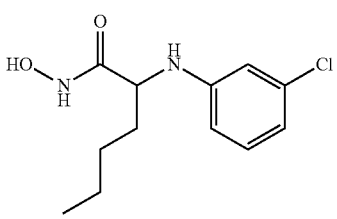

2-(3-Chloro-phenylamino)-hexanoic acid hydroxyamide (Compound 167257) Prepared According to General Scheme 1

LC-MS: N=6.6 min, m/z 257 (M+H)$^+$.

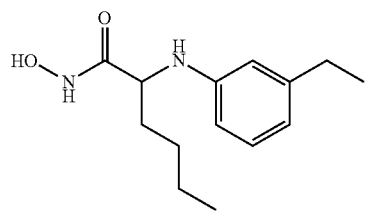

2-(3-Ethyl-phenylamino)-hexanoic acid hydroxyamide (Compound 167201) Prepared According to General Scheme 1

LC-MS: $t_R$=6.7 min, m/z 251 (M+H)$^+$.

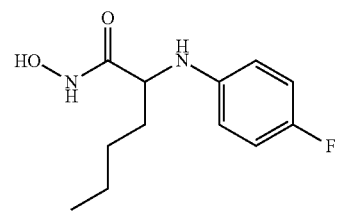

2-(4-Fluoro-phenylamino)-hexanoic acid hydroxyamide (Compound 167211) Prepared According to General Scheme 1

LC-MS: $t_R$=5.6 min, m/z 241 (M+H)$^+$.

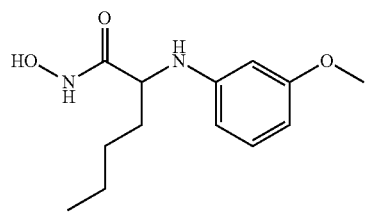

2-(3-Methoxy-phenylamino)-hexanoic acid hydroxyamide (Compound 167276) Prepared According to General Scheme 1

LC-MS: $t_R$=5.5 min, m/z 253 (M+H)$^+$.

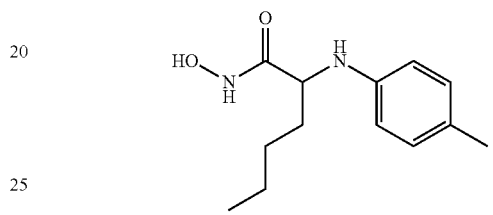

2-p-Tolylamino-hexanoic acid hydroxyamide (Compound 167255) Prepared According to General Scheme 1

LC-MS: $t_R$=5.7 min, m/z 2237 (M+H)$^+$.

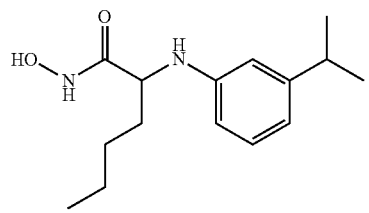

2-(3-Isopropyl-phenylamino)-hexanoic acid hydroxyamide (Compound 167183) Prepared According to General Scheme 1

LC-MS: $t_R$=7.3 min, m/z 265 (M+H)$^+$.

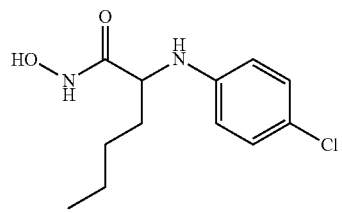

2-(4-Chloro-phenylamino)-hexanoic acid hydroxyamide (Compound 167256) Prepared According to General Scheme 1

LC-MS: $t_R$=6.5 min, m/z 257 (M+H)$^+$.

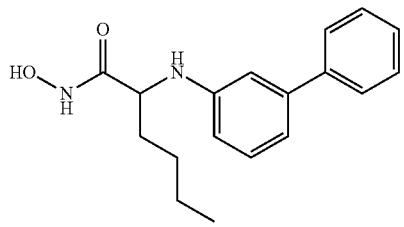

2-(Biphenyl-3-ylamino)-hexanoic acid hydroxyamide (Compound 167202) Prepared According to General Scheme 1

LC-MS: $t_R$=7.7 min, m/z 299 (M+H)$^+$.

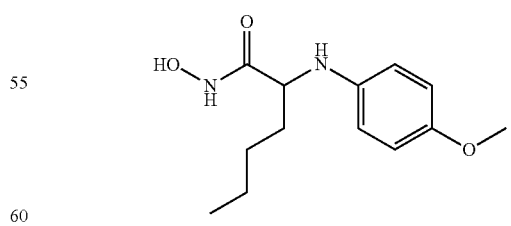

2-(4-Methoxy-phenylamino)-hexanoic acid hydroxyamide (167275) Prepared According to General Scheme 1

LC-MS: $t_R$=4.1 min, m/z 253 (M+H)$^+$.

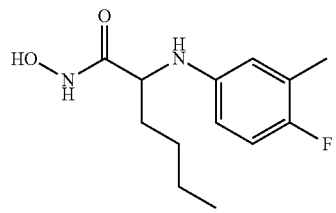

2-(4-Fluoro-3-methyl-phenylamino)-hexanoic acid hydroxyamide (Compound 167162) Prepared According to General Scheme 1

LC-MS: $t_R$=6.0 min, m/z 255 (M+H)$^+$.

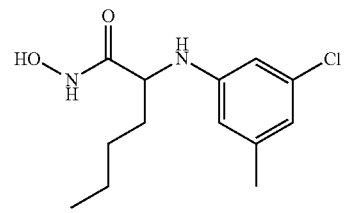

2-(3-Chloro-5-methyl-phenylamino)-hexanoic acid hydroxyamide (Compound 167645) Prepared According to General Scheme 1

LC-MS: $t_R$=7.3 min, m/z 271 (M+H)$^+$.

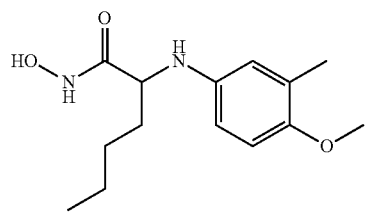

2-(4-Methoxy-3-methyl-phenylamino)-hexanoic acid hydroxyamide (Compound 167324) Prepared According to General Scheme 1

LC-MS: $t_R$=4.6 min, m/z 267 (M+H)$^+$.

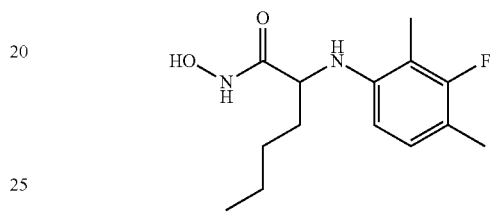

2-(3-Fluoro-2,4-dimethyl-phenylamino)-hexanoic acid hydroxyamide (Compound 167455) Prepared According to General Scheme 1

LC-MS: $t_R$=7.5 min, m/z 269 (M+H)$^+$.

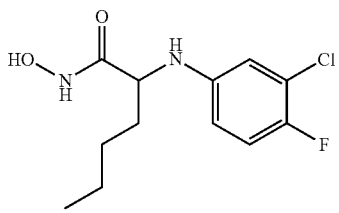

2-(3-Chloro-4-fluoro-phenylamino)-hexanoic acid hydroxyamide (Compound 167322) Prepared According to General Scheme 1

LC-MS: $t_R$=6.8 min, m/z 275 (M+H)$^+$.

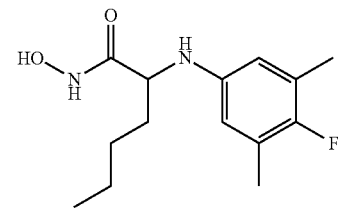

2-(4-Fluoro-3,5-dimethyl-phenylamino)-hexanoic acid hydroxyamide (Compound 167454) Prepared According to General Scheme 1

LC-MS: $t_R$=6.8 min, m/z 269 (M+H)$^+$.

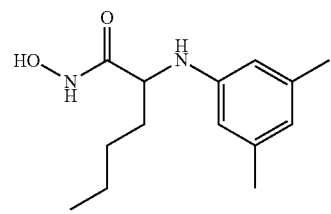

2-(3,5-Dimethyl-phenylamino)-hexanoic acid hydroxyamide (Compound 167226) Prepared According to General Scheme 1

LC-MS: $t_R$=6.6 min, m/z 251 (M+H)$^+$.

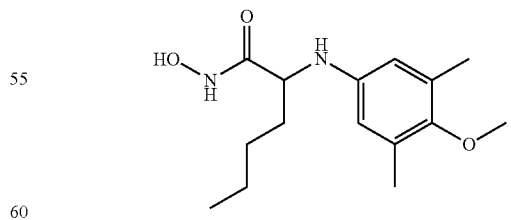

2-(4-Methoxy-3,5-dimethyl-phenylamino)-hexanoic acid hydroxyamide (Compound 167325) Prepared According to General Scheme 1

LC-MS: $t_R$=5.8 min, m/z 281 (M+H)$^+$.

Table 2 Compounds

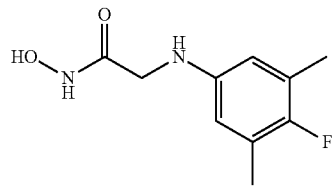

2-(4-Fluoro-3,5-dimethyl-phenylamino)-N-hydroxy-acetamide (Compound 167452) Prepared According to General Scheme 2 or 3

LC-MS: $t_R$=4.5 min, m/z 213 (M+H)$^+$.

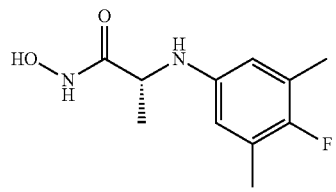

(R)-2-(4-Fluoro-3,5-dimethyl-phenylamino)-N-hydroxy-propionamide (Compound 167497) Prepared According to General Scheme 2 or 3

LC-MS: $t_R$=4.4 min, m/z 227 (M+H)$^+$.

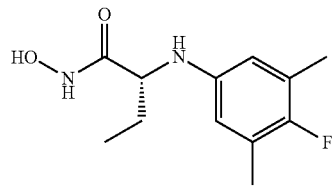

(R)-2-(4-Fluoro-3,5-dimethyl-phenylamino)-N-hydroxy-butyramide (Compound 167450) Prepared According to General Scheme 2 or 3

LC-MS: $t_R$=5.1 min, m/z 241 (M+H)$^+$.

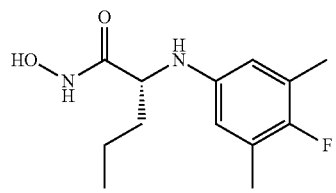

(R)-2-(4-Fluoro-3,5-dimethyl-phenylamino)-pentanoic acid hydroxyamide (Compound 167391) Prepared According to General Scheme 2 or 3

LC-MS: $t_R$=6.0 min, m/z 255 (M+H)$^+$.

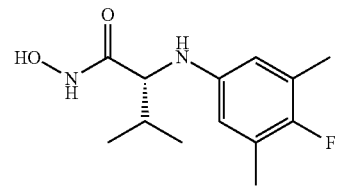

(R)-2-(4-Fluoro-3,5-dimethyl-phenylamino)-N-hydroxy-3-methyl-butyramide (Compound 167264) Prepared According to General Scheme 2 or 3

LC-MS: $t_R$=6.0 min, m/z 255 (M+H)$^+$.

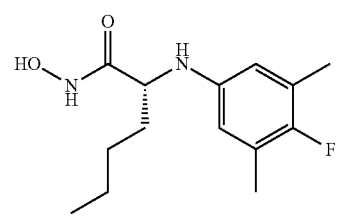

(R)-2-(4-Fluoro-3,5-dimethyl-phenylamino)-hexanoic acid hydroxyamide (Compound 167294) Prepared According to General Scheme 2 or 3

LC-MS: $t_R$=6.7 min, m/z 269 (M+H)$^+$.

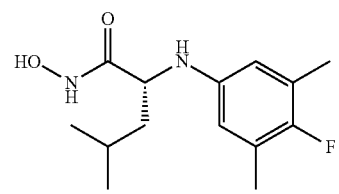

(R)-2-(4-Fluoro-3,5-dimethyl-phenylamino)-4-methyl-pentanoic acid hydroxyamide (Compound 167402) Prepared According to General Scheme 2 or 3

LC-MS: $t_R$=6.7 min, m/z 269 (M+H)$^+$.

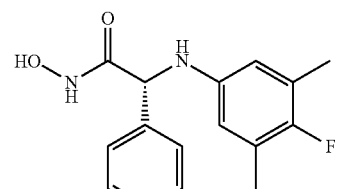

(R)-2-(4-Fluoro-3,5-dimethyl-phenylamino)-N-hydroxy-2-phenyl-acetamide (Compound 167425) Prepared According to General Scheme 2 or 3

LC-MS: $t_R$=6.8 min, m/z 289 (M+H)$^+$.

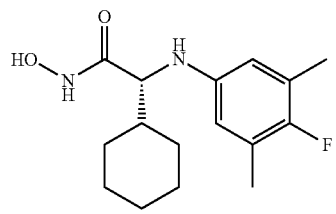

(R)-2-Cyclohexyl-2-(4-fluoro-3,5-dimethyl-phenylamino)-N-hydroxy-acetamide (Compound 167424) Prepared According to General Scheme 2 or 3

LC-MS: $t_R$=7.5 min, m/z 295 (M+H)$^+$.

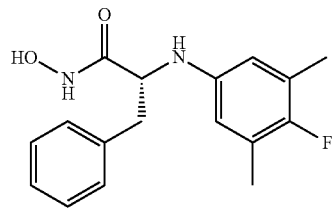

(R)-2-(4-Fluoro-3,5-dimethyl-phenylamino)-N-hydroxy-3-phenyl-propionamide (Compound 167378) Prepared According to General Scheme 2 or 3

LC-MS: $t_R$=7.0 min, m/z 303 (M+H)$^+$.

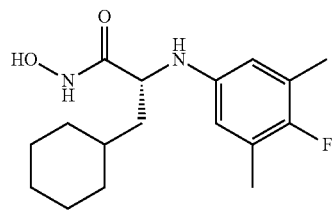

(R)-3-Cyclohexyl-2-(4-fluoro-3,5-dimethyl-phenylamino)-N-hydroxy-propionamide (Compound 167405) Prepared According to General Scheme 2 or 3

LC-MS: $t_R$=8.1 min, m/z 309 (M+H)$^+$.

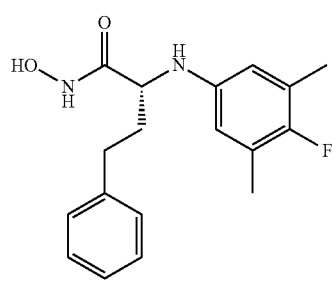

(R)-2-(4-Fluoro-3,5-dimethyl-phenylamino)-N-hydroxy-4-phenyl-butyramide (Compound 167406) Prepared According to General Scheme 2 or 3

LC-MS: $t_R$=7.6 min, m/z 317 (M+H)$^+$.

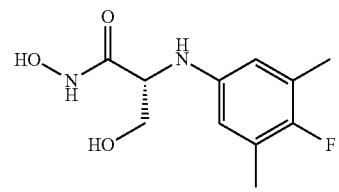

(R)-2-(4-Fluoro-3,5-dimethyl-phenylamino)-3,N-dihydroxy-propionamide (Compound 167485) Prepared According to General Scheme 2 or 3

LC-MS: $t_R$=4.2 min, m/z 243 (M+H)$^+$.

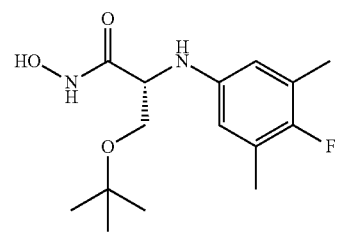

(R)-3-tert-Butoxy-2-(4-fluoro-3,5-dimethyl-phenylamino)-N-hydroxy-propionamide (Compound 167484) Prepared According to General Scheme 2 or 3

LC-MS: $t_R$=7.0 min, m/z 299 (M+H)$^+$.

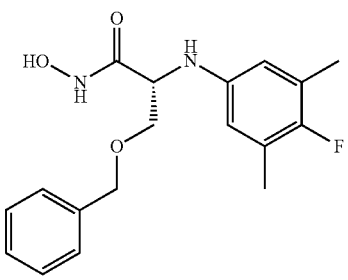

(R)-3-Benzyloxy-2-(4-fluoro-3,5-dimethyl-phenylamino)-N-hydroxy-propionamide (Compound 167379) Prepared According to General Scheme 2 or 3

LC-MS: $t_R$=7.4 min, m/z 333 (M+H)$^+$.

Table 3 Compounds

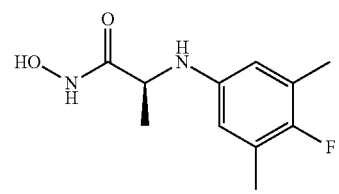

(S)-2-(4-Fluoro-3,5-dimethyl-phenylamino)-N-hydroxy-propionamide (Compound 167498) Prepared According to General Scheme 2 or 3

LC-MS: $t_R$=4.4 min, m/z 227 (M+H)$^+$

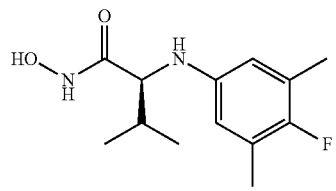

(S)-2-(4-Fluoro-3,5-dimethyl-phenylamino)-N-hydroxy-3-methyl-butyramide (Compound 167296) Prepared According to General Scheme 2 or 3

LC-MS: $t_R$=6.0 min, m/z 255 (M+H)$^+$.

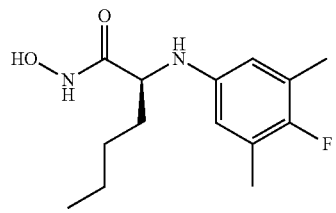

(S)-2-(4-Fluoro-3,5-dimethyl-phenylamino)-hexanoic acid hydroxyamide (Compound 167295) Prepared According to General Scheme 2 or 3

LC-MS: $t_R$=6.7 min, m/z 269 (M+H)$^+$.

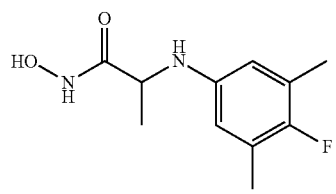

2-(4-Fluoro-3,5-dimethyl-phenylamino)-N-hydroxy-propionamide (Compound 167486) Prepared According to General Scheme 2 or 3

LC-MS: $t_R$=4.4 min, m/z 227 (M+H)$^+$.

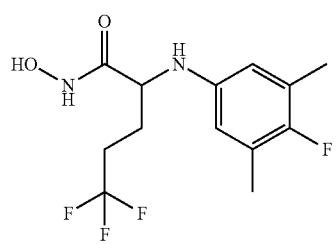

5,5,5-Trifluoro-2-(4-fluoro-3,5-dimethyl-phenylamino)-pentanoic acid hydroxyamide (Compound 167482) Prepared According to General Scheme 2 or 3

LC-MS: $t_R$=7.0 min, m/z 309 (M+H)$^+$.

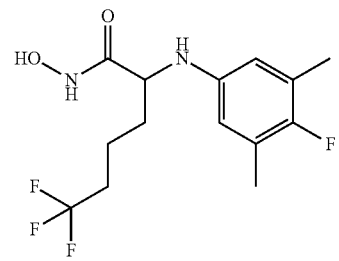

6,6,6-Trifluoro-2-(4-fluoro-3,5-dimethyl-phenylamino)-hexanoic acid hydroxyamide (Compound 167483) Prepared According to General Scheme 2 or 3

LC-MS: $t_R$=7.2 min, m/z 323 (M+H)$^+$.

Table 4 Compounds

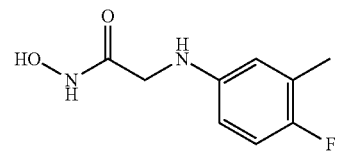

2-(4-Fluoro-3-methyl-phenylamino)-N-hydroxy-acetamide (Compound 167986) Prepared According to General Scheme 2 or 3

LC-MS: $t_R$=3.6 min, m/z 199 (M+H)$^+$.

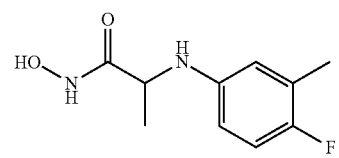

2-(4-Fluoro-3-methyl-phenylamino)-N-hydroxy-propionamide (Compound 167235) Prepared According to General Scheme 2 or 3

LC-MS: $t_R$=3.6 min, m/z 213 (M+H)$^+$.

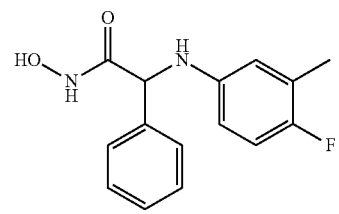

2-(4-Fluoro-3-methyl-phenylamino)-N-hydroxy-2-phenyl-acetamide (Compound 167228) Prepared According to General Scheme 2 or 3

LC-MS: $t_R$=6.2 min, m/z 275 (M+H)$^+$.

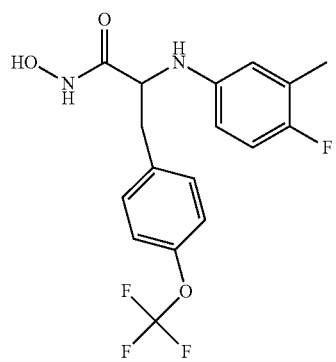

2-(4-Fluoro-3-methyl-phenylamino)-N-hydroxy-3-(4-trifluoromethoxy-phenyl)-propionamide (Compound 167233) Prepared According to General Scheme 2 or 3

LC-MS: $t_R$=7.8 min, m/z 373 (M+H)$^+$.

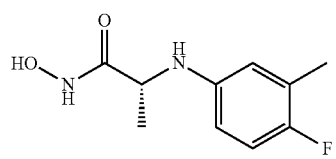

(R)-2-(4-Fluoro-3-methyl-phenylamino)-N-hydroxy-propionamide (Compound 167392) Prepared According to General Scheme 2 or 3

LC-MS: $t_R$=3.6 min, m/z 213 (M+H)$^+$.

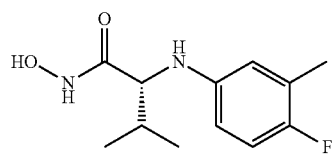

(R)-2-(4-Fluoro-3-methyl-phenylamino)-N-hydroxy-3-methyl-butyramide hydrochloride (Compound 167267) Prepared According to General Scheme 2 or 3

LC-MS: $t_R$=5.4 min, m/z 241 (M+H)$^+$.

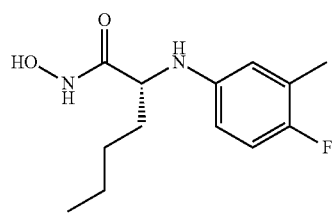

(R)-2-(4-Fluoro-3-methyl-phenylamino)-hexanoic acid hydroxyamide (Compound 167273) Prepared According to General Scheme 2 or 3

LC-MS: $t_R$=6.2 min, m/z 255 (M+H)$^+$.

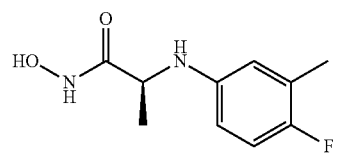

(S)-2-(4-Fluoro-3-methyl-phenylamino)-N-hydroxy-propionamide (Compound 167364) Prepared According to General Scheme 2 or 3

LC-MS: $t_R$=3.6 min, m/z 213 (M+H)$^+$.

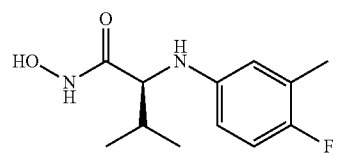

(S)-2-(4-Fluoro-3-methyl-phenylamino)-N-hydroxy-3-methyl-butyramide hydrochloride (Compound 167268) Prepared According to General Scheme 2 or 3

LC-MS: $t_R$=5.4 min, m/z 241 (M+H)$^+$.

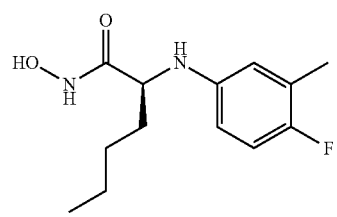

(S)-2-(4-Fluoro-3-methyl-phenylamino)-hexanoic acid hydroxyamide (Compound 167274) Prepared According to General Scheme 2 or 3

LC-MS: $t_R$=6.2 min, m/z 255 (M+H)$^+$.

Table 5 Compounds

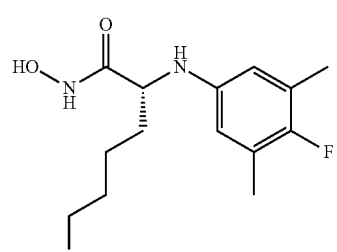

(R)-6-Amino-2-(4-fluoro-3,5-dimethyl-phenylamino)-hexanoic acid hydroxyamide (Compound 167517) Prepared According to General Scheme 4

LC-MS: $t_R$=3.4 min, m/z 284 (M+H)$^+$.

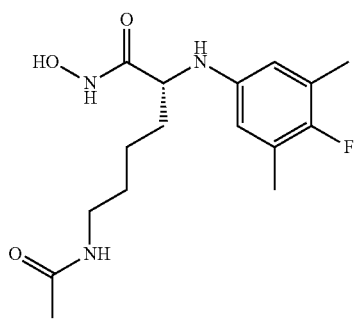

(R)-6-Acetylamino-2-(4-fluoro-3,5-dimethyl-phenylamino)-hexanoic acid hydroxyamide (Compound 167552) Prepared According to General Scheme 4

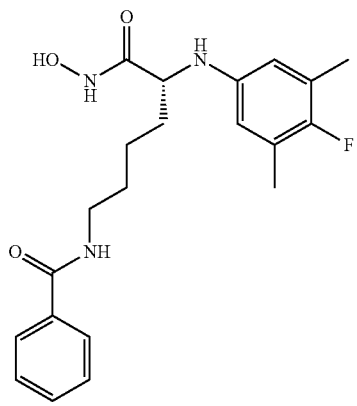

(R)—N-[5-(4-Fluoro-3,5-dimethyl-phenylamino)-5-hydroxycarbamoyl-pentyl]-benzamide (Compound 167587) Prepared According to General Scheme 4

LC-MS: $t_R$=6.2 min, m/z 388 (M+H)$^+$.

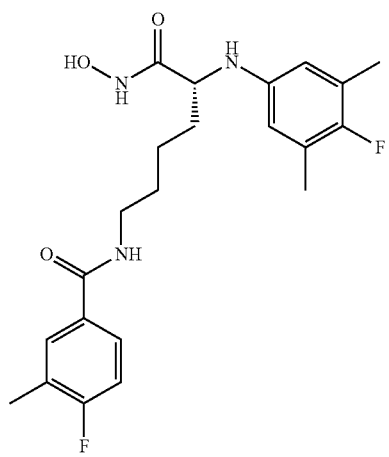

(R)-4-Fluoro-N-[5-(4-fluoro-3,5-dimethyl-phenylamino)-5-hydroxycarbamoyl-pentyl]-3-methyl-benzamide (Compound 167551) Prepared According to General Scheme 4

LC-MS: $t_R$=7.0 min, m/z 420 (M+H)$^+$.

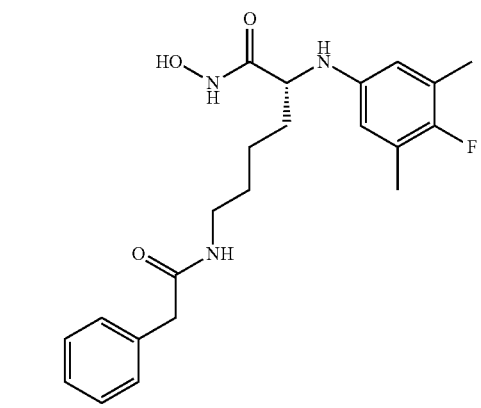

(R)-2-(4-Fluoro-3,5-dimethyl-phenylamino)-6-phenylacetylamino-hexanoic acid hydroxyamide (Compound 167588) Prepared According to General Scheme 4

LC-MS: $t_R$=6.3 min, m/z 402 (M+H)$^+$.

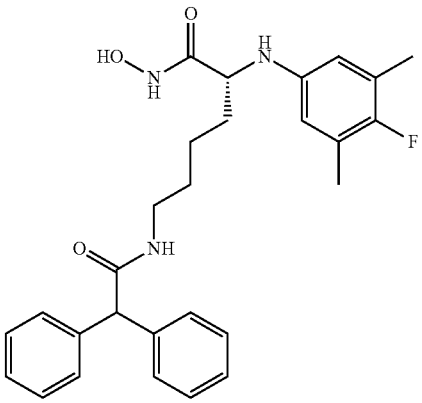

(R)-6-Diphenylacetylamino-2-(4-fluoro-3,5-dimethyl-phenylamino)-hexanoic acid hydroxyamide (Compound 167610) Prepared According to General Scheme 4

LC-MS: $t_R$=7.9 min, m/z 478 (M+H)$^+$.

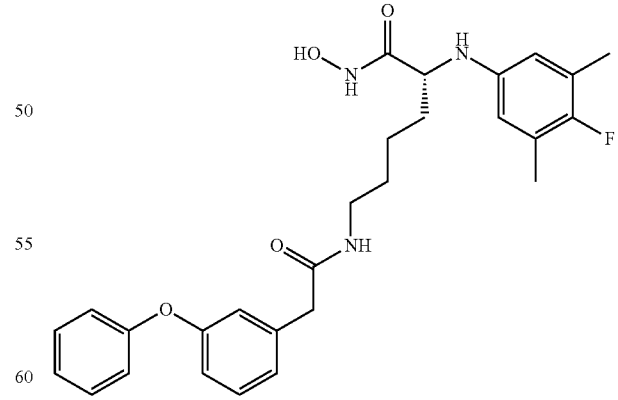

(R)-2-(4-Fluoro-3,5-dimethyl-phenylamino)-6-[2-(3-phenoxy-phenyl)-acetylamino]-hexanoic acid hydroxyamide (Compound 167611) Prepared According to General Scheme 4

LC-MS: $t_R$=7.9 min, m/z 494 (M+H)$^+$.

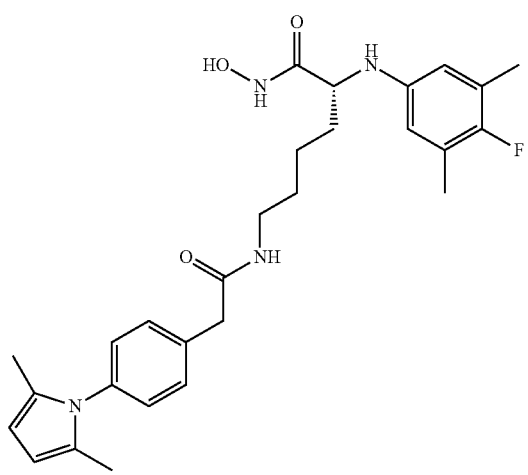

(R)-6-{2-[4-(2,5-Dimethyl-pyrrol-1-yl)-phenyl]-acetylamino}-2-(4-fluoro-3,5-dimethyl-phenylamino)-hexanoic acid hydroxyamide (Compound 167592) Prepared According to General Scheme 4

LC-MS: $t_R$=7.8 min, m/z 495 (M+H)⁺.

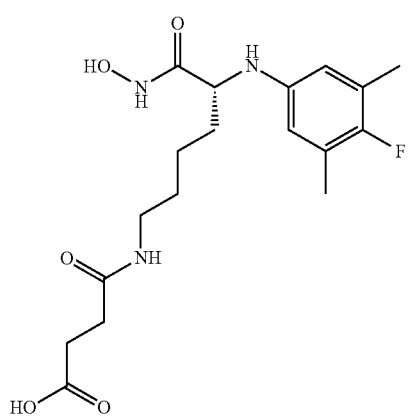

(R)—N-[5-(4-Fluoro-3,5-dimethyl-phenylamino)-5-hydroxycarbamoyl-pentyl]-succinamic acid (Compound 167620) Prepared According to General Scheme 4

LC-MS: $t_R$=4.5 min, m/z 384 (M+H)⁺.

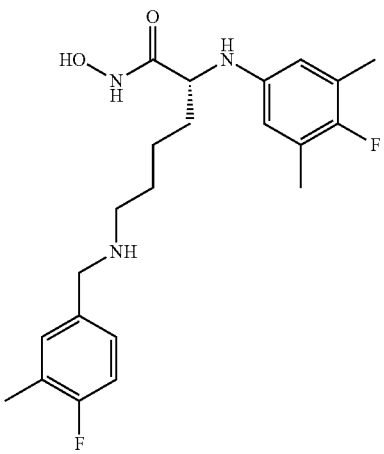

(R)-2-(4-Fluoro-3,5-dimethyl-phenylamino)-6-(4-fluoro-3-methyl-benzylamino)-hexanoic acid hydroxyamide (Compound 167654) Prepared According to General Scheme 4

LC-MS: $t_R$=5.5 min, m/z 406 (M+H)⁺.

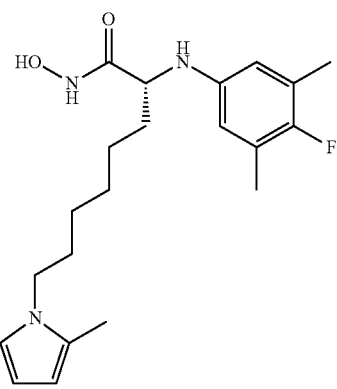

(R)-6-(2,5-Dimethyl-pyrrol-1-yl)-2-(4-fluoro-3,5-dimethyl-phenylamino)-hexanoic acid hydroxyamide (Compound 167605) Prepared According to General Scheme 4

LC-MS: $t_R$=8.0 min, m/z 362 (M+H)⁺.

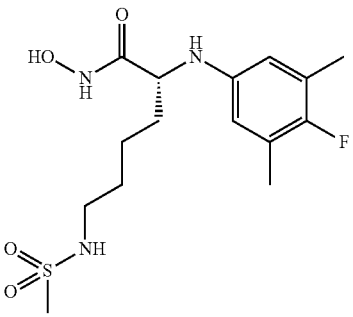

(R)-2-(4-Fluoro-3,5-dimethyl-phenylamino)-6-methanesulfonylamino-hexanoic acid hydroxyamide (Compound 167531) Prepared According to General Scheme 4

LC-MS: $t_R$=5.1 min, m/z 362 (M+H)⁺.

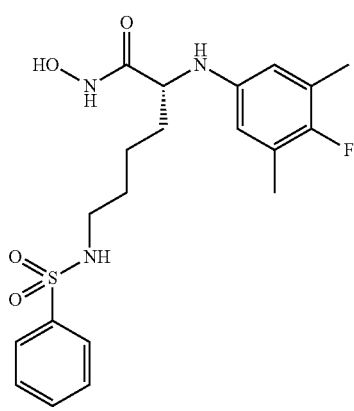

(R)-6-Benzenesulfonylamino-2-(4-fluoro-3,5-dimethyl-phenylamino)-hexanoic acid hydroxyamide (Compound 167615) Prepared According to General Scheme 4

LC-MS: $t_R$=6.8 min, m/z 424 (M+H)$^+$.

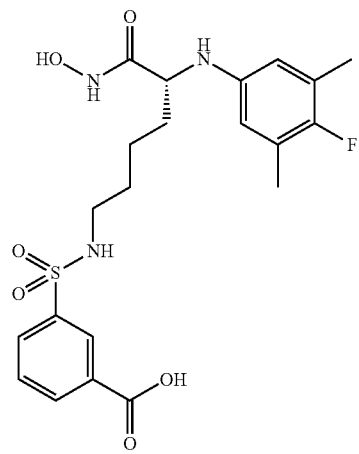

(R)-3-[5-(4-Fluoro-3,5-dimethyl-phenylamino)-5-hydroxycarbamoyl-pentylsulfamoyl]-benzoic acid (Compound 167621) Prepared according to General Scheme 4

LC-MS: $t_R$=6.1 min, m/z 468 (M+H)$^+$.

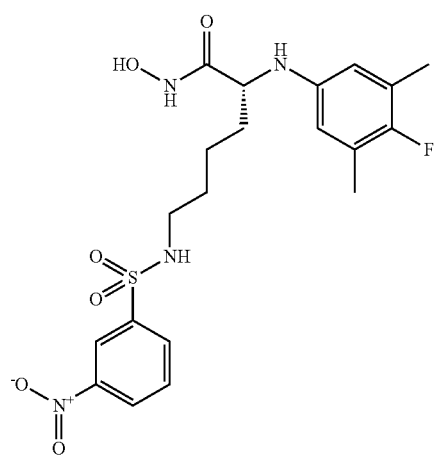

(R)-2-(4-Fluoro-3,5-dimethyl-phenylamino)-6-(3-nitro-benzenesulfonylamino)-hexanoic acid hydroxyamide (Compound 167622) Prepared According to General Scheme 4

LC-MS: $t_R$=7.2 min, m/z 469 (M+H)$^+$.

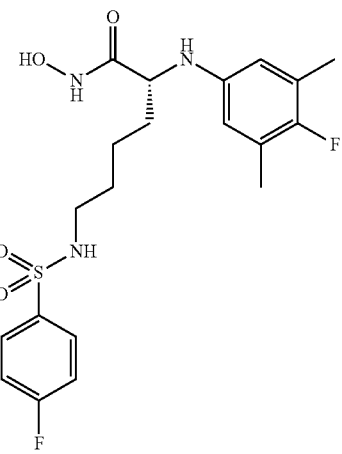

(R)-6-(4-Fluoro-benzenesulfonylamino)-2-(4-fluoro-3,5-dimethyl-phenylamino)-hexanoic acid hydroxyamide (Compound 167589) Prepared According to General Scheme 4

LC-MS: $t_R$=7.0 min, m/z 442 (M+H)$^+$.

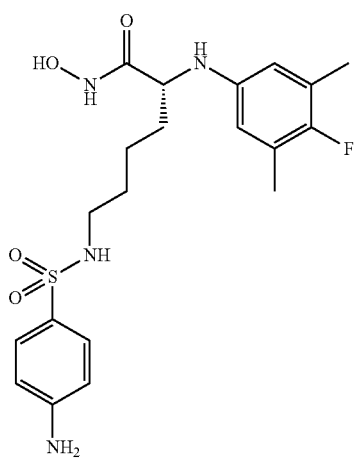

(R)-6-(4-Amino-benzenesulfonylamino)-2-(4-fluoro-3,5-dimethyl-phenylamino)-hexanoic acid hydroxyamide (Compound 167656) Prepared According to General Scheme 4

LC-MS: $t_R$=5.8 min, m/z 439 (M+H)$^+$.

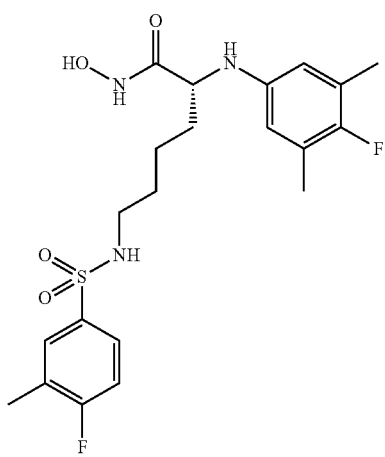

(R)-2-(4-Fluoro-3,5-dimethyl-phenylamino)-6-(4-fluoro-3-methyl-benzenesulfonylamino)-hexanoic acid hydroxyamide (Compound 167590) Prepared According to General Scheme 4

LC-MS: $t_R$=7.5 min, m/z 456 (M+H)$^+$.

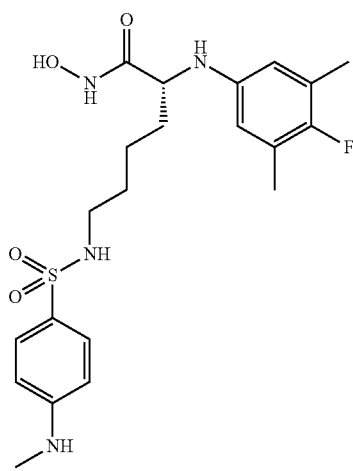

(R)-2-(4-Fluoro-3,5-dimethyl-phenylamino)-6-(4-methylamino-benzenesulfonylamino)-hexanoic acid hydroxyamide (Compound 167657) Prepared According to General Scheme 4

LC-MS: $t_R$=6.5 min, m/z 453 (M+H)$^+$.

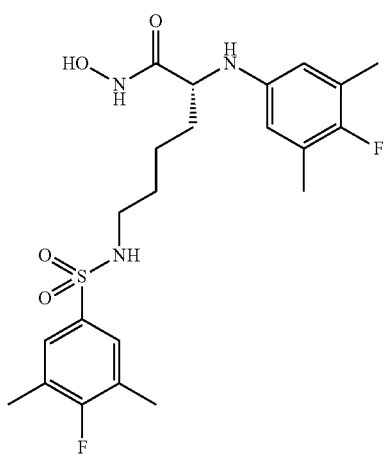

(R)-6-(4-Fluoro-3,5-dimethyl-benzenesulfonylamino)-2-(4-fluoro-3,5-dimethyl-phenylamino)-hexanoic acid hydroxyamide (Compound 167530) Prepared According to General Scheme 4

LC-MS: $t_R$=7.9 min, m/z 470 (M+H)$^+$.

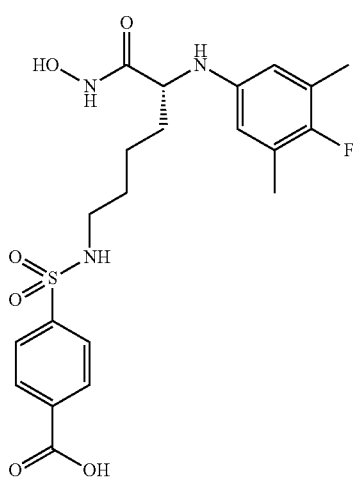

(R)-4-[5-(4-Fluoro-3,5-dimethyl-phenylamino)-5-hydroxycarbamoyl-pentylsulfamoyl]-benzoic acid (Compound 167613) Prepared according to General Scheme 4

LC-MS: $t_R$=6.0 min, m/z 468 (M+H)$^+$.

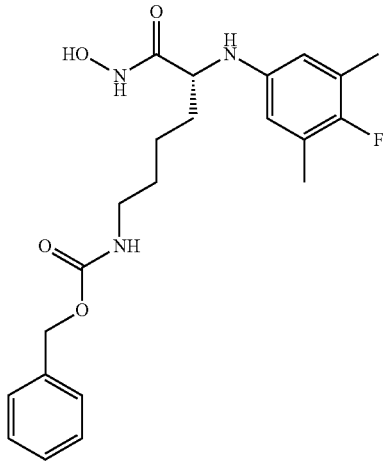

(R)-[5-(4-Fluoro-3,5-dimethyl-phenylamino)-5-hydroxycarbamoyl-pentyl]-carbamic acid benzyl ester (Compound 167503) Prepared According to General Scheme 4

LC-MS: $t_R$=7.3 min, m/z 418 (M+H)$^+$.

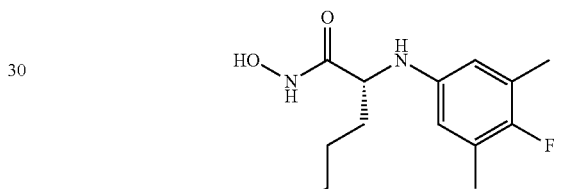

(R)-2-(4-Fluoro-3,5-dimethyl-phenylamino)-6-[3-(4-fluoro-3-methyl-phenyl)-ureido]-hexanoic acid hydroxyamide (Compound 167614) Prepared according to General Scheme 4

LC-MS: $t_R$=7.0 min, m/z 435 (M+H)$^+$.

Table 6 Compounds

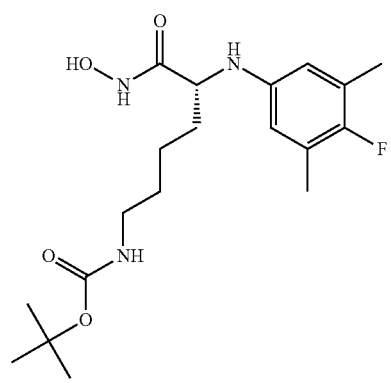

(R)-[5-(4-Fluoro-3,5-dimethyl-phenylamino)-5-hydroxycarbamoyl-pentyl]-carbamic acid tert-butyl ester (Compound 167561) Prepared According to General Scheme 4

LC-MS: $t_R$=7.0 min, m/z 384 (M+H)$^+$.

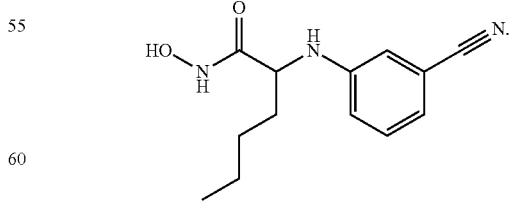

2-(3-Cyano-phenylamino)-hexanoic acid hydroxyamide (Compound 167719) Prepared According to General Scheme 3

LC-MS: $t_R$=5.7 min, m/z 248 (M+H)$^+$.

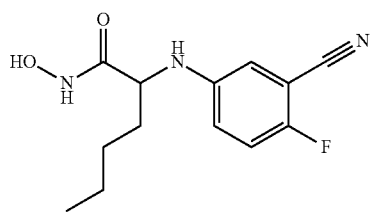

2-(3-Cyano-4-fluoro-phenylamino)-hexanoic acid hydroxyamide (Compound 167720) Prepared According to General Scheme 3

LC-MS: $t_R$=6.1 min, m/z 266 (M+H)$^+$.

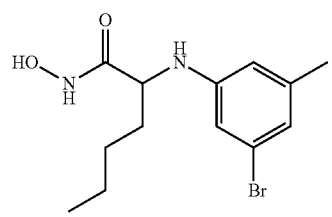

2-(3-Bromo-5-methyl-phenylamino)-hexanoic acid hydroxyamide (Compound 167844) Prepared According to General Scheme 3

LC-MS: $t_R$=7.5 min, m/z 316 (M+H)$^+$.

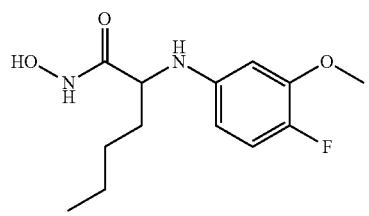

2-(4-Fluoro-3-methoxy-phenylamino)-hexanoic acid hydroxyamide (Compound 167793) Prepared According to General Scheme 3

LC-MS: $t_R$=5.8 min, m/z 271 (M+H)$^+$.

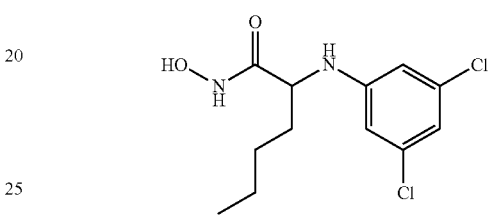

2-(3,5-Dichloro-phenylamino)-hexanoic acid hydroxyamide (Compound 167718) Prepared According to General Scheme 3

LC-MS: $t_R$=7.8 min, m/z 292 (M+H)$^+$.

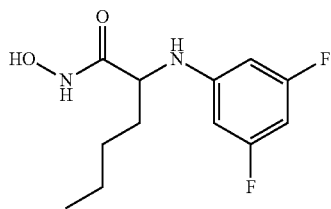

2-(3,5-Difluoro-phenylamino)-hexanoic acid hydroxyamide (Compound 167807) Prepared According to General Scheme 1

LC-MS: $t_R$=6.5 min, m/z 259 (M+H)$^+$.

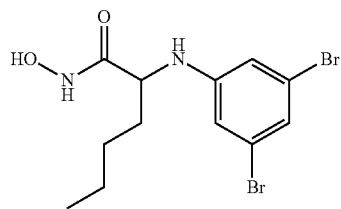

2-(3,5-Dibromo-phenylamino)-hexanoic acid hydroxyamide (Compound 167843) Prepared According to General Scheme 3

LC-MS: $t_R$=8.2 min, m/z 381 (M+H)$^+$.

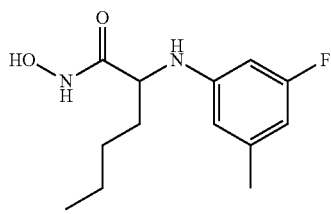

2-(3-Fluoro-5-methyl-phenylamino)-hexanoic acid hydroxyamide (Compound 167722) Prepared According to General Scheme 1

LC-MS: $t_R$=6.7 min, m/z 255 (M+H)$^+$.

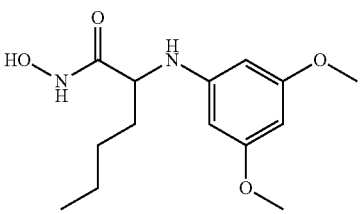

2-(3,5-Dimethoxy-phenylamino)-hexanoic acid hydroxyamide (Compound 167772) Prepared According to General Scheme 1

LC-MS: $t_R$=5.8 min, m/z 283 (M+H)$^+$.

Table 7 Compounds

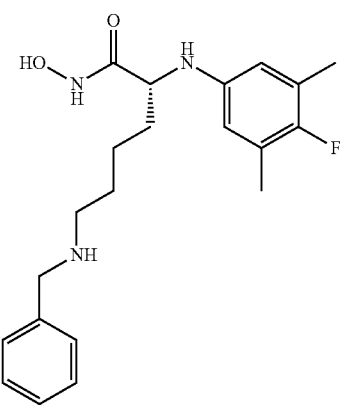

(R)-6-Benzylamino-2-(4-fluoro-3,5-dimethyl-phenylamino)-hexanoic acid hydroxyamide (Compound 167736) Prepared According to General Scheme 4

LC-MS: $t_R$=5.0 min, m/z 374 (M+H)$^+$.

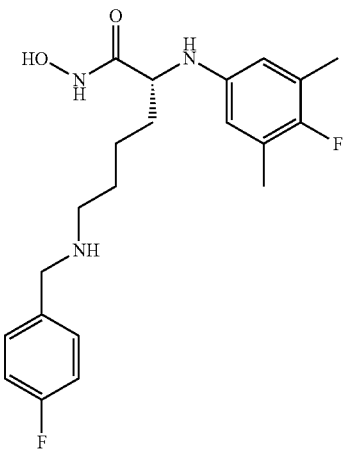

(R)-6-(4-Fluoro-benzylamino)-2-(4-fluoro-3,5-dimethyl-phenylamino)-hexanoic acid hydroxyamide (Compound 168030) Prepared According to General Scheme 4

LC-MS: $t_R$=5.2 min, m/z 392 (M+H)$^+$.

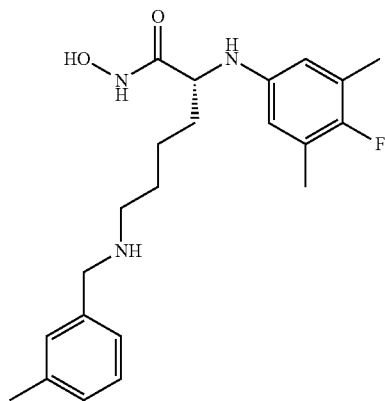

(R)-2-(4-Fluoro-3,5-dimethyl-phenylamino)-6-(3-methyl-benzylamino)-hexanoic acid hydroxyamide (Compound 167698) Prepared According to General Scheme 4

LC-MS: $t_R$=5.4 min, m/z 388 (M+H)$^+$.

6-(4-Fluoro-3,5-dimethyl-benzylamino)-2-(4-fluoro-3,5-dimethyl-phenylamino)-hexanoic acid hydroxyamide (Compound 167759) Prepared According to General Scheme 4

LC-MS: $t_R$=5.9 min, m/z 420 (M+H)$^+$.

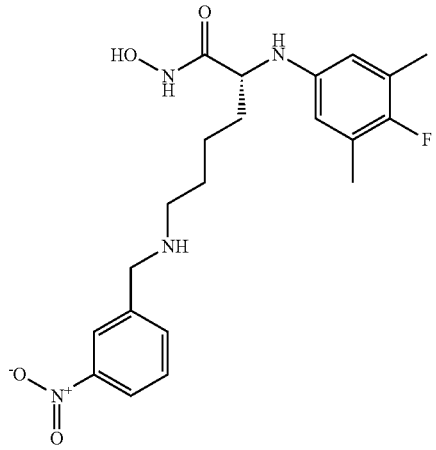

(R)-2-(4-Fluoro-3,5-dimethyl-phenylamino)-6-(3-nitro-benzylamino)-hexanoic acid hydroxyamide (Compound 167737) Prepared According to General Scheme 4

LC-MS: $t_R$=5.1 min, m/z 419 (M+H)$^+$.

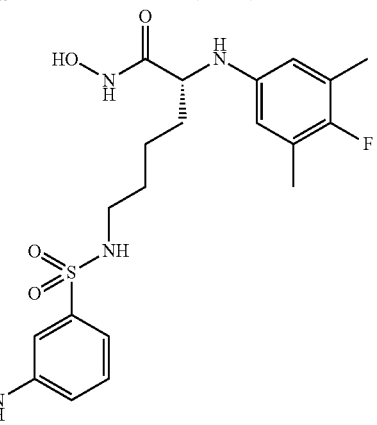

(R)-2-(4-Fluoro-3,5-dimethyl-phenylamino)-6-(3-methylamino-benzenesulfonylamino)-hexanoic acid hydroxyamide (Compound 167667) Prepared According to General Scheme 4

LC-MS: $t_R$=6.5 min, m/z 453 (M+H)$^+$.

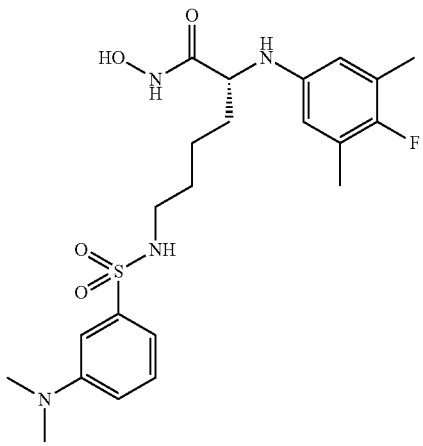

(R)-6-(3-Dimethylamino-benzenesulfonylamino)-2-(4-fluoro-3,5-dimethyl-phenylamino)-hexanoic acid hydroxyamide (Compound 167700) Prepared According to General Scheme 4

LC-MS: $t_R$=7.1 min, m/z 467 (M+H)$^+$.

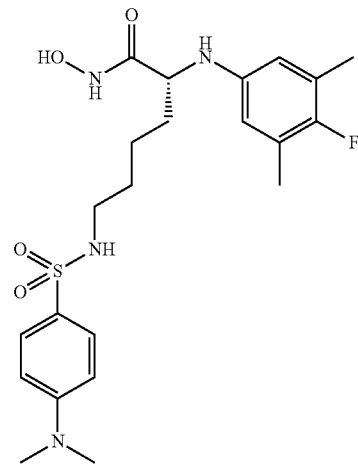

(R)-6-(4-Dimethylamino-benzenesulfonylamino)-2-(4-fluoro-3,5-dimethyl-phenylamino)-hexanoic acid hydroxyamide (Compound 167699) Prepared According to General Scheme 4

LC-MS: $t_R$=7.1 min, m/z 467 (M+H)$^+$.

Table 8 Compounds

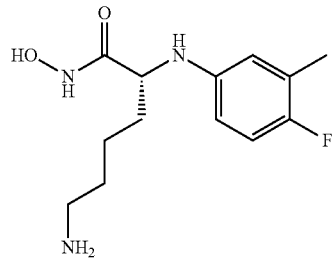

(R)-6-Amino-2-(4-fluoro-3-methyl-phenylamino)-hexanoic acid hydroxyamide (Compound 167949) Prepared According to General Scheme 4

LC-MS: $t_R$=2.1 min, m/z 270 (M+H)$^+$.

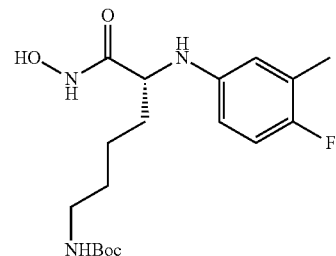

(R)-[5-(4-Fluoro-3-methyl-phenylamino)-5-hydroxy-carbamoyl-pentyl]-carbamic acid tert-butyl ester (Compound 167926) Prepared According to General Scheme 4

LC-MS: $t_R$=6.6 min, m/z 370 (M+H)$^+$.

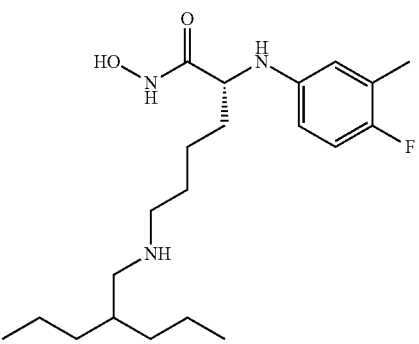

(R)-2-(4-Fluoro-3-methyl-phenylamino)-6-(2-propyl-pentylamino)-hexanoic acid hydroxyamide (Compound 168167) Prepared According to General Scheme 4

LC-MS: $t_R$=5.5 min, m/z 382 (M+H)$^+$.

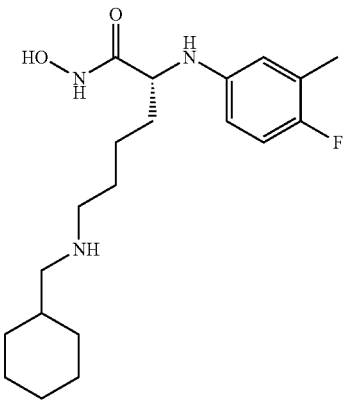

(R)-6-(Cyclohexylmethyl-amino)-2-(4-fluoro-3-methyl-phenylamino)-hexanoic acid hydroxyamide (Compound 168146) Prepared According to General Scheme 4

LC-MS: $t_R$=4.6 min, m/z 366 (M+H)$^+$.

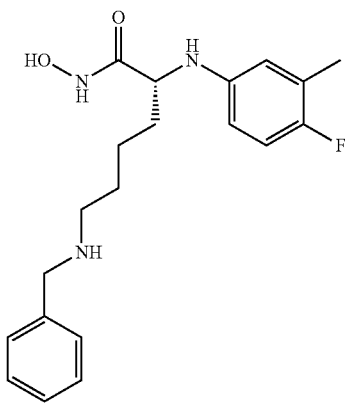

(R)-6-Benzylamino-2-(4-fluoro-3-methyl-phenylamino)-hexanoic acid hydroxyamide (Compound 167980) Prepared According to General Scheme 4

LC-MS: $t_R$=4.5 min, m/z 360 (M+H)$^+$.

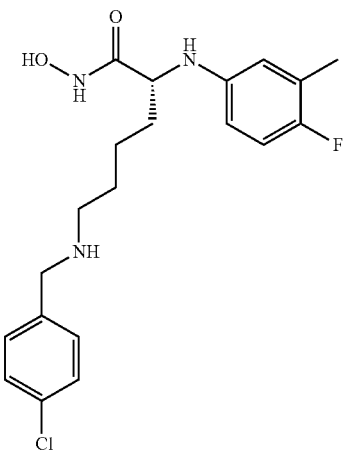

(R)-6-(4-Chloro-benzylamino)-2-(4-fluoro-3-methyl-phenylamino)-hexanoic acid hydroxyamide (Compound 168181) Prepared According to General Scheme 4

LC-MS: $t_R$=4.7 min, m/z 394 (M+H)$^+$.

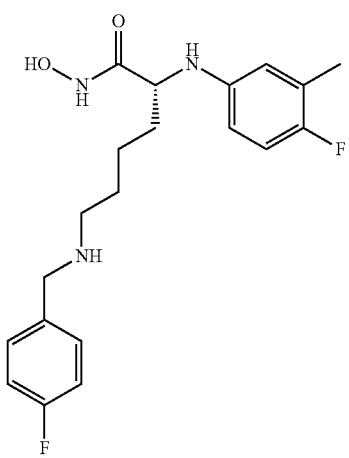

(R)-6-(4-Fluoro-benzylamino)-2-(4-fluoro-3-methyl-phenylamino)-hexanoic acid hydroxyamide (Compound 167945) Prepared According to General Scheme 4

LC-MS: $t_R$=4.8 min, m/z 378 (M+H)$^+$.

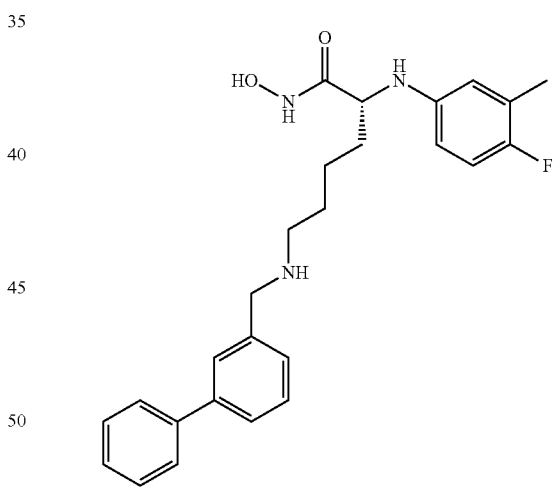

(R)-6-[(Biphenyl-3-ylmethyl)-amino]-2-(4-fluoro-3-methyl-phenylamino)-hexanoic acid hydroxyamide (Compound 168165) Prepared According to General Scheme 4

LC-MS: $t_R$=5.6 min, m/z 436 (M+H)$^+$.

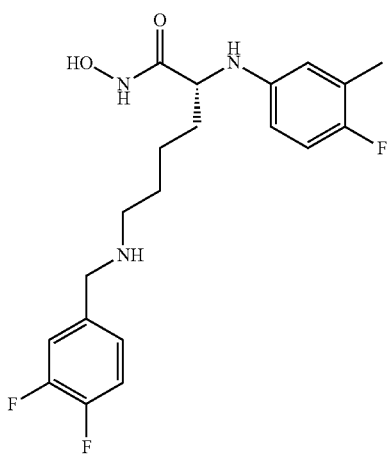

(R)-6-(3,4-Difluoro-benzylamino)-2-(4-fluoro-3-methyl-phenylamino)-hexanoic acid hydroxyamide (Compound 167990) Prepared According to General Scheme 4

LC-MS: $t_R$=5.0 min, m/z 396 (M+H)$^+$.

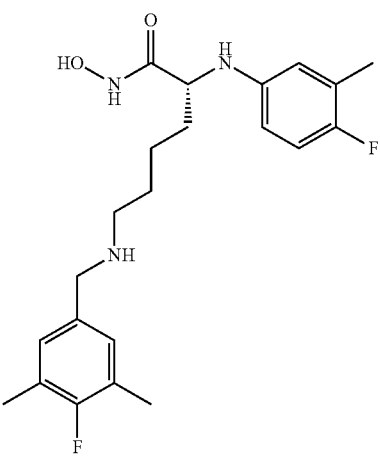

(R)-6-(4-Fluoro-3,5-dimethyl-benzylamino)-2-(4-fluoro-3-methyl-phenylamino)-hexanoic acid hydroxyamide (Compound 167968) Prepared According to General Scheme 4

LC-MS: $t_R$=5.6 min, m/z 406 (M+H)$^+$.

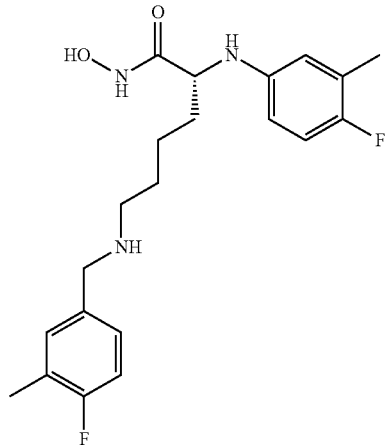

(R)-6-(4-Fluoro-3-methyl-benzylamino)-2-(4-fluoro-3-methyl-phenylamino)-hexanoic acid hydroxyamide (Compound 167946) Prepared According to General Scheme 4

LC-MS: $t_R$=5.2 min, m/z 392 (M+H)$^+$.

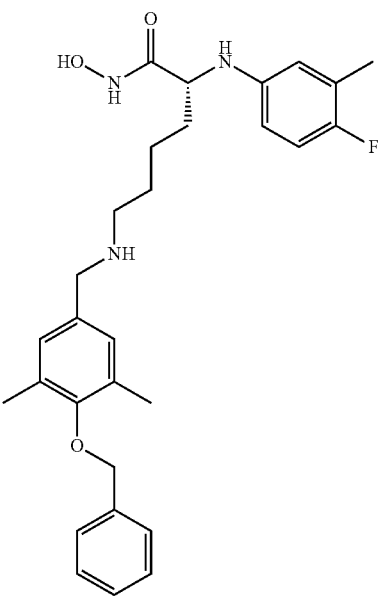

(R)-6-(4-Benzyloxy-3,5-dimethyl-benzylamino)-2-(4-fluoro-3-methyl-phenylamino)-hexanoic acid hydroxyamide (Compound 167969) Prepared According to General Scheme 4

LC-MS: $t_R$=6.7 min, m/z 494 (M+H)$^+$.

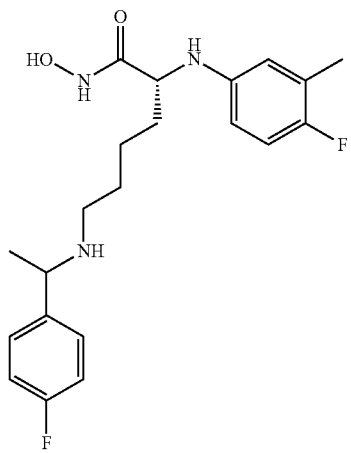

(R)-2-(4-Fluoro-3-methyl-phenylamino)-6-[1-(4-fluoro-phenyl)-ethylamino]-hexanoic acid hydroxyamide (Compound 168010) Prepared According to General Scheme 4

LC-MS: $t_R$=5.1 min, m/z 392 (M+H)$^+$.

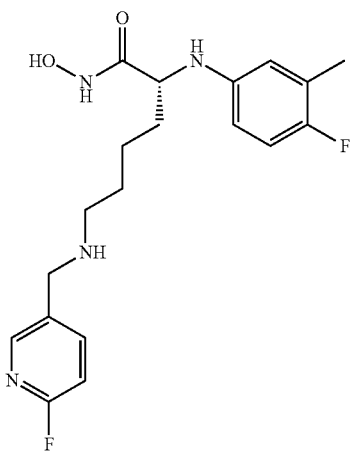

(R)-2-(4-Fluoro-3-methyl-phenylamino)-6-[(6-fluoro-pyridin-3-ylmethyl)-amino]-hexanoic acid hydroxyamide (Compound 167978) Prepared according to General Scheme 4

LC-MS: $t_R$=4.0 min, m/z 379 (M+H)$^+$.

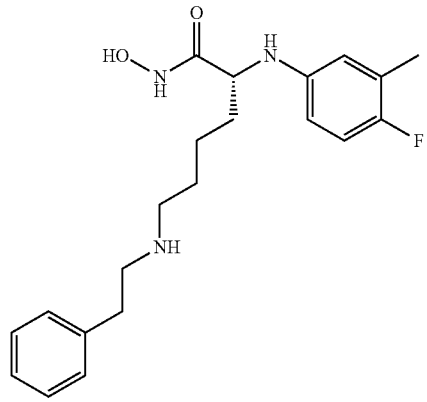

(R)-2-(4-Fluoro-3-methyl-phenylamino)-6-phenethylamino-hexanoic acid hydroxyamide (Compound 167979) Prepared According to General Scheme 4

LC-MS: $t_R$=5.1 min, m/z 374 (M+H)$^+$.

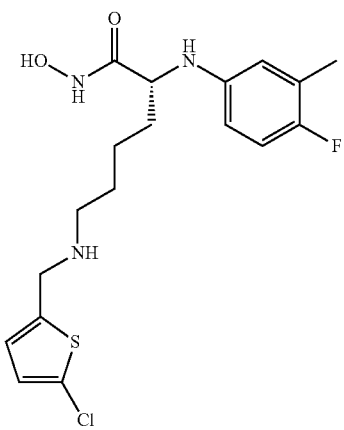

(R)-6-[(5-Chloro-thiophen-2-ylmethyl)-amino]-2-(4-fluoro-3-methyl-phenylamino)-hexanoic acid hydroxyamide (Compound 168008) Prepared According to General Scheme 4

LC-MS: $t_R$=5.1 min, m/z 400 (M+H)$^+$.

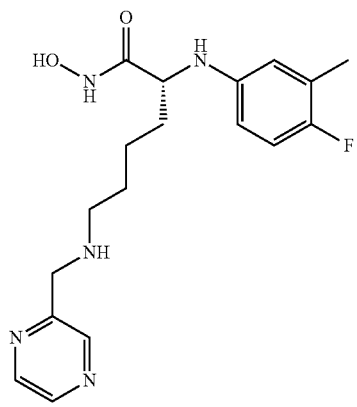

(R)-2-(4-Fluoro-3-methyl-phenylamino)-6-[(pyrazin-2-ylmethyl)-amino]-hexanoic acid hydroxyamide (Compound 168168) Prepared According to General Scheme 4

LC-MS: $t_R$=1.8 min, m/z 362 (M+H)⁺.

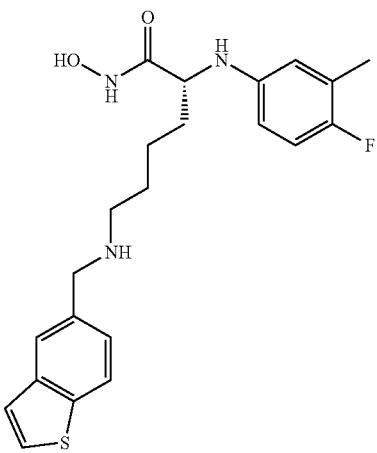

(R)-6-[(Benzo[b]thiophen-5-ylmethyl)-amino]-2-(4-fluoro-3-methyl-phenylamino)-hexanoic acid hydroxyamide (Compound 168182) Prepared According to General Scheme 4

LC-MS: $t_R$=4.8 min, m/z 416 (M+H)⁺.

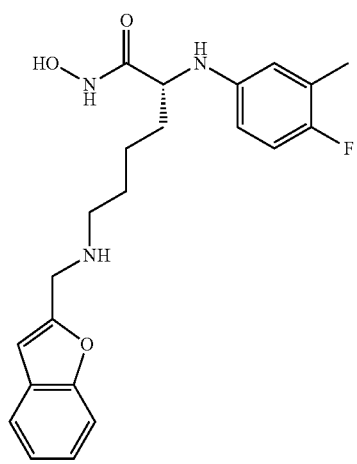

(R)-6-[(Benzofuran-2-ylmethyl)-amino]-2-(4-fluoro-3-methyl-phenylamino)-hexanoic acid hydroxyamide (Compound 168166) Prepared According to General Scheme 4

LC-MS: $t_R$=4.7 min, m/z 400 (M+H)⁺.

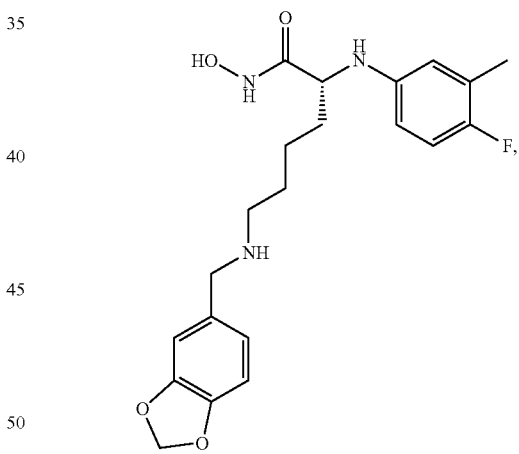

(R)-6-[(Benzo[1,3]dioxol-5-ylmethyl)-amino]-2-(4-fluoro-3-methyl-phenylamino)-hexanoic acid hydroxyamide (Compound 168145) Prepared According to General Scheme 4

LC-MS: $t_R$=4.2 min, m/z 404 (M+H)⁺.

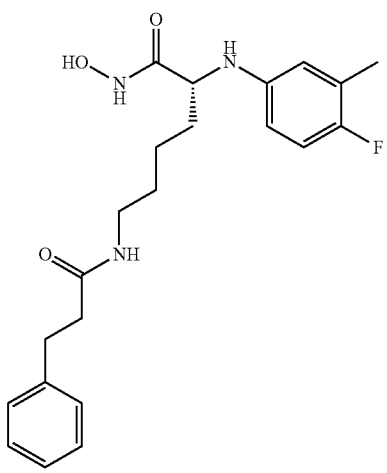

(R)-2-(4-Fluoro-3-methyl-phenylamino)-6-(3-phenyl-propionylamino)-hexanoic acid hydroxyamide (Compound 167993) Prepared According to General Scheme 4

LC-MS: $t_R$=6.3 min, m/z 402 (M+H)$^+$.

Table 9 Compounds

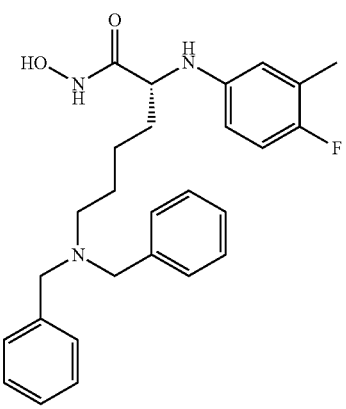

(R)-6-Dibenzylamino-2-(4-fluoro-3-methyl-phenylamino)-hexanoic acid hydroxyamide (Compound 167982) Prepared According to General Scheme 4

LC-MS: $t_R$=6.3 min, m/z 450 (M+H)$^+$.

(R)-2-(4-Fluoro-3-methyl-phenylamino)-6-(4-phenyl-butyrylamino)-hexanoic acid hydroxyamide (Compound 167994) Prepared According to General Scheme 4

LC-MS: $t_R$=6.8 min, m/z 416 (M+H)$^+$.

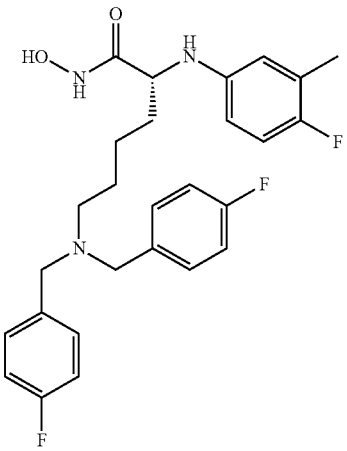

(R)-6-[Bis-(4-fluoro-benzyl)-amino]-2-(4-fluoro-3-methyl-phenylamino)-hexanoic acid hydroxyamide (Compound 167963) Prepared According to General Scheme 4

LC-MS: $t_R$=6.6 min, m/z 486 (M+H)$^+$.

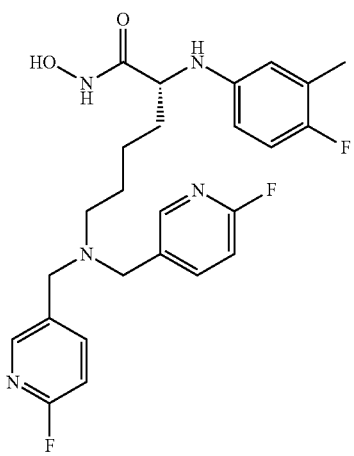

(R)-6-[Bis-(6-fluoro-pyridin-3-ylmethyl)-amino]-2-(4-fluoro-3-methyl-phenylamino)-hexanoic acid hydroxyamide (Compound 168080) Prepared According to General Scheme 4

LC-MS: $t_R$=5.2 min, m/z 488 (M+H)$^+$.

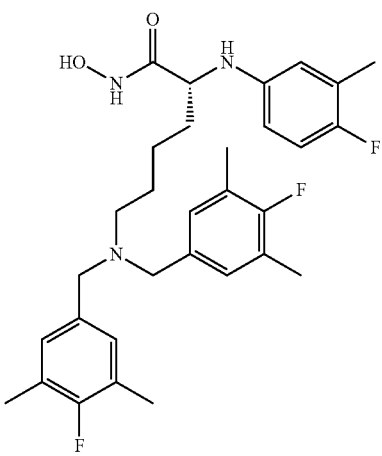

(R)-6-[Bis-(4-fluoro-3,5-dimethyl-benzyl)-amino]-2-(4-fluoro-3-methyl-phenylamino)-hexanoic acid hydroxyamide (Compound 167971) Prepared According to General Scheme 4

LC-MS: $t_R$=7.8 min, m/z 542 (M+H)$^+$.

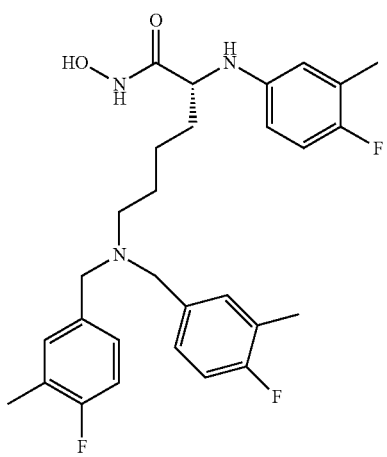

(R)-6-[Bis-(4-fluoro-3-methyl-benzyl)-amino]-2-(4-fluoro-3-methyl-phenylamino)-hexanoic acid hydroxyamide (Compound 167966) Prepared According to General Scheme 4

LC-MS: $t_R$=7.1 min, m/z 471 (M+H)$^+$.

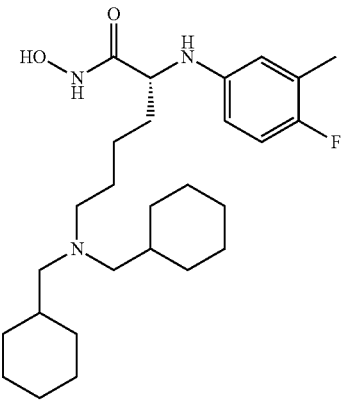

(R)-6-(Bis-cyclohexylmethyl-amino)-2-(4-fluoro-3-methyl-phenylamino)-hexanoic acid hydroxyamide (Compound 167991) Prepared According to General Scheme 4

LC-MS: $t_R$=7.3 min, m/z 462 (M+H)$^+$.

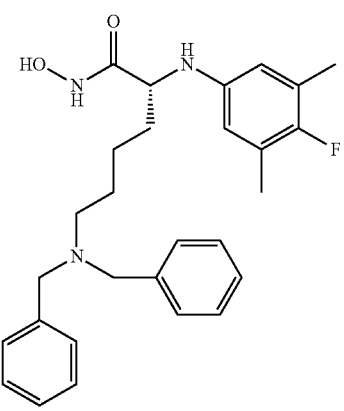

(R)-6-Dibenzylamino-2-(4-fluoro-3,5-dimethyl-phenylamino)-hexanoic acid hydroxyamide (PT_167738) Prepared According to General Scheme 4

LC-MS: $t_R$=6.1 min, m/z 464 (M+H)$^+$.

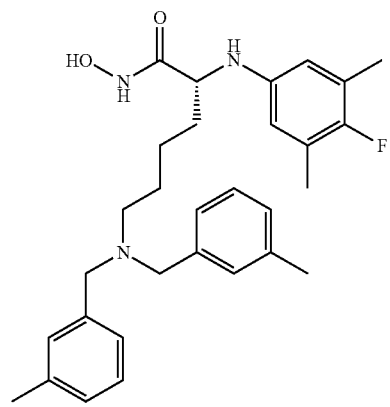

(R)-6-[Bis-(3-methyl-benzyl)-amino]-2-(4-fluoro-3,5-dimethyl-phenylamino)-hexanoic acid hydroxyamide (Compound 167932) Prepared According to General Scheme 4

LC-MS: $t_R$=7.2 min, m/z 492 (M+H)$^+$.

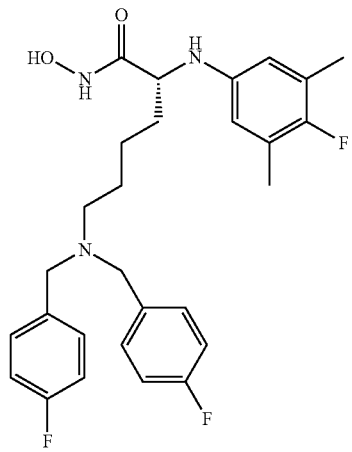

(R)-2-(4-Fluoro-3,5-dimethyl-phenylamino)-8-(4-fluoro-3-methyl-phenyl)-octanoic acid hydroxyamide (Compound 168118) Prepared According to General Scheme 6

LC-MS: $t_R$=10.4 min, m/z 405 (M+H)$^+$.

(R)-6-[Bis-(4-fluoro-benzyl)-amino]-2-(4-fluoro-3,5-dimethyl-phenylamino)-hexanoic acid hydroxyamide (Compound 168047) Prepared According to General Scheme 4

LC-MS: $t_R$=6.9 min, m/z 500 (M+H)$^+$.

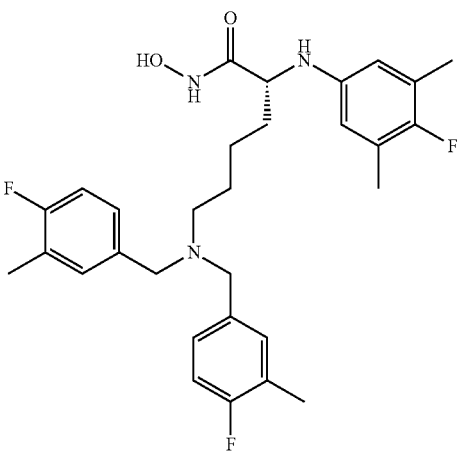

(R)-6-[Bis-(4-fluoro-3-methyl-benzyl)-amino]-2-(4-fluoro-3,5-dimethyl-phenylamino)-hexanoic acid hydroxyamide (Compound 167933) Prepared According to General Scheme 4

LC-MS: $t_R$=7.5 min, m/z 528 (M+H)$^+$.

Table 10 Compounds

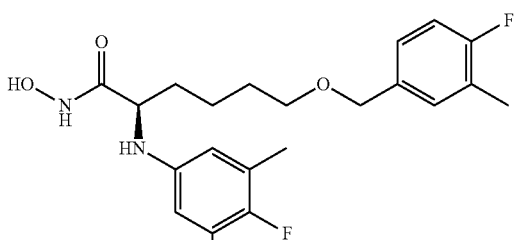

(R)-2-(4-Fluoro-3,5-dimethyl-phenylamino)-6-(4-fluoro-3-methyl-benzyloxy)-hexanoic acid hydroxyamide (Compound 168116) Prepared According to General Scheme 5

LC-MS: $t_R$=8.9 min, m/z 407 (M+H)$^+$.

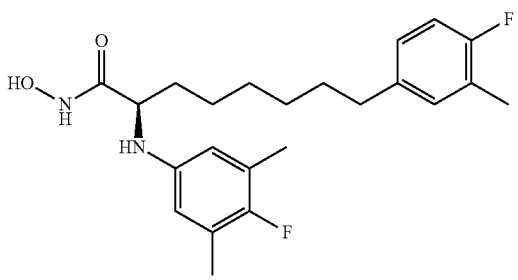

(R)-2-(4-Fluoro-3,5-dimethyl-phenylamino)-8-(4-fluoro-3-methyl-phenyl)-octanoic acid hydroxyamide (Compound 168118) Prepared According to General Scheme 6

LC-MS: $t_R$=10.4 min, m/z 405 (M+H)$^+$.

Table 11 Compounds

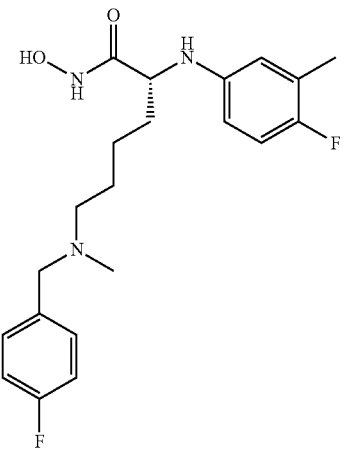

(R)-6-[(4-Fluoro-benzyl)-methyl-amino]-2-(4-fluoro-3-methyl-phenylamino)-hexanoic acid hydroxyamide (Compound 167147) Prepared According to General Scheme 4

LC-MS: $t_R$=4.4 min, m/z 392 (M+H)$^+$.

What is claimed is:

1. A compound of the formula

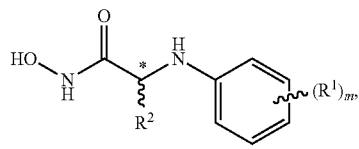

where

R$^1$ is F, Cl, Br, I, alkyl of 1-3 carbons, alkoxy of 1-3 carbons, thioalkoxy of 1-3 carbons, phenyl, O-phenyl, CN, CF$_3$, OCF$_3$, OH, NH$_2$, NHC$_1$—C$_6$alkyl, N(C$_1$-C$_6$ alkyl)$_2$, CO$_2$H or CO$_2$(C$_1$-C$_6$ alkyl);

m is an integer having the value of 1 to 3;

R$^2$ is (CH$_2$)$_n$NHR$^4$ where n is the integer 3, 4, 5 or 6 and R$^4$ is H, C(O)CH$_3$, or R$^4$ is C(O) phenyl, where the phenyl group is substituted with a phenoxy group or 1, 2 or 3 R$^1$ groups, or R$^4$ is C(O)CH$_2$phenyl, CH$_2$-phenyl-phenyl, (CH$_2$)phenyl, C(O)(CH$_2$)$_2$COOH, dimethyl substituted pyrrolyl, SO$_2$-alkyl of 1 to 3 carbons, SO$_2$-phenyl where the phenyl is substituted with a nitro (NO$_2$) group or with 1, 2 or 3 R$^1$ groups, or R$^4$ is C(O)CH$_2$-(3-PhO)Ph, or R$^4$ is cyclohexyl or 2-F-pyridyl; or R$^2$ is (CH$_2$)$_4$OCH$_2$-phenyl where the phenyl is substituted with 1 or 2 R$^1$ groups, or R$^2$ is (CH$_2$)$_6$CH$_2$phenyl where the phenyl is substituted with 1 or 2 R$^1$ groups;

the star indicates an asymmetric carbon, the wavy line represents a bond which can be of either R or S configuration, or a pharmaceutically acceptable salt of said compound.

2. A compound in accordance with claim 1, where m is 2, one R$^1$ group is methyl in the 3 (meta) position on the phenyl ring relative to the NH group, and the other R$^1$ group is fluoro in the 4 (para) position of the phenyl ring relative to the NH group.

3. A compound of the formula

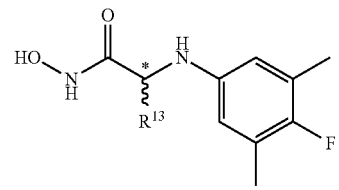

where R$^{13}$ is (CH$_2$)$_s$NR$^{14}$R$^{15}$;

s is an integer selected from 1 to 6;

R$^{14}$ is H or alkyl of 1 to 6 carbons;

R$^{15}$ is selected from the group consisting of H, Ac, C(O)-Ph, C(O)-(3-Me-4-F-Ph), C(O)—CH$_2$Ph, C(O)CH(Ph)$_2$, C(O)CH$_2$-(3-PhO)Ph, C(O)CH$_2$-4-(2,5-di-Me-pyrrol-1-yl)-Ph, C(O)CH$_2$CH$_2$CO$_2$H, CH$_2$-(3-Me-4-F-Ph), 2,5-di-Me-pyrrol-1-yl, SO$_2$Me, SO$_2$Ph, NO$_2$-Ph, SO$_2$-(3-CO$_2$H-Ph), SO$_2$-(4-F-Ph), SO$_2$-(4-NH$_2$-Ph), SO$_2$-(4-MeNH-Ph), NHSO$_2$-(3-Me-4-F-Ph), SO$_2$-(3,5-di-Me-4-F-Ph), SO$_2$-(4-CO$_2$H-Ph), C(O)OtBu, C(O)OCH$_2$Ph, and C(O)NHCH$_2$-(3-Me-4-F-Ph);

the asterisk represents that the adjacent carbon is asymmetric and the wavy line represents a bond which can be of either R or S configuration, or a pharmaceutically acceptable salt of said compound.

4. A compound in accordance with claim 3, where R$^{14}$ is H.

5. A compound in accordance with claim 3, where s is 4.

6. A compound of the formula

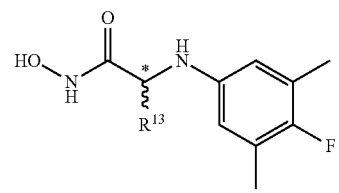

where R$^{13}$ is (CH$_2$)$_s$NR$^{14}$R$^{15}$;

s is an integer selected from 1 to 6;

R$^{14}$ is H or alkyl of 1 to 6 carbons;

R$^{15}$ is selected from the group consisting of CH$_2$phenyl, CH$_2$-(3-Me-phenyl), CH$_2$-(3-NO$_2$-phenyl), CH$_2$-(4-F-phenyl), SO$_2$-(3-MeNH-phenyl), SO$_2$-(3-di-MeN-phenyl), SO$_2$-(4-di-MeN-Ph), C(O)CH$_2$-(3-PhO)phenyl, phenyl, 4-F-phenyl, 5-(2-F-pyridyl), 3 Me-4-F-phenyl, 3,5-di-Me-4-F-phenyl, cyclohexyl, and 3-Me-phenyl;

the asterisk represents that the adjacent carbon is asymmetric and the wavy line represents a bond which can be of either R or S configuration, or a pharmaceutically acceptable salt of said compound.

7. A compound in accordance with claim 6, where R$^{14}$ is H.

8. A compound in accordance with claim 6, where s is 4.

9. A compound of the formula

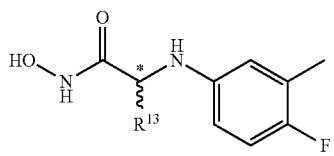

where $R^{13}$ is $(CH_2)_s NR^{14}R^{15}$;
s is an integer selected from 1 to 6;
$R^{14}$ is H or alkyl of 1 to 6 carbons;
$R^{15}$ is selected from the group consisting of H, C(O)OtBu, CH$_2$-phenyl, CH$_2$-(4F-phenyl), CH$_2$-(3,4-di-F-phenyl), CH$_2$-(3-Me-4-F-phenyl), CH$_2$-(3,5-di-Me-4-F-phenyl), CH$_2$-3,5-di-Me-4-(OCH$_2$PH)-Ph, CH$_2$-5-(2-F-pyridyl), CH$_2$-(5-Cl-thienyl), CH(Me)-4-F-phenyl, CH$_2$CH$_2$-phenyl, C(O)(CH$_2$)$_2$-phenyl and C(O)(CH$_2$)$_3$-phenyl;
the asterisk represents that the adjacent carbon is asymmetric and the wavy line represents a bond which can be of either R or S configuration,
or a pharmaceutically acceptable salt of said compound.

10. A compound in accordance with claim 9, where $R^{14}$ is H.

11. A compound in accordance with claim 9, where s is 4.

12. A compound selected from the group of compounds consisting of

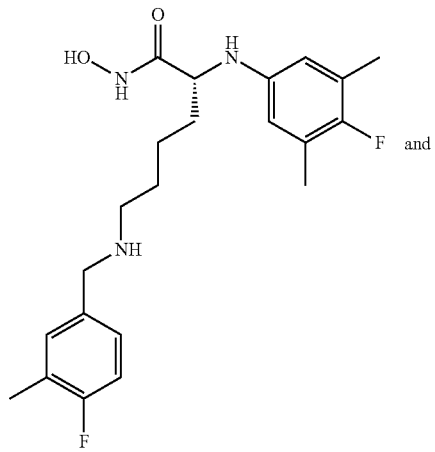 and

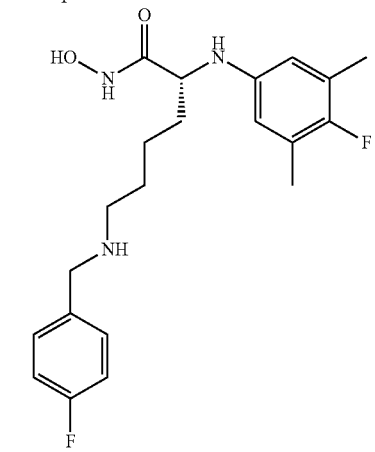

or a pharmaceutically acceptable salt of said compound.

13. A compound selected from the group of compounds consisting of

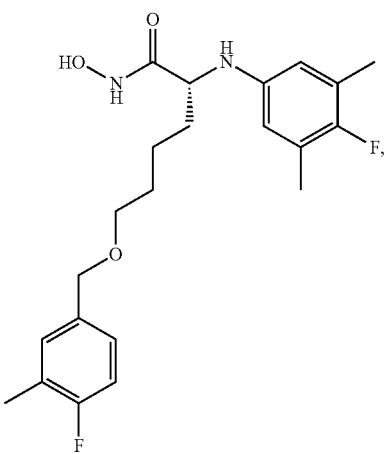

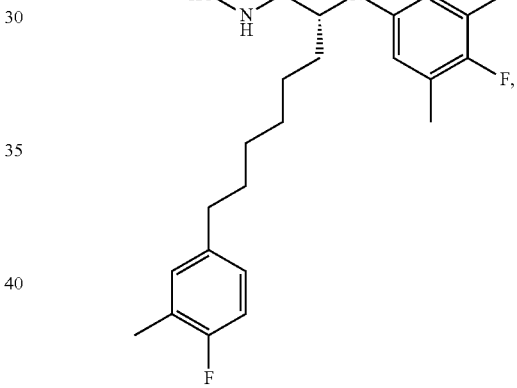

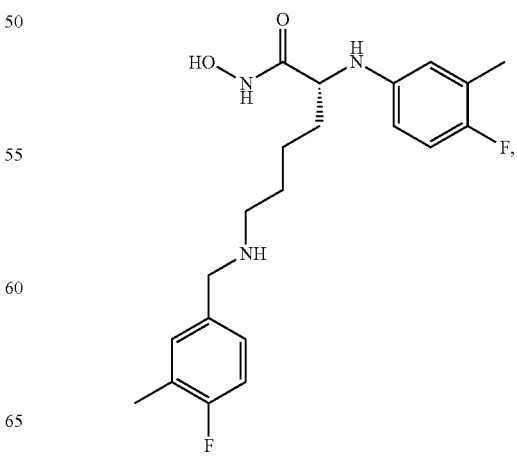

-continued

[Chemical structure: hydroxamic acid with (S)-stereocenter, N-linked to 4-fluoro-3-methylphenyl group, with side chain terminating in NH-CH(CH3)-(4-fluorophenyl)] and

[Chemical structure: hydroxamic acid with (S)-stereocenter, N-linked to 4-fluoro-3-methylphenyl group, with side chain terminating in NH-CH2-(5-chlorothiophen-2-yl)]

or a pharmaceutically acceptable salt of said compound.

14. A compound of the formula

[Chemical structure with hydroxamic acid, asymmetric carbon (*), N-linked to phenyl group bearing F, methyl, and $R^1$ substituents, with side chain terminating in $N(R^{14})_2$]

where $R^1$ is H or alkyl of 1 to 3 carbons;
$R^{14}$ is alkylcyclohexyl, alklylpyridyl or alkylphenyl where the pyridyl and phenyl groups are substituted with 0 to 3 groups independently selected from the group consisting of methyl and fluoro; the asterisk represents that the adjacent carbon is asymmetric and the wavy line represents a bond which can be of either R or S configuration, or a pharmaceutically acceptable salt of said compound.

15. A pharmaceutical composition for the treatment of infection by *bacillus anthraci* in a mammal, said pharmaceutical composition is adapted for systemic administration and comprising a pharmaceutically acceptable excipient and one or more compounds in accordance with claim 1.

16. A method of treating infection of a mammal by *bacillus anthraci*, comprising administering to said mammal a pharmaceutical composition comprising a pharmaceutically acceptable excipient and one or more compounds in accordance with claim 1.

17. A method of inhibiting a lethal factor enzyme released by *bacillus anthraci* where such inhibition is needed, comprising contacting said enzyme with one or more compounds in accordance with claim 1.

18. A method of inhibiting a lethal factor enzyme released by *bacillus anthraci* where such inhibition is needed, comprising administering to a human being infected by *bacillus anthraci* a pharmaceutical composition comprising a pharmaceutically acceptable excipient and one or more compounds in accordance with claim 1.

* * * * *

UNITED STATES PATENT AND TRADEMARK OFFICE
CERTIFICATE OF CORRECTION

| | | |
|---|---|---|
| PATENT NO. | : 8,242,174 B2 | Page 1 of 3 |
| APPLICATION NO. | : 12/011790 | |
| DATED | : August 14, 2012 | |
| INVENTOR(S) | : Johnson et al. | |

It is certified that error appears in the above-identified patent and that said Letters Patent is hereby corrected as shown below:

In column 2 (page 1 item 56) at line 10, Under Other Publications, change "Felxibility" to --Flexibility--.

In column 1 at line 60 (approx.), Change "Biopphys." to --Biophys.--.

In column 1 at line 67 (approx.), Change "*bacillus anthraci*" to --*bacillus anthracis*--.

In column 3 at line 38, Change "heteroayl" to --heteroaryl--.

In column 5 at line 9 (approx.), Change "pharamaceutical" to --pharmaceutical--.

In column 7 at line 48, Change "-pyrroll-yl)-" to --pyrrol-l-yl)--.

In column 9 at line 17, Change "-$CH_2$-1,5" to --$CH_2$-3,5--.

In column 11 at line 4, Change "and or" to --and/or--.

In column 11 at line 15, Change "and or" to --and/or--.

In column 24 at line 29 (approx.), Change "disubstitited" to --disubstituted--.

In column 27 at line 53-54 (approx.), Change "dichoromethane" to --dichloromethane--.

In column 28 at line 28 (approx.), Change ";)$^+$;" to --;--.

In column 40 at line 30 (approx.), After "yield)" insert --.--.

In column 45 at line 33 (approx.), Change "5:3" to --5.3--.

In column 45 at line 48, Change "10" to --1--.

In column 46 at line 67 (approx.), Change "N=6.6" to --$t_R$=6.6--.

In column 54 at line 47 (approx.), After "or" insert --3--.

In column 54 at line 67, After "(M+H)$^+$" insert --.--.

In column 55 at line 11 (approx.), Change "(5)" to --(*S*)--.

Signed and Sealed this
Twenty-sixth Day of February, 2013

Teresa Stanek Rea
*Acting Director of the United States Patent and Trademark Office*

CERTIFICATE OF CORRECTION (continued)
U.S. Pat. No. 8,242,174 B2

In column 82 at line 35-55,

Change " 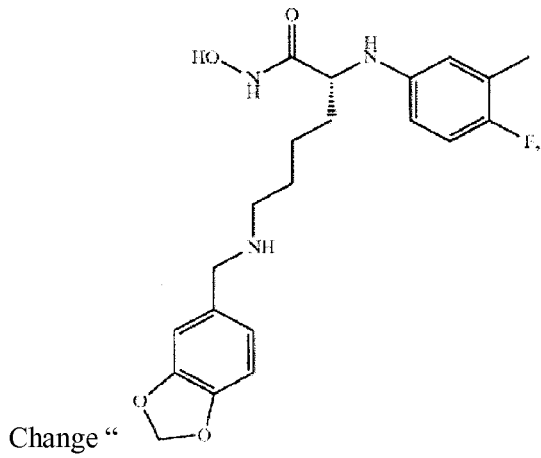 "

to -- 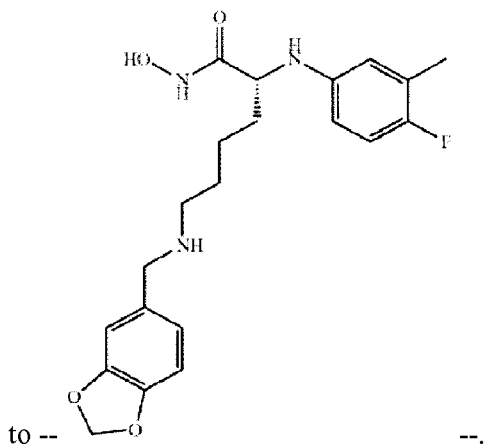 --.

In column 87 at line 64-67,

After " 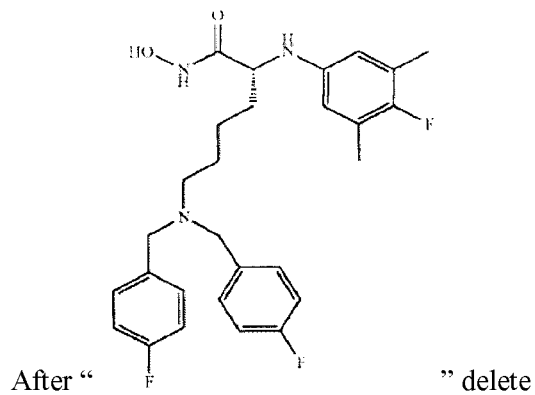 " delete

"(R)-2-(4-Fluoro............................LC-MS: $t_R$=10.4 min, m/z 405 (M+H)$^+$.".

CERTIFICATE OF CORRECTION (continued)
U.S. Pat. No. 8,242,174 B2

In column 90 at line 58, In Claim 6, change "3 Me-4-F-phenyl," to --3-Me-4-F-phenyl,--.

In column 94 at line 17 (approx.), In Claim 14, change "alklylpyridyl" to --alkylpyridyl--.

In column 94 at line 25, In Claim 15, change "*bacillus anthraci*" to --*bacillus anthracis*--.

In column 94 at line 35, In Claim 17, change "*bacillus anthraci*" to --*bacillus anthracis*--.

In column 94 at line 39, In Claim 18, change "*bacillus anthraci*" to --*bacillus anthracis*--.